US008258284B2

(12) United States Patent
Liew et al.

(10) Patent No.: US 8,258,284 B2

(45) Date of Patent: Sep. 4, 2012

(54) KITS AND PRIMERS FOR DIAGNOSING SCHIZOPHRENIA

(75) Inventors: Choong-Chin Liew, Toronto (CA); Thomas Yager, Mississauga (CA); Adam Dempsey, Toronto (CA); Samuel Chao, Concord (CA)

(73) Assignee: GeneNews, Inc., Richmond Hills (CA)

( * ) Notice: Subject to any disclaimer, the term of this patent is extended or adjusted under 35 U.S.C. 154(b) by 44 days.

(21) Appl. No.: 12/777,042

(22) Filed: May 10, 2010

(65) Prior Publication Data

US 2011/0020808 A1 Jan. 27, 2011

Related U.S. Application Data

(62) Division of application No. 12/287,629, filed on Oct. 10, 2008, now Pat. No. 7,713,702.

(51) Int. Cl.
*C07H 21/04* (2006.01)

(52) U.S. Cl. ................. 536/24.33; 536/24.3; 536/24.31; 536/23.1

(58) Field of Classification Search ........................ None
See application file for complete search history.

(56) References Cited

OTHER PUBLICATIONS

NEB catalog (1998/1999), pp. 121, 284.*
Feinberg et al (Analytical Biochemistry, vol. 132, Issue 1, Jul. 1983, pp. 6-13).*

* cited by examiner

*Primary Examiner* — Juliet Switzer
(74) *Attorney, Agent, or Firm* — Kathleen Williams; Amy DeCloux; Edwards Wildman Palmer LLP

(57) ABSTRACT

The invention relates to the identification and selection of novel biomarkers and the identification and selection of novel biomarker combinations which are differentially expressed in blood and useful in diagnosing schizophrenia and/or bipolar disorder as well as monitoring therapeutic efficacy of treatment for schizophrenia or bipolar disorder. The measurement of expression levels of the products of the biomarkers and combinations of biomarkers of the invention can be used to diagnose schizophrenia and/or bipolar disorder. Measurement of the expression level of products of biomarkers of the invention using polynucleotides and proteins which specifically and/or selectively hybridize to the products of the biomarkers of the invention are also encompassed within the scope of the invention as are compositions and kits containing said polynucleotides and proteins. Further encompassed by the invention is the use of the polynucleotides and proteins to monitor the efficacy of therapeutic regimens. The invention also provides for the identification of methods of using the products of the biomarkers of the invention in the identification of novel therapeutic targets of schizophrenia and/or bipolar disorder and a method of screening the genes of said biomarkers for additional markers of disease.

6 Claims, 15 Drawing Sheets

Figure 1

| Gene | Schizophrenia/ Control | BPD/ Control | Schizophrenia/ BPD |
|---|---|---|---|
| | | | |
| ADSS | 0.021 | 0.084 | 0.0006 |
| APOBEC3B | 0.018 | 0.086 | 0.44 |
| ATM | 0.29 | 0.64 | 0.28 |
| CLC | 0.066 | 0.58 | 0.019 |
| CTBP1 | 0.15 | 0.57 | 0.63 |
| CXCL1 | $p<0.001$ | 0.10 | 0.22 |
| DATF1 | 0.01 | 0.50 | 0.016 |
| S100A9 | $<0.001$ | 0.020 | 0.31 |

Figure 2

| External Name | Chromosome Name | Start Position (bp) | Reference ID | SNP Class | Allele |
|---|---|---|---|---|---|
| ADSS | 1 | 240941086 | 1131837 | snp | C/G |
| ADSS | 1 | 240899071 | 2306084 | snp | G/T |
| ADSS | 1 | 240898622 | 3087609 | snp | C/T |
| ADSS | 1 | 240927193 | 3127465 | snp | C/T |
| ADSS | 1 | 240913770 | 6679230 | snp | A/C |
| ADSS | 1 | 240913342 | 12134870 | snp | A/G |
| APOBEC3B | 22 | 37713327 | 760726 | snp | C/T |
| APOBEC3B | 22 | 37712572 | 1053813 | snp | A/G |
| APOBEC3B | 22 | 37712031 | 1065183 | snp | C/T |
| APOBEC3B | 22 | 37712058 | 1065184 | snp | C/T |
| APOBEC3B | 22 | 37713206 | 1804930 | snp | C/T |
| APOBEC3B | 22 | 37710163 | 2072865 | snp | A/G |
| APOBEC3B | 22 | 37706326 | 2076109 | snp | A/G |
| APOBEC3B | 22 | 37706435 | 2076110 | snp | C/T |
| APOBEC3B | 22 | 37706499 | 2076111 | snp | C/T |
| APOBEC3B | 22 | 37712707 | 5757413 | snp | A/G |
| APOBEC3B | 22 | 37712716 | 5757414 | snp | G/T |
| APOBEC3B | 22 | 37706579 | 5995649 | snp | A/C |
| APOBEC3B | 22 | 37712546 | 6001357 | snp | C/G |
| APOBEC3B | 22 | 37706467 | 7511380 | snp | G/T |
| APOBEC3B | 22 | 37711785 | 9611066 | snp | C/T |
| APOBEC3B | 22 | 37706897 | 11705335 | snp | C/G |
| APOBEC3B | 22 | 37713327 | 12484756 | snp | C/T |
| APOBEC3B | 22 | 37712058 | 13054219 | snp | C/T |
| ATM | 11 | 107729907 | 179108 | snp | C/T |
| ATM | 11 | 107741993 | 227092 | snp | G/T |
| ATM | 11 | 107633529 | 641252 | snp | G/T |
| ATM | 11 | 107646911 | 653030 | snp | G/T |
| ATM | 11 | 107730871 | 664143 | snp | C/T |
| ATM | 11 | 107648392 | 664677 | snp | C/T |
| ATM | 11 | 107730693 | 664982 | snp | A/G |
| ATM | 11 | 107634867 | 672655 | snp | A/G |
| ATM | 11 | 107670914 | 681479 | snp | A/C |
| ATM | 11 | 107670946 | 681518 | snp | A/C |
| ATM | 11 | 107627826 | 1060788 | snp | A/G |
| ATM | 11 | 107706381 | 1060793 | snp | A/G |
| ATM | 11 | 107741367 | 1060795 | snp | A/G |
| ATM | 11 | 107647274 | 1064815 | snp | A/T |
| ATM | 11 | 107741281 | 1137889 | snp | A/G |
| ATM | 11 | 107648771 | 1142038 | snp | C/T |
| ATM | 11 | 107611616 | 1442730 | snp | A/G |

Figure 2, Continued

| ATM | 11 | 107611784 | 1442731 | snp | A/G |
|---|---|---|---|---|---|
| ATM | 11 | 107603786 | 1800054 | snp | C/G |
| ATM | 11 | 107629830 | 1800055 | snp | C/T |
| ATM | 11 | 107643213 | 1800056 | snp | C/T |
| ATM | 11 | 107648666 | 1800057 | snp | C/G |
| ATM | 11 | 107665560 | 1800058 | snp | C/T |
| ATM | 11 | 107675716 | 1800059 | snp | A/C |
| ATM | 11 | 107693346 | 1800060 | snp | A/G |
| ATM | 11 | 107702047 | 1800061 | snp | C/G |
| ATM | 11 | 107741136 | 1800558 | snp | G/T |
| ATM | 11 | 107632175 | 1800701 | snp | C/G |
| ATM | 11 | 107624980 | 1800727 | snp | C/G |
| ATM | 11 | 107620988 | 1800735 | snp | G/T |
| ATM | 11 | 107626890 | 1800737 | snp | C/T |
| ATM | 11 | 107621062 | 1800755 | snp | A/C |
| ATM | 11 | 107668697 | 1800889 | snp | C/T |
| ATM | 11 | 107680672 | 1801516 | snp | A/G |
| ATM | 11 | 107680673 | 1801673 | snp | A/T |
| ATM | 11 | 107627802 | 2227924 | snp | C/G |
| ATM | 11 | 107632220 | 2229019 | snp | C/T |
| ATM | 11 | 107665581 | 2229021 | snp | A/G |
| ATM | 11 | 107643135 | 2229022 | snp | C/T |
| ATM | 11 | 107644330 | 2234994 | snp | G/T |
| ATM | 11 | 107611536 | 2234996 | snp | A/G |
| ATM | 11 | 107611653 | 2234997 | snp | A/T |
| ATM | 11 | 107611675 | 2234998 | snp | A/C/G/T |
| ATM | 11 | 107611855 | 2234999 | snp | A/G |
| ATM | 11 | 107626943 | 2235000 | snp | A/G |
| ATM | 11 | 107619842 | 2235001 | snp | G/T |
| ATM | 11 | 107620039 | 2235002 | snp | G/T |
| ATM | 11 | 107620050 | 2235003 | snp | C/T |
| ATM | 11 | 107620093 | 2235004 | snp | C/T |
| ATM | 11 | 107628669 | 2235005 | snp | A/G |
| ATM | 11 | 107627910 | 2235006 | snp | C/T |
| ATM | 11 | 107632083 | 2235007 | snp | C/G |
| ATM | 11 | 107632084 | 2235008 | snp | C/T |
| ATM | 11 | 107632352 | 2235009 | snp | C/T |
| ATM | 11 | 107632355 | 2235010 | snp | A/G |
| ATM | 11 | 107633448 | 2235011 | snp | A/T |
| ATM | 11 | 107719337 | 3017873 | snp | C/T |
| ATM | 11 | 107655419 | 3092824 | in-del | -/T |
| ATM | 11 | 107655562 | 3092825 | snp | C/T |
| ATM | 11 | 107691960 | 3092826 | snp | C/T |
| ATM | 11 | 107680529 | 3092827 | snp | A/G |
| ATM | 11 | 107680597 | 3092828 | snp | C/G |

Figure 2, continued

| ATM | 11 | 107680604 | 3092829 | snp | C/T |
|---|---|---|---|---|---|
| ATM | 11 | 107703610 | 3092831 | snp | A/C |
| ATM | 11 | 107741681 | 3092834 | snp | C/T |
| ATM | 11 | 107741816 | 3092835 | snp | A/G |
| ATM | 11 | 107660130 | 3092840 | snp | A/G |
| ATM | 11 | 107660354 | 3092841 | snp | C/G |
| ATM | 11 | 107660415 | 3092842 | snp | G/T |
| ATM | 11 | 107669261 | 3092849 | snp | G/T |
| ATM | 11 | 107657133 | 3092851 | snp | A/C |
| ATM | 11 | 107664942 | 3092856 | snp | C/T |
| ATM | 11 | 107648509 | 3092857 | snp | A/G |
| ATM | 11 | 107648529 | 3092858 | snp | G/T |
| ATM | 11 | 107648541 | 3092859 | snp | C/T |
| ATM | 11 | 107673217 | 3092872 | snp | C/T |
| ATM | 11 | 107675583 | 3092906 | snp | G/T |
| ATM | 11 | 107677592 | 3092907 | snp | C/G |
| ATM | 11 | 107678710 | 3092908 | snp | G/T |
| ATM | 11 | 107678728 | 3092909 | snp | G/T |
| ATM | 11 | 107686127 | 3092910 | snp | C/T |
| ATM | 11 | 107686268 | 3092911 | snp | A/G |
| ATM | 11 | 107644368 | 3205810 | snp | A/G |
| ATM | 11 | 107658742 | 3205813 | snp | C/T |
| ATM | 11 | 107691863 | 3212321 | snp | C/T |
| ATM | 11 | 107655580 | 3218668 | snp | A/G |
| ATM | 11 | 107692080 | 3218669 | snp | A/G |
| ATM | 11 | 107691953 | 3218670 | snp | A/G |
| ATM | 11 | 107655615 | 3218671 | snp | A/G |
| ATM | 11 | 107675763 | 3218672 | snp | A/G |
| ATM | 11 | 107643255 | 3218673 | snp | C/T |
| ATM | 11 | 107620797 | 3218674 | snp | C/T |
| ATM | 11 | 107704984 | 3218675 | snp | C/T |
| ATM | 11 | 107697369 | 3218677 | snp | G/T |
| ATM | 11 | 107670844 | 3218678 | snp | A/G |
| ATM | 11 | 107647404 | 3218679 | snp | A/G |
| ATM | 11 | 107711020 | 3218680 | snp | A/G |
| ATM | 11 | 107656918 | 3218681 | in-del | -/A |
| ATM | 11 | 107670836 | 3218682 | snp | G/T |
| ATM | 11 | 107696069 | 3218683 | in-del | -/A |
| ATM | 11 | 107603773 | 3218684 | snp | C/T |
| ATM | 11 | 107683948 | 3218686 | snp | A/G |
| ATM | 11 | 107644393 | 3218687 | snp | A/G |
| ATM | 11 | 107644532 | 3218688 | snp | C/T |
| ATM | 11 | 107648426 | 3218689 | snp | A/G |
| ATM | 11 | 107603802 | 3218690 | snp | C/T |
| ATM | 11 | 107656908 | 3218691 | in-del | -/T |

Figure 2, continued

| | | | | | |
|---|---|---|---|---|---|
| ATM | 11 | 107632299 | 3218692 | snp | A/C |
| ATM | 11 | 107603453 | 3218693 | snp | A/G |
| ATM | 11 | 107634988 | 3218695 | snp | A/C |
| ATM | 11 | 107692066 | 3218696 | snp | C/G |
| ATM | 11 | 107663496 | 3218697 | snp | A/G |
| ATM | 11 | 107655418 | 3218698 | in-del | -/T |
| ATM | 11 | 107701469 | 3218699 | snp | C/T |
| ATM | 11 | 107701973 | 3218700 | snp | A/C |
| ATM | 11 | 107686026 | 3218701 | snp | A/G |
| ATM | 11 | 107603483 | 3218703 | snp | A/G |
| ATM | 11 | 107709728 | 3218704 | snp | A/C |
| ATM | 11 | 107632311 | 3218705 | snp | A/C |
| ATM | 11 | 107620749 | 3218706 | snp | A/G |
| ATM | 11 | 107619937 | 3218707 | snp | C/G |
| ATM | 11 | 107644512 | 3218708 | snp | C/T |
| ATM | 11 | 107660450 | 3218709 | snp | A/G |
| ATM | 11 | 107611845 | 3218710 | snp | A/G |
| ATM | 11 | 107741474 | 3218711 | snp | C/G |
| ATM | 11 | 107660458 | 3218712 | snp | A/G |
| ATM | 11 | 107730715 | 3741058 | snp | A/G |
| ATM | 11 | 107629971 | 4986761 | snp | C/T |
| ATM | 11 | 107729825 | 4986839 | snp | A/C |
| ATM | 11 | 107605098 | 4987907 | snp | A/G |
| ATM | 11 | 107620682 | 4987918 | snp | A/T |
| ATM | 11 | 107620688 | 4987919 | snp | C/T |
| ATM | 11 | 107622815 | 4987928 | snp | A/G |
| ATM | 11 | 107624813 | 4987935 | snp | A/G |
| ATM | 11 | 107625139 | 4987936 | snp | A/T |
| ATM | 11 | 107626656 | 4987943 | snp | A/G |
| ATM | 11 | 107627802 | 4987945 | snp | C/G |
| ATM | 11 | 107628033 | 4987946 | snp | C/T |
| ATM | 11 | 107629696 | 4987951 | snp | G/T |
| ATM | 11 | 107644260 | 4987970 | in-del | -/T |
| ATM | 11 | 107663440 | 4988000 | snp | A/G |
| ATM | 11 | 107668592 | 4988008 | snp | C/T |
| ATM | 11 | 107673361 | 4988018 | snp | C/G |
| ATM | 11 | 107686324 | 4988069 | snp | A/G |
| ATM | 11 | 107701173 | 4988103 | snp | C/G |
| ATM | 11 | 107701182 | 4988104 | snp | C/G |
| ATM | 11 | 107703601 | 4988111 | snp | C/T |
| ATM | 11 | 107703776 | 4988112 | snp | A/C |
| ATM | 11 | 107708829 | 4988125 | snp | C/T |
| ATM | 11 | 107665581 | 5031003 | snp | A/G |
| ATM | 11 | 107603568 | 7112053 | snp | C/G |
| ATM | 11 | 107691820 | 11212587 | snp | A/G |

Figure 2, continued

| ATM | 11 | 107741985 | 11300039 | in-del | -/A |
|---|---|---|---|---|---|
| ATM | 11 | 107741967 | 11336610 | in-del | -/A |
| ATM | 11 | 107701187 | 11366542 | in-del | -/T |
| ATM | 11 | 107719386 | 11824991 | snp | A/G |
| ATM | 11 | 107624819 | 12273020 | snp | C/T |
| ATM | 11 | 107721661 | 12279930 | snp | A/G |
| ATM | 11 | 107657087 | 12786957 | snp | A/C |
| ATM | 11 | 107657092 | 12786960 | snp | A/C |
| ATM | 11 | 107656987 | 12788418 | snp | G/T |
| ATM | 11 | 107657008 | 12788427 | snp | G/T |
| ATM | 11 | 107657011 | 12788429 | snp | G/T |
| CLC | 19 | 44917486 | 374185 | snp | A/G |
| CLC | 19 | 44916673 | 375867 | snp | A/T |
| CLC | 19 | 44916826 | 384138 | snp | A/G |
| CLC | 19 | 44916709 | 391646 | snp | A/T |
| CLC | 19 | 44916727 | 391660 | snp | C/T |
| CLC | 19 | 44917008 | 399641 | snp | A/T |
| CLC | 19 | 44916741 | 453827 | snp | A/G |
| CLC | 19 | 44916734 | 2074927 | snp | C/T |
| CLC | 19 | 44917623 | 10403365 | snp | C/T |
| CTBP1 | 4 | 1209006 | 1045458 | snp | C/T |
| CTBP1 | 4 | 1195831 | 1045466 | snp | A/C |
| CTBP1 | 4 | 1195779 | 1045469 | snp | C/G |
| CTBP1 | 4 | 1195722 | 1045470 | snp | C/G |
| CTBP1 | 4 | 1195498 | 1045479 | snp | G/T |
| CTBP1 | 4 | 1195497 | 1045480 | snp | G/T |
| CTBP1 | 4 | 1195567 | 4974572 | snp | A/T |
| CTBP1 | 4 | 1196562 | 7687296 | snp | A/C |
| CTBP1 | 4 | 1195413 | 11540633 | snp | C/T |
| CTBP1 | 4 | 1221956 | 12500584 | snp | A/C |
| CXCL1 | 4 | 75100769 | 2018732 | snp | C/T |
| CXCL1 | 4 | 75100279 | 2071425 | snp | A/G |
| CXCL1 | 4 | 75100559 | 7656335 | snp | C/G |
| CXCL1 | 4 | 75100185 | 11547681 | snp | G/T |
| CXCL1 | 4 | 75100292 | 13104984 | snp | A/C |
| CXCL1 | 4 | 75100769 | 2018732 | snp | C/T |
| CXCL1 | 4 | 75100279 | 2071425 | snp | A/G |
| CXCL1 | 4 | 75100559 | 7656335 | snp | C/G |
| CXCL1 | 4 | 75100185 | 11547681 | snp | G/T |
| CXCL1 | 4 | 75100292 | 13104984 | snp | A/C |
| CXCL1 | 4 | 75100769 | 2018732 | snp | C/T |
| CXCL1 | 4 | 75100279 | 2071425 | snp | A/G |
| CXCL1 | 4 | 75100559 | 7656335 | snp | C/G |
| DATF1 | 20 | 60996665 | 750077 | snp | C/G |
| DATF1 | 20 | 60996625 | 750078 | snp | A/G |

Figure 2, continued

| DATF1 | 20 | 60996159 | 753691 | snp | A/C |
|---|---|---|---|---|---|
| DATF1 | 20 | 60998519 | 910149 | snp | C/T |
| DATF1 | 20 | 61007120 | 1056996 | snp | C/T |
| DATF1 | 20 | 60998716 | 1883847 | snp | C/T |
| DATF1 | 20 | 60998751 | 1883848 | snp | A/G |
| DATF1 | 20 | 60998008 | 2013097 | snp | A/G |
| DATF1 | 20 | 60994578 | 2294998 | snp | C/T |
| DATF1 | 20 | 61007334 | 2294999 | snp | A/G |
| DATF1 | 20 | 61007383 | 2295000 | snp | A/G |
| DATF1 | 20 | 61011473 | 2295001 | snp | C/G |
| DATF1 | 20 | 60996787 | 4491775 | snp | A/G |
| DATF1 | 20 | 61010764 | 6010784 | snp | C/T |
| DATF1 | 20 | 61011754 | 6010785 | snp | C/T |
| DATF1 | 20 | 60993784 | 6011448 | snp | C/T |
| DATF1 | 20 | 60995708 | 6062740 | snp | A/G |
| DATF1 | 20 | 60996137 | 6062741 | snp | A/G |
| DATF1 | 20 | 61007501 | 6062745 | snp | G/T |
| DATF1 | 20 | 61012583 | 6090160 | snp | A/G |
| DATF1 | 20 | 61013372 | 6090161 | snp | A/G |
| DATF1 | 20 | 60996739 | 7271159 | snp | C/T |
| DATF1 | 20 | 61039968 | 8120151 | snp | C/G |
| DATF1 | 20 | 61007926 | 8121918 | snp | A/T |
| DATF1 | 20 | 60994840 | 11362069 | in-del | -/T |
| DATF1 | 20 | 60996869 | 11475986 | in-del | -/A |
| DATF1 | 20 | 60995684 | 11699796 | snp | A/G |
| DATF1 | 20 | 61039576 | 11700272 | snp | A/G |
| DATF1 | 20 | 61013308 | 11907248 | snp | A/G |
| S100A9 | 1 | 150146418 | 743565 | snp | A/G |
| S100A9 | 1 | 150146438 | 743566 | snp | G/T |
| S100A9 | 1 | 150146328 | 1063933 | snp | A/G |
| S100A9 | 1 | 150144055 | 2916195 | snp | C/T |
| S100A9 | 1 | 150146578 | 3014868 | snp | C/T |
| S100A9 | 1 | 150146391 | 11544410 | snp | C/T |
| S100A9 | 1 | 150146418 | 743565 | snp | A/G |
| S100A9 | 1 | 150146438 | 743566 | snp | G/T |
| S100A9 | 1 | 150146328 | 1063933 | snp | A/G |
| S100A9 | 1 | 150144055 | 2916195 | snp | C/T |
| S100A9 | 1 | 150146578 | 3014868 | snp | C/T |
| S100A9 | 1 | 150146391 | 11544410 | snp | C/T |

Figure 3

Combinations of Two Genes Useful as Biomarkers of Liver Cancer

| | ADS | APO | ATM | CLC | CTB | CXC | DAT | S10 |
|---|---|---|---|---|---|---|---|---|
| ADS | - | APO ADS | ATM ADS | CLC ADS | CTB ADS | CXC ADS | DAT ADS | S10 ADS |
| APO | - | - | ATM APO | CLC APO | CTB APO | CXC APO | DAT APO | S10 APO |
| ATM | - | - | - | CLC ATM | CTB ATM | CXC ATM | DAT ATM | S10 ATM |
| CLC | - | - | - | - | CTB CLC | CXC CLC | DAT CLC | S10 CLC |
| CTB | - | - | - | - | - | CXC CTB | DAT CTB | S10 CTB |
| CXC | - | - | - | - | - | - | DAT CXC | S10 CXC |
| DAT | - | - | - | - | - | - | - | S10 DAT |
| S10 | - | - | - | - | - | - | - | - |

Figure 4 Combinations of Three Genes Useful as Biomarkers of Schizophrenia and/or Bipolar Disorder (a) ADS

| | ADS | APO | ATM | CLC | CTB | CXC | DAT | S10 |
|---|---|---|---|---|---|---|---|---|
| ADS | - | - | - | - | - | - | - | - |
| APO | - | - | ATM APO ADS | CLC APO ADS | CTB APO ADS | CXC APO ADS | DAT APO ADS | S10 APO ADS |
| ATM | - | - | - | CLC ATM ADS | CTB ATM ADS | CXC ATM ADS | DAT ATM ADS | S10 ATM ADS |
| CLC | - | - | - | - | CTB CLC ADS | CXC CLC ADS | DAT CLC ADS | S10 CLC ADS |
| CTB | - | - | - | - | - | CXC CTB ADS | DAT CTB ADS | S10 CTB ADS |
| CXC | - | - | - | - | - | - | DAT CXC ADS | S10 CXC ADS |
| DAT | - | - | - | - | - | - | - | S10 DAT ADS |
| S10 | - | - | - | - | - | - | - | - |

(b) APO

| | ADS | APO | ATM | CLC | CTB | CXC | DAT | S10 |
|---|---|---|---|---|---|---|---|---|
| ADS | - | - | ATM APO ADS | CLC | CTB | CXC | DAT | S10 |
| APO | - | - | - | - | - | - | - | - |
| ATM | - | - | - | CLC ATM Apo | CTB ATM APO | CXC ATM APO | DAT ATM APO | S10 ATM APO |
| CLC | - | - | - | - | CTB CLC APO | CXC CLC APO | DAT CLC APO | S10 CLC APO |
| CTB | - | - | - | - | - | CXC CTB APO | DAT CTB APO | S10 CTB APO |
| CXC | - | - | - | - | - | - | DAT CXC APO | S10 CXC APO |
| DAT | - | - | - | - | - | - | - | S10 DAT APO |
| S10 | - | - | - | - | - | - | - | - |

Figure 4 Continued (c) ATM

| | ADS | APO | ATM | CLC | CTB | CXC | DAT | S10 |
|---|---|---|---|---|---|---|---|---|
| ADS | - | APO<br>ADS<br>ATM | - | CLC<br>ADS<br>ATM | CTB<br>ADS<br>ATM | CXC<br>ADS<br>ATM | DAT<br>ADS<br>ATM | S10<br>ADS<br>ATM |
| APO | - | - | - | CLC<br>APO<br>ATM | CTB<br>APO<br>ATM | CXC<br>APO<br>ATM | DAT<br>APO<br>ATM | S10<br>APO<br>ATM |
| ATM | - | - | - | - | | | | |
| CLC | - | - | - | - | CTB<br>CLC<br>ATM | CXC<br>CLC<br>ATM | DAT<br>CLC<br>ATM | S10<br>CLC<br>ATM |
| CTB | - | - | - | - | - | CXC<br>CTB<br>ATM | DAT<br>CTB<br>ATM | S10<br>CTB<br>ATM |
| CXC | - | - | - | - | - | - | DAT<br>CXC<br>ATM | S10<br>CXC<br>ATM |
| DAT | - | - | - | - | - | - | - | S10<br>DAT<br>ATM |
| S10 | - | - | - | - | - | - | - | - |

(d) CLC

| | ADS | APO | ATM | CLC | CTB | CXC | DAT | S10 |
|---|---|---|---|---|---|---|---|---|
| ADS | - | APO<br>ADS<br>CLC | ATM<br>ADS<br>CLC | - | CTB<br>ADS<br>CLC | CXC<br>ADS<br>CLC | DAT<br>ADS<br>CLC | S10<br>ADS<br>CLC |
| APO | - | - | ATM<br>APO<br>CLC | - | CTB<br>APO<br>CLC | CXC<br>APO<br>CLC | DAT<br>APO<br>CLC | S10<br>APO<br>CLC |
| ATM | - | - | - | - | CTB<br>ATM<br>CLC | CXC<br>ATM<br>CLC | DAT<br>ATM<br>CLC | S10<br>ATM<br>CLC |
| CLC | - | - | - | - | - | - | - | - |
| CTB | - | - | - | - | - | CXC<br>CTB<br>CLC | DAT<br>CTB<br>CLC | S10<br>CTB<br>CLC |
| CXC | - | - | - | - | - | - | DAT<br>CXC<br>CLC | S10<br>CXC<br>CLC |
| DAT | - | - | - | - | - | - | - | S10<br>DAT<br>CLC |
| S10 | - | - | - | - | - | - | - | - |

Figure 4 Continued (e) CTB

| | ADS | APO | ATM | CLC | CTB | CXC | DAT | S10 |
|---|---|---|---|---|---|---|---|---|
| ADS | - | APO<br>ADS<br>CTB | ATM<br>ADS<br>CTB | CLC<br>ADS<br>CTB | - | CXC<br>ADS<br>CTB | DAT<br>ADS<br>CTB | S10<br>ADS<br>CTB |
| APO | - | - | ATM<br>APO<br>CTB | CLC<br>APO<br>CTB | - | CXC<br>APO<br>CTB | DAT<br>APO<br>CTB | S10<br>APO<br>CTB |
| ATM | - | - | - | CLC<br>ATM<br>CTB | - | CXC<br>ATM<br>CTB | DAT<br>ATM<br>CTB | S10<br>ATM<br>CTB |
| CLC | - | - | - | - | - | CXC<br>CLC<br>CTB | DAT<br>CLC<br>CTB | S10<br>CLC<br>CTB |
| CTB | - | - | - | - | - | - | - | - |
| CXC | - | - | - | - | - | - | DAT<br>CXC<br>CTB | S10<br>CXC<br>CTB |
| DAT | - | - | - | - | - | - | - | S10<br>DAT<br>CTB |
| S10 | - | - | - | - | - | - | - | - |

(f) CXC

| | ADS | APO | ATM | CLC | CTB | CXC | DAT | S10 |
|---|---|---|---|---|---|---|---|---|
| ADS | - | APO<br>ADS<br>CXC | ATM<br>ADS<br>CXC | CLC<br>ADS<br>CXC | CTB<br>ADS<br>CXC | - | DAT<br>ADS<br>CXC | S10<br>ADS<br>CXC |
| APO | - | - | ATM<br>APO<br>CXC | CLC<br>APO<br>CXC | CTB<br>APO<br>CXC | - | DAT<br>APO<br>CXC | S10<br>APO<br>CXC |
| ATM | - | - | - | CLC<br>ATM<br>CXC | CTB<br>ATM<br>CXC | - | DAT<br>ATM<br>CXC | S10<br>ATM<br>CXC |
| CLC | - | - | - | - | CTB<br>CLC<br>CXC | - | DAT<br>CLC<br>CXC | S10<br>CLC<br>CXC |
| CTB | - | - | - | - | - | - | DAT<br>CTB<br>CXC | S10<br>CTB<br>CXC |
| CXC | - | - | - | - | - | - | - | - |
| DAT | - | - | - | - | - | - | - | S10<br>DAT<br>CXC |
| S10 | - | - | - | - | - | - | - | - |

Figure 4 Continued (g) DAT

| | ADS | APO | ATM | CLC | CTB | CXC | DAT | S10 |
|---|---|---|---|---|---|---|---|---|
| ADS | - | APO<br>ADS<br>DAT | ATM<br>ADS<br>DAT | CLC<br>ADS<br>DAT | CTB<br>ADS<br>DAT | CXC<br>ADS<br>DAT | - | S10<br>ADS<br>DAT |
| APO | - | - | ATM<br>APO<br>DAT | CLC<br>APO<br>DAT | CTB<br>APO<br>DAT | CXC<br>APO<br>DAT | - | S10<br>APO<br>DATB |
| ATM | - | - | - | CLC<br>ATM<br>DAT | CTB<br>ATM<br>DAT | CXC<br>ATM<br>DAT | - | S10<br>ATM<br>DAT |
| CLC | - | - | - | - | CTB<br>CLC<br>DAT | CXC<br>CLC<br>DAT | - | S10<br>CLC<br>DAT |
| CTB | - | - | - | - | - | CXC<br>CTB<br>DAT | - | S10<br>CTB<br>DAT |
| CXC | - | - | - | - | - | - | - | S10<br>CXC<br>DAT |
| DAT | - | - | - | - | - | - | - | - |
| S10 | - | - | - | - | - | - | - | - |

KITS AND PRIMERS FOR DIAGNOSING SCHIZOPHRENIA

RELATED APPLICATIONS

This application is a division of U.S. patent application Ser. No. 12/287,629 filed Oct. 10, 2008, which is a division of U.S. patent application Ser. No. 10/989,191 filed Nov. 15, 2004, now abandoned, which is a Continuation-in-part of PCT/US2004/020836 filed Jun. 21, 2004, and which is a Continuation-in-part of U.S. patent application Ser. No. 10/812,731 filed Mar. 30, 2004, which is a Continuation-in-part of U.S. patent application Ser. No. 10/802,875 filed Mar. 30, 2004, now abandoned .

1. FIELD OF THE INVENTION

The invention relates to the identification and selection of novel biomarkers and the identification and selection of novel biomarker combinations which are differentially expressed in individuals with schizophrenia and/or bipolar disorder as well as a means of selecting the novel biomarker combinations. Further encompassed by the invention is the use of polynucleotides and/or proteins which specifically hybridize to the products of the biomarkers of the invention to diagnose schizophrenia, diagnose bipolar disorder and differentially diagnose as between schizophrenia and bipolar disorder. Also included in the invention are kits of said polynucleotides and/or proteins. The invention also encompasses screening methods to monitor the efficacy of therapeutic regimens and identify therapeutic targets for treating schizophrenia and/or bipolar disorder, as well as providing a means of identifying single nucleotide point mutations related to schizophrenia and/or bipolar disorder.

2. BACKGROUND OF THE INVENTION

Schizophrenia:

Schizophrenia is a debilitating mental disorder characterized primarily by psychotic symptoms including hallucinations, delusions, disorganized speech, thought and behaviour, and difficulty expressing emotion. The lifetime prevalence of schizophrenia is about 1% of the population worldwide, with some countries slightly lower and others slightly higher. In the United States, roughly 2,500,000 people are affected by it.

Diagnosis of Schizophrenia

Currently diagnosis of schizophrenia relies solely on the analysis of a person's symptoms. Diagnosis is made from information obtained from physicial examination, taking a person's family history and emotional history, as well as a medical evaluation, and a mental status examination. Relying on symptomatic history makes diagnosis of schizophrenia difficult, particularly since no single symptom is definitive for diagnosis. Rather, the diagnosis encompasses a pattern of signs and symptoms, in conjunction with impaired occupational or social functioning. Currently diagnosis includes looking for delusions (false beliefs strongly held in spite of invalidating evidence); visual, auditory, tactile, olfactory or gustatory hallucinations; disorganized speech; disorganized thinking; grossly disorganized thinking and/or catatonic behaviour; negative symptoms, such as emotional deficit, avolition (inability to initiate and persist in goal-directed activities) and alogia (poverty of speech) are also symptoms of schizophrenia. Continuous signs of the disturbance must persist for at least 6 months. This 6-month period must include at least 1 month of active-phase symptoms (listed above) (or less if successfully treated) and may include periods of prodromal or residual symptoms. During these prodromal or residual periods, the signs of the disturbance may be manifested by only negative symptoms or two or more active-phase symptoms in an attenuated form (e.g., odd beliefs, unusual perceptual experiences).

Diagnosis of schizophrenia is made even harder because it is often difficult to differentiate schizophrenia from other mental disorders including bipolar disorder, schizoaffective disorder, and brief psychotic disorder. In addition, diagnosis of schizophrenia is often confused with other organic medical conditions (e.g. encephalitis) or substance conditions (drugs of abuse, such as amphetamines and phencyclidine, or other medications). Although recently brain imaging techniques have been utilized as a tool towards diagnosis, this is costly, is inconvenient to patients, and is not considered very reliable.

Bipolar Disorder:

Bipolar disorder, (also termed manic-depressive disorder), is a mood disorder in which people experience alternating episodes of mania and major depression. Mania is characterized by elation, irritability, excitability, racing thought and speech, and hyperactivity. Major depression is characterized by sadness, withdrawal, despair, and suicidal thoughts. Bipolar disorder affects approximately 3% of people in the United States. The age of onset is usually the late teens or early 20s and there is usually a history of depression. Generally, early treatment means better prognosis.

Diagnosis of Bipolar Disorder

Traditional medical diagnostic techniques for diagnosing bipolar disorder include: physical exam and history and mental status exam for presence of bipolar disorder symptoms which include a combination of at least one major depressive episode (a depressed mood or a loss of interest or pleasure in daily activities consistently for at least a 2 week period which represents a change from the person's normal mood; social, occupational, educational or other important functioning must also be negatively impaired by the change in mood) and one manic episode (a distinct period of persistently elevated, expansive, or irritable mood, lasting throughout at least 4 days, that is clearly different from the usual nondepressed mood). Diagnosis can be difficult because the first episode of mania may go undetected, and an episode of depression does not necessarily predict a subsequent manic episode. Most people are symptom free for months or even years between episodes of depression and mania. In brief, both schizophrenia and bipolar disorder are difficult to diagnose due to the complexity of each condition. Moreover, it can be challenging to clinically distinguish these two conditions because of their common clinical characteristics. It often requires a long period of observation of a patient before the definitive diagnosis can be made. Although there are brain-imaging tests available, they are not specific enough. Recently there has been some advancement in analyzing gene expression in brain tissue to identify biomarkers of mental disorders, but one cannot translate this into a simple non invasive diagnostic tool. Blood-based tests for diagnosis and differential diagnosis of schizophrenia and bipolar disorder would help speed up the diagnostic process and ensure an early administration of the correct therapy. This is particularly important since there are effective therapies available to manage both schizophrenia and bipolar disorder, and early treatment in many cases means better prognosis and decreases chances of recurrence of future acute episodes.

Thus there is a need for a simple non-invasive diagnostic test for diagnosing an individual as having either schizophrenia or bipolar disorder.

3. SUMMARY OF THE INVENTION

The invention relates to the identification and selection of novel biomarkers and the identification and selection of novel biomarker combinations which are differentially expressed in blood and useful in diagnosing schizophrenia and/or bipolar disorder as well as monitoring therapeutic efficacy of treatment for schizophrenia and/or bipolar disorder. The measurement of expression levels of the products of the biomarkers and combinations of biomarkers of the invention can be used to diagnose schizophrenia and/or bipolar disorder. Measurement of the expression level of products of biomarkers of the invention using polynucleotides and proteins which specifically and/or selectively hybridize to the products of the biomarkers of the invention are also encompassed within the scope of the invention as are compositions and kits containing said polynucleotides and proteins. Further encompassed by the invention is the use of the polynucleotides and proteins to monitor the efficacy of therapeutic regimens. The invention also provides for the identification of methods of using the biomarkers of the invention in the identification of novel therapeutic targets of schizophrenia and/or bipolar disorder and a method of screening the genes of said biomarkers for additional markers of disease.

4. BRIEF DESCRIPTION OF THE DRAWINGS

The objects and features of the invention can be better understood with reference to the following detailed description and drawings.

FIG. 1 is a figure showing, in one embodiment of the invention, p values representing the differential expression for each of the biomarkers of the invention when comparing subpopulations of individuals as follows: (a) schizophrenia v. non schizophrenia (control) (b) bipolar disorder (bpd) v. non bipolar disorder (control) and (c) schizophrenia v. bipolar disorder.

FIG. 2 is a table showing, in one embodiment of the invention, SNPs which have been identified in the biomarkers of the invention FIG. 3 is a table showing, in one embodiment of the invention, various selections of two biomarkers of the invention.

FIG. 4 is a table showing, in one embodiment of the invention, various selections of three biomarkers of the invention.

5. DETAILED DESCRIPTION OF THE INVENTION

Figure 5:
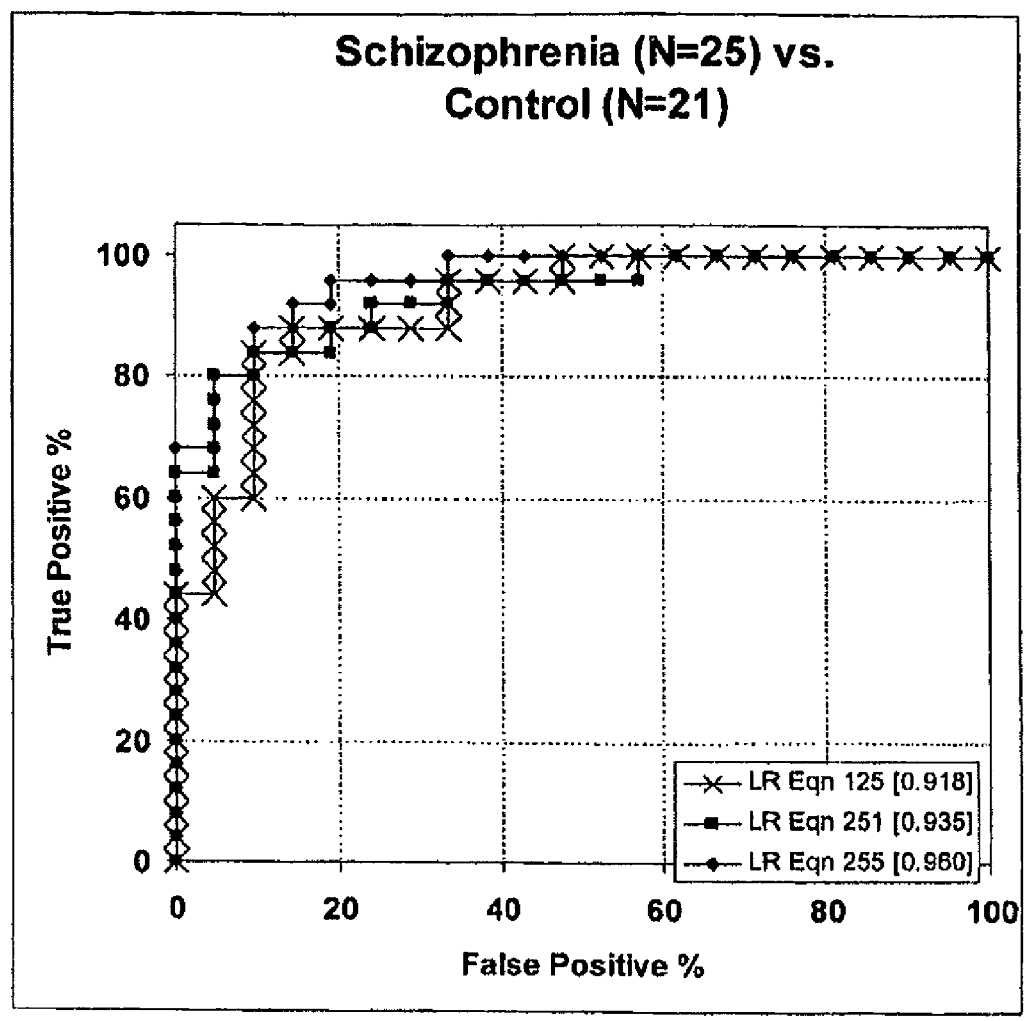
FIG. 5 is an example of a number of classifiers generated for use in differentiating as between schizophrenia and normal (non schizophrenia) with an ROC of >0.9.

The invention relates to the identification and selection from blood of genes which are differentially expressed as between individuals with schizophrenia and normal individuals; individuals with bipolar disorder and normal individuals; and as between individuals with schizophrenia and individuals with bipolar disorder. As such the invention encompasses polynucleotides and polypeptides which can be used to detect and monitor differential gene expression of the biomarker and biomarker combinations for both diagnosis of schizophrenia and diagnosis of bipolar disorder as well as to allow the monitoring of potential therapeutic treatments for both schizophrenia and bipolar disorder. The invention further encompasses a method of identifying particularly useful combinations of biomarkers. In addition the invention encompasses use of the biomarkers of the invention to screen for therapeutic targets for schizophrenia and bipolar disorder and identifies single nucleotide polymorphisms within the genes of the invention which can be monitored to determine additional means of diagnosing schizophrenia or bipolar disorder in individuals.

5.1 Definitions

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference in their entireties.

The following definitions are provided for specific terms which are used in the following written description. As used herein, the "5' end" refers to the end of an mRNA up to the first 1000 nucleotides or ⅓ of the mRNA(where the fill length of the mRNA does not include the poly A tail), starting at the first nucleotide of the mRNA. The "5' region" of a gene refers to a polynucleotide (double-stranded or single-stranded) located within or at the 5' end of a gene, and includes, but is not limited to, the 5' untranslated region, if that is present, and the 5' protein coding region of a gene. The 5' region is not shorter than 8 nucleotides in length and not longer than 1000 nucleotides in length. Other possible lengths of the 5' region include but are not limited to 10, 20, 25, 50, 100, 200, 400, and 500 nucleotides.

As used herein, the "3' end" refers to the end of an mRNA up to the last 1000 nucleotides or ⅓ of the mRNA, where the 3' terminal nucleotide is that terminal nucleotide of the coding or untranslated region that adjoins the poly-A tail, if one is present. That is, the 3' end of an mRNA does not include the poly-A tail, if one is present. The "3' region" of a gene refers to a polynucleotide (double-stranded or single-stranded) located within or at the 3' end of a gene, and includes, but is not limited to, the 3' untranslated region, if that is present, and the 3' protein coding region of a gene. The 3' region is not shorter than 8 nucleotides in length and not longer than 1000 nucleotides in length. Other possible lengths of the 3' region include but are not limited to 10, 20, 25, 50, 100, 200, 400, and 500 nucleotides. As used herein, the "internal coding region" of a gene refers to a polynucleotide (double-stranded or single-stranded) located between the 5' region and the 3' region of a gene as defined herein. The "internal coding region" is not shorter than 8 nucleotides in length and not longer than 1000 nucleotides in length. Other possible lengths of the "internal coding region" include but are not limited to 10, 20, 25, 50, 100, 200, 400, and 500 nucleotides. The 5', 3' and internal regions are non-overlapping and may, but need not be contiguous, and may, but need not, add up to the full length of the corresponding gene.

As used herein, the "amino terminal" region of a polypeptide refers to the polypeptide sequences encoded by polynucleotide sequences (double-stranded or single-stranded) located within or at the 5' end of a gene, and includes, but is not limited to, the 5' protein coding region of a gene. As used herein, the "amino terminal" region refers to the amino terminal end of a polypeptide up to the first 300 amino acids or ⅓ of the polypeptide, starting at the first amino acid of the polypeptide. The "amino terminal" region of a polypeptide is not shorter than 3 amino acids in length and not longer than 350 amino acids in length. Other possible lengths of the "amino terminal" region of a polypeptide include but are not limited to 5, 10, 20, 25, 50, 100 and 200 amino acids.

As used herein, the "carboxy terminal" region of a polypeptide refers to the polypeptide sequences encoded by polynucleotide sequences (double-stranded or single-stranded) located within or at the 3' end of a gene, and includes, but is not limited to, the 3' protein coding region of a gene. As used herein, the "carboxy terminal" region refers to the carboxy terminal end of a polypeptide up to 300 amino acids or ⅓ of the polypeptide from the last amino acid of the polypeptide. The "3' end" does not include the polyA tail, if one is present. The "carboxy terminal" region of a polypeptide is not shorter than 3 amino acids in length and not longer than 350 amino acids in length. Other possible lengths of the "carboxy terminal" region of a polypeptide include, but are not limited to, 5, 10, 20, 25, 50, 100 and 200 amino acids.

As used herein, the "internal polypeptide region" of a polypeptide refers to the polypeptide sequences located between the amino terminal region and the carboxy terminal region of a polypeptide, as defined herein. The "internal polypeptide region" of a polypeptide is not shorter than 3 amino acids in length and not longer than 350 amino acids in length. Other possible lengths of the "internal polypeptide region" of a polypeptide include, but are not limited to, 5, 10, 20, 25, 50, 100 and 200 amino acids. The amino terminal, carboxy terminal and internal polypeptide regions of a polypeptide are non-overlapping and may, but need not be contiguous, and may, but need not, add up to the full length of the corresponding polypeptide.

As used herein, the term "amplified", when applied to a nucleic acid sequence, refers to a process whereby one or more copies of a particular nucleic acid sequence is generated from a template nucleic acid, preferably by the method of polymerase chain reaction (Mullis and Faloona, 1987, Methods Enzymol., 155:335). "Polymerase chain reaction" or "PCR" refers to an in vitro method for amplifying a specific nucleic acid template sequence. The PCR reaction involves a repetitive series of temperature cycles and is typically performed in a volume of 50-100 □l. The reaction mix comprises dNTPs (each of the four deoxynucleotides dATP, dCTP, dGTP, and dTTP), primers, buffers, DNA polymerase, and nucleic acid template. The PCR reaction comprises providing a set of polynucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of polynucleotide primers" or "a set of PCR primers" can comprise two, three, four or more primers. In one embodiment, an exo-Pfu DNA polymerase is used to amplify a nucleic acid template in PCR reaction. Other methods of amplification include, but are not limited to, ligase chain reaction (LCR), polynucleotide-specific based amplification (NSBA), or any other method known in the art.

According to the invention, an "array" contemplates a specific set of genes immobilized to a support, or a set of corresponding 5' ends or a set of corresponding 3' ends or a set of corresponding internal coding regions. Of course, mixtures of a 5' end of one gene may be used as a target or a probe in combination with a 3' end of another gene to achieve the same result of schizophrenia or bipoloar disorder diagnosis.

As used herein, the term "analog" in the context of proteinaceous agent (e.g., proteins, polypeptides, peptides, and antibodies) refers to a proteinaceous agent that possesses a similar or identical function as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions.times.100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous analog refers to a second organic or inorganic molecule which possess a similar or identical function as a first organic or inorganic molecule and is structurally similar to the first organic or inorganic molecule. The term "analog" includes a molecule whose core structure is the same as, or closely resembles that of the first molecule, but which has a chemical or physical modification. the term "analog" includes copolymers of the first molecule that can be linked to other atoms or molecules. A "biologically active analog" and "anolog" are used interchangeably herein to cover an organic or inorganic molecule that exhibits substantially the same agonist or antagonist effect of the first organic or inorganic molecule.

A "nucleotide analog", as used herein, refers to a nucleotide in which the pentose sugar and/or one or more of the phosphate esters is replaced with its respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage. Further included within "nucleotide analogs" are nucleotides in which the nucleobase moiety is non-conventional, i.e., differs from one of G, A, T, U or C. Generally a non-conventional nucleobase will have the capacity to form hydrogen bonds with at least one nucleobase moiety present on an adjacent counter-directional polynucleotide strand or provide a non-interacting, non-interfering base.

The term "antibody" also encompasses antigen-binding fragments of an antibody. The term "antigen-binding fragment" of an antibody (or simply "antibody portion," or "fragment"), as used herein, refers to one or more fragments of a full-length antibody that retain the ability to specifically bind to a polypeptide encoded by one of the genes of a biomarker of the invention. Examples of binding fragments encompassed within the term "antigen-binding fragment" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The antibody is preferably monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

As used herein, the terms "attaching" and "spotting" refer to a process of depositing a nucleic acid onto a substrate to form a nucleic acid array such that the nucleic acid is stably bound to the substrate via covalent bonds, hydrogen bonds or ionic interactions.

As used herein, the term "biomarker" refers to a gene that is differentially regulated as between individuals with (a) schizophrenia and normal individuals (individuals without schizophrenia) (b) bipolar disorder and normal individuals (individuals without bipolar disorder) and (c) schizophrenia and bipolar disorder.

As used herein, a "blood nucleic acid sample", refers to nucleic acids derived from blood and can include nucleic acids derived from whole blood, centrifuged lysed blood, serum free whole blood or peripheral blood leukocytes (PBLs). By whole blood is meant unseparated whole blood, for example, a drop of whole blood. By centrifuged lysed blood or 'lysed blood' is meant whole blood that is mixed with lysis buffer and centrifuged as described herein (see Example 2). By serum free blood is meant whole blood wherein the serum or plasma is removed by centrifugation as described herein (see Example 2). Preferably, a blood nucleic acid sample is whole blood or centrifuged lysed blood and is total RNA, mRNA or is a nucleic acid corresponding to mRNA, for example, cDNA derived from mRNA isolated from said blood. A nucleic acid sample can also include a PCR product derived from total RNA, mRNA or cDNA.

As used herein, the term "brain cells" includes those cells found in the brain and include neurons, and glial cells, including Schwann's Cells, Satellite Cells, Microglia cels, Oligodendroglia cells, and Astroglia cells and all cell lines thereof.

As used herein, the term 'centrifuged' refers to the centrifugation of serum free whole blood or lysed blood at 2000 rpm (800 g) for 5 minutes at 4° C.

As used herein, the term "classifier" is used to describe the output of a mathematical model generated on its ability to differentiate between two or more phenotypic traits—for example having or not having schizophrenia, having or not having bipolar disorder and either having schizophrenia or bipolar disorder.

As used herein, the terms "compound" and "agent" are used interchangably.

As used herein, "consisting essentially of" refers to the maximum number of genes that are required for the use of a biomarker to diagnose schizophrenia or bipolar disorder. In one embodiment, a biomarker for the diagnosis of schizophrenia consists essentially of at least 2, 3, 4, 5, 6, 7, or all of the biomarkers of the invention. In another embodiment, a biomarker for the diagnosis of bipolar disorder consists essentially of at least 2, 3, 4, 5, 6, 7, or all of the biomarkers of the invention. In another embodiment, a biomarker for differentiating between schizophrenia and bipolar disorder consists essentially of at least 2, 3, 4, 5, 6, 7 or all of the biomarkers of the invention. In another embodiment, a biomarker for diagnosis of schizophrenia consists essentially of any one of the biomarkers in Table 3. In another embodiment, a biomarker for diagnosis of bipolar disorder consists essentially of any one of the biomarkers in Table 4. In another embodiment, a biomarker for differentiating between schizophrenia and bipolar disorder consists essentially of any one of the Biomarkers in Table 5.

As used herein, the term "control" or "control sample" in the context of this invention refers to one or more tissue nucleic acid samples and/or a blood nucleic acid samples isolated from an individual or group of individuals who are either classified as having schizophrenia, having bipolar disorder or not having schizophrenia or bipolar disorder where the diagnosis for the "control" or "control sample" has been confirmed. The term control or control sample can also refer to the compilation of data derived from samples of one or more individuals whose diagnosis has been confirmed as normal (not having schizophrenia or bipolar disorder) or one or more individuals whose diagnosis has been confirmed as having schizophrenia or bipolar disorder.

A "coding region" refers to a DNA sequence encoding mRNA.

As used herein, the terms "compound" and "agent" are used interchangably. As used herein, the term "derivative" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses a similar or identical function as the proteinaceous agent from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein, "diagnosis" refers to a process of determining if an individual is afflicted with a disease or ailment. "Diagnosis of schizophrenia" or "schizophrenia diagnosis" refers to a process of determining if an individual is afflicted with schizophrenia and includes both traditional medical diagnostic techniques for diagnosing schizophrenia, as well as diagnostic methods as encompassed by the invention. In one embodiment, diagnosis of schizophrenia using methods as encompassed by the invention includes determining whether a person has schizophrenia or does not have schizophrenia. In another embodiment, diagnosis of schizophrenia includes determining whether a person has schizophrenia or bipolar disorder. "Diagnosis of bipolar disorder" or "bipolar disorder diagnosis" refers to a process of determining if an individual is afflicted with bipolar disorder and includes both traditional medical diagnostic techniques for diagnosing bipolar disorder, as well as diagnostic methods as encompassed by the invention. In one embodiment, diagnosis of bipolar disorder using methods as encompassed by the invention includes determining whether a person has bipolar disorder or does not have bipolar disorder. In another embodiment, diagnosis includes determining whether a person has bipolar disorder or schizophrenia. Traditional medical diagnostic techniques for diagnosing schizophrenia include: physical exam and history, medical evaluation, and a mental status exam and appropriate laboratory tests which can include an MRI. The diagnosis often encompasses a pattern of signs and symptoms, in conjunction with impaired occupational or social functioning. Currently diagnosis includes looking for delusions (false beliefs strongly held in spite of invalidating evidence); visual, auditory, tactile, olfactory or gustatory hallucinations; disorganized speech; disorganized thinking; grossly disorganized thinking and/or catatonic behaviour; negative symptoms, such as emotional deficit, avolition (inability to initiate and persist in goal-directed activities) and alogia (poverty of speech) are also symptoms of schizophrenia. Traditional medical diagnostic techniques for diagnosing bipolar disorder include: physical exam and history and mental status exam for presence of bipolar disorder symptoms which include a combination of at least one major depressive episode (a depressed mood or a loss of interest or pleasure in daily activities consistently for at least a 2 week period which represents a change from the person's normal mood; social, occupational, educational or other important functioning must also be negatively impaired by the change in mood) and one manic episode (a distinct period of persistently elevated, expansive, or irritable mood, lasting throughout at least 4 days, that is clearly different from the usual nondepressed mood). In a specific embodiment, "diagnosis of schizophrenia" refers to a determination as between two options: e.g. that an individual has schizophrenia or that an individual does not have schizophrenia; or e.g. that an individual has schizophrenia or that an individual has bipolar disorder; or e.g. than an individual has bipolar disorder or does not have bipolar disorder. In another embodiment, "diagnosis" can also refer to a determination as between three options e.g. an individual has bipolar disorder, an individual has schizophrenia or an individual has neither. In another embodiment diagnosis can include an option that it cannot be determined with sufficient degree of certainty as to whether an individual can be characterized as having schizophrenia, having bipolar disorder or having either. As would be understood by a person skilled in the art, in this context a "sufficient degree of certainty" depends upon the medical requirements for both the sensitivity and specificity of the diagnosis. More particularly the sufficient degree of certainly includes greater than 50% sensitivity and/or specificity, greater than 60% sensitivity and/or specificity, greater than 70% sensitivity and/or specificity, greater than 80% sensitivity and/or specificity, greater than 90% sensitivity and/or specificity and 100% sensitivity and/or specificity. Note that diagnosis can also refer to the results of a series of individual diagnosis so as to make an ultimate diagnosis (e.g. a first diagnosis to determine whether an individual has schizophrenia or does not have schizophrenia and second test to determine whether said individual has schizophrenia or is bipolar where the results of both tests lead to a diagnosis of schizophrenia or bipolar disorder).

As used herein, "normal" in the context of a conventional diagnosis refers to an individual or group of individuals who have not shown any symptoms of either schizophrenia or bipolar disorder and are not known to have either schizophrenia or bipolar disorder. Preferably said normal individual(s) is not on medication affecting schizophrenia or bipolar disorder. More preferably said normal individual(s) is not on medication affecting mental health. If possible said individual or group of individuals has not been diagnosed with any other disease. It is also helpful if the normal individuals have similar sex, and age as compared with the test individuals. "Normal", according to the invention, also refers to a samples isolated from normal individuals and includes blood, total RNA or mRNA isolated from normal individuals. A sample taken from a normal individual can include RNA isolated from a blood sample wherein said blood sample is whole blood, lysed blood, centrifuged lysed blood or peripheral blood leukocytes (PBLs), and wherein the blood is from an individual who has not been diagnosed with either schizophrenia or bipolar disorder and does not show any symptoms of schizophrenia or bipolar disorder at the time the blood is isolated.

As used herein, the term "differential expression" refers to a difference in the level of expression of the RNA of one or more biomarkers of the invention, as measured by the amount or level mRNA, and/or one or more spliced variants of mRNA of the biomarker in one sample as compared with the level of expression of the same one or more biomarkers of the invention in a second sample. "Differentially expressed" can also include a measurement of the protein encoded by the biomarker of the invention in a sample or population of samples as compared with the amount or level of protein expression in a second sample or population of samples. Differential expression can be determined as described herein and as would be understood by a person skilled in the art. The term "differentially expressed" or "changes in the level of expression" refers to an increase or decrease in the measurable expression level of a given biomarker as measured by the amount of RNA and/or the amount of protein in a sample as compared with the measurable expression level of a given biomarker a second sample. The term "differentially expressed" or "changes in the level of expression" can also refer to an increase or decrease in the measurable expression level of a given biomarker in a population of samples as compared with the measurable expression level of a biomarker in a second population of samples. As used herein, "differentially expressed" can be measured using the ratio of the level of expression of a given biomarker(s) as compared with the mean expression level of the given biomarker(s) of a control wherein the ratio is not equal to 1.0. Differentially expressed can also be measured using p-value. When using p-value, a biomarker is identified as being differentially expressed as between a first and second population when the p-value is less than 0.1. More preferably the p-value is less than 0.05. Even more preferably the p-value is less than 0.01. More preferably still the p-value is less than 0.005. Most preferably the p-value is less than 0.001. When determining differentially expression on the basis of the ratio, an RNA or protein is differentially expressed if the ratio of the level of expression in a first sample as compared with a second sample is greater than or less than 1.0. For example, a ratio of greater than 1.2, 1.5, 1.7, 2, 3, 4, 10, 20 or a ratio less than 1, for example 0.8, 0.6, 0.4, 0.2, 0.1. 0.05. In another embodiment of the invention a nucleic acid transcript is differentially expressed if the ratio of the mean of the level of expression of a first population as compared with the mean level of expression of the second population is greater than or less than 1.0 For example, a ratio of greater than 1.2, 1.5, 1.7, 2, 3, 4, 10, 20 or a ratio less than 1, for example 0.8, 0.6, 0.4, 0.2, 0.1. 0.05. In another embodiment of the invention a nucleic acid transcript is differentially expressed if the ratio of its level of expression in a first sample as compared with the mean of the second population is greater than or less than 1.0 and includes for example, a ratio of greater than 1.2, 1.5, 1.7, 2, 3, 4, 10, 20, or a ratio less than 1, for example 0.8, 0.6, 0.4, 0.2, 0.1. 0.05.

"Differentially increased expression" or "up regulation" refers to genes which demonstrate at least 10% or more, for example, 20%, 30%, 40%, or 50%, 60%, 70%, 80%, 90% or more or 1.1 fold, 1.2 fold, 1.4 fold, 1.6 fold, 1.8 fold, or more increase in gene expression (as measured by RNA expression or protein expression), relative to a control.

"Differentially decreased expression" or "down regulation" refers to genes which demonstrate at least 10% or more, for example, 20%, 30%, 40%, or 50%, 60%, 70%, 80%, 90% or a less than 1.0 fold, 0.8 fold, 0.6 fold, 0.4 fold, 0.2 fold, 0.1 fold or less decrease in gene expression (as measured by RNA expression or protein expression), relative to a control. For example, up regulated genes includes genes having an increased level of expression of mRNA or protein in blood isolated from individuals characterized as having schizophrenia as compared with expression of mRNA or protein isolated from normal individuals. For example, down regulated genes includes genes having a decreased level of expression in blood isolated from individuals characterized as having schizophrenia as compared with blood isolated from normal individuals. As used herein, the term "differential hybridization" refers to a difference in the quantitative level of hybridization of a nucleic acid sample from a first individual or individuals with a trait to a complementary nucleic acid target as compared with the hybridization of a nucleic acid sample from a second individual or individuals not having said trait to the same complementary nucleic acid target. A "differential hybridization" means that the ratio of the level of hybridization of the first sample as compared with the second sample is not equal to 1.0. For example, the ratio of the level of hybridization of the first sample to the target as compared to the second sample is greater than or less than 1.0, and includes greater than 1.5 and less than 0.7, greater than 2 and less than 0.5. A differential hybridization also exists if the hybridization is detectable in one sample but not another sample.

As used herein, the term "drug efficacy" refers to the effectiveness of a drug. "Drug efficacy" is usually measured by the clinical response of the patient who has been or is being treated with a drug. A drug is considered to have a high degree of efficacy, if it achieves desired clinical results, for example, the alteration of gene expression and the gene expression pattern reflective of schizophrenia or bipolar disorder as described herein. The amount of drug absorbed may be used to predict a patient's response. A general rule is that as the dose of a drug is increased, a greater effect is seen in the patient until a maximum desired effect is reached. If more drug is administered after the maximum point is reached, the side effects will normally increase.

As used herein, the term "effective amount" refers to the amount of a compound which is sufficient to reduce or ameliorate the progression, severity and/or duration of schizophrenia or bipolar disorder, or schizophrenic episodes/bipolar episodes or one or more symptoms thereof, prevent the development, recurrence or onset of schizophrenia and/or bipolar disorder or one or more symptoms thereof, prevent the advancement of schizophrenia and/or bipolar disorder or one or more symptoms thereof, or enhance or improve the prophylactic or therapeutic effect(s) of another therapy.

As used herein, the term "fragment" in the context of a proteinaceous agent refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide or a protein. In a specific embodiment, a fragment of a protein or polypeptide retains at least one function of the protein or polypeptide. In another embodiment, a fragment of a protein or polypeptide retains at least two, three, four, or five functions of the protein or polypeptide. Preferably, a fragment of an antibody retains the ability to immunospecifically bind to an antigen.

As used herein, the term "fusion protein" refers to a polypeptide that comprises an amino acid sequence of a first protein or polypeptide or functional fragment, analog or derivative thereof, and an amino acid sequence of a heterologous protein, polypeptide, or peptide (i.e., a second protein or polypeptide or fragment, analog or derivative thereof different than the first protein or fragment, analog or derivative thereof). In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent.

As used herein, a "gene expression pattern" or "gene expression profile" indicates the combined pattern of the results of the analysis of the level of expression of two or more biomarkers of the invention including 3, 4, 5, 6, 7, 8, 9, 10, 11, 12 or all of the biomarkers of the invention. A gene expression pattern or gene expression profile can result from the measurement of expression of the products of the biomarkers of the invention and can be done using any known technique. For example techniques to measure expression of the RNA products of the biomarkers of the invention includes, PCR based methods (including RT-PCR) and non PCR based method as well as microarray analysis. To measure protein products of the biomarkers of the invention, techniques include western blotting and ELISA analysis.

As used herein, the term "hybridizing to" or "hybridization" refers to the sequence specific non-covalent binding interactions with a complementary nucleic acid, for exampleinteractions between a target nucleic acid sequence and a nucleic acid member on an array.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

As used herein, the term "in combination" when referring to therapeutic treatments refers to the use of more than one type of therapy (e.g., more than one prophylactic agent and/or therapeutic agent). The use of the term "in combination" does not restrict the order in which therapies (e.g., prophylactic and/or therapeutic agents) are administered to a subject. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject.

As used herein, "indicative of disease" when referring to an expression pattern indicates an expression pattern which is diagnostic of disease such that the expression pattern is found significantly more often in patients with a disease than in patients without the disease (as determined using routine statistical methods setting confidence levels at a minimum of 95%). Preferably, an expression pattern which is indicative of disease is found in at least 70%, at least 75%, at least 80%, at least 85%, at least 90%, at least 95% or more in patients who have the disease and is found in less than 10%, less than 8%, less than 5%, less than 2.5%, or less than 1% of patients who do not have the disease. "Indicative of disease" also indicates an expression pattern which is diagnostic of disease such that the expression pattern more properly categorizes with control expression patterns of individuals with disease as compared with control expression patterns of individuals without disease using statistical algorithms for class prediction as would be understood by a person skilled in the art and see for example commercially available programs such as those provided by Silicon Genetics (e.g. GeneSpring™)

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes.

As used herein, the terms "isolated" and "purified" in the context of a proteinaceous agent (e.g., a peptide, polypeptide, protein or antibody) refer to a proteinaceous agent which is substantially free of cellular material and in some embodiments, substantially free of heterologous proteinaceous agents (i.e., contaminating proteins) from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous proteinaceous agent (e.g., protein, polypeptide, peptide, or antibody; also referred to as a "contaminating protein"). When the proteinaceous agent is recombinantly produced, it is also preferably substantially free of culture medium, i.e., culture medium represents less than about 20%, 10%, or 5% of the volume of the protein preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. Preferably, proteinaceous agents disclosed herein are isolated.

As used herein, the term "level of expression" when referring to RNA refers to the measurable quantity of a given nucleic acid as determined by hybridization or measurements such as real-time RT PCR, which includes use of both SYBR® green and TaqMan® technology and which corresponds in direct proportion with the extent to which the gene is expressed. The level of expression of a nucleic acid is determined by methods well known in the art. For microarray analysis, the level of expression is measured by hybridization analysis using labeled nucleic acids corresponding to RNA isolated from one or more individuals according to methods well known in the art. The label on the nucleic acid used for hybridization can be a luminescent label, an enzymatic label, a radioactive label, a chemical label or a physical label. Preferably, target nucleic acids are labeled with a fluorescent molecule. Preferred fluorescent labels include, but are not limited to: fluorescein, amino coumarin acetic acid, tetramethylrhodamine isothiocyanate (TRITC), Texas Red, Cyanine 3 (Cy3) and Cyanine 5 (Cy5).

As used herein, a "ligand" is a molecule that specifically binds to a polypeptide encoded by one of the genes of a biomarker of the invention. A ligand can be a nucleic acid (RNA or DNA), polypeptide, peptide or chemical compound. A ligand of the invention can be a peptide ligand, e.g., a scaffold peptide, a linear peptide, or a cyclic peptide. In a preferred embodiment, the polypeptide ligand is an antibody. The antibody can be a human antibody, a chimeric antibody, a recombinant antibody, a humanized antibody, a monoclonal antibody, or a polyclonal antibody. The antibody can be an intact immunoglobulin, e.g., an IgA, IgG, IgE, IgD, IgM or subtypes thereof. The antibody can be conjugated to a functional moiety (e.g., a compound which has a biological or chemical function (which may be a second different polypeptide, a therapeutic drug, a cytotoxic agent, a detectable moiety, or a support. A polypeptide ligand e.g. antibody of the invention interacts with a polypeptide, encoded by one of the genes of a biomarker, with high affinity and specificity. For example, the polypeptide ligand binds to a polypeptide, encoded by one of the genes of a biomarker, with an affinity constant of at least 107 $M^{-1}$, preferably, at least $10^8$ $M^{-1}$, $10^9$ $M^{-1}$, or $10^{10}$ $M^{-1}$.

An "mRNA" means an RNA complementary to a gene; an mRNA includes a protein coding region and also may include 5' end and 3' untranslated regions (UTR).

As used herein, the term "majority" refers to a number representing more than 50% (e.g., 51%, 60%, or 70%, or 80% or 90% or up to 100%) of the total members of a composition. The term "majority", when referring to an array, it means more than 50% (e.g., 51%, 60%, or 70%, or 80% or 90% or up to 100%) of the total nucleic acid members that are stably associated with the solid substrate of the array.

As used herein, the terms "manage", "managing" and "management" refer to the beneficial effects that a subject derives from a therapy (e.g., a prophylactic or therapeutic agent) which does not result in a cure of schizophrenia and/or bipolar disorder. In certain embodiments, a subject is administered one or more therapies to "manage" schizophrenia and/or bipolar disorder so as to ameliorate symptoms of schizophrenia and/or bipolar disorder, and/or to prevent and/or retard the progression of these diseases and or symptoms of these diseases.

Amelioration of schizophrenia and/or bipolar disorder is defined herein as providing physical or physiological relief to individuals and can include relief of symptoms as well as a decrease in episode number or episode duration. Treatment of schizophrenia and/or bipolar disorder is defined herein to provide medical aid to counteract the disease itself, the symptoms and or episodes of the disease (either in number or duration) and/or the progression of the disease. These treatments may be given as palliative therapy to help relieve symptoms and improve the quality of life.

As used herein, "mRNA integrity" refers to the quality of mRNA extracts from either tissue samples or blood samples. mRNA extracts with good integrity do not appear to be degraded when examined by methods well known in the art, for example, by RNA agarose gel electrophoresis (e.g., Ausubel et al., John Weley & Sons, Inc., 1997*, Current Protocols in Molecular Biology*). Preferably, the mRNA samples have good integrity (e.g., less than 10%, preferably less than 5%, and more preferably less than 1% of the mRNA is degraded) to truly represent the gene expression levels of the tissue or blood samples from which they are extracted.

As used herein, the terms "non-responsive" and refractory" describe patients treated with a currently available therapy (e.g., prophylactic or therapeutic agent) for schizophrenia and/or bipolar disorder, which is not clinically adequate to relieve one or more symptoms associated therewith. Typically, such patients suffer from severe, persistently active schizophrenia and/or bipolar disorder and require additional therapy to ameliorate the symptoms associated with their disease.

As used herein, "nucleic acid(s)" is interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations thereof and can include expressed sequence tags (ESTs) according to some embodiments of the invention. An EST is a portion of the expressed sequence of a gene (i.e., the "tag" of a sequence), made by reverse transcribing a region of mRNA so as to make cDNA.

As defined herein, a "nucleic acid array" refers a plurality of nucleic acids (or "nucleic acid members") attached to a support where each of the nucleic acid members is attached to a support in a unique pre-selected region. In one embodiment, the nucleic acid member attached to the surface of the support is DNA. In a preferred embodiment, the nucleic acid member attached to the surface of the support is either cDNA or oligonucleotides. In another preferred embodiment, the nucleic acid member attached to the surface of the support is cDNA synthesized by polymerase chain reaction (PCR). The term "nucleic acid", as used herein, is interchangeable with the term "polynucleotide". In another preferred embodiment, a "nucleic acid array" refers to a plurality of unique nucleic acids attached to nitrocellulose or other membranes used in Southern and/or Northern blotting techniques.

As used herein "nucleic acid sample for hybridization to an array" is defined as a nucleic acid capable of binding to a nucleic acid bound to an array of complementary sequence through sets of non-covalent bonding interactions including complementary base pairing interactions. The nucleic acid sample for hybridization to an array can either be an isolated nucleic acid sequence corresponding to a gene or portion thereof, total RNA or mRNA isolated from a sample. Preferably, the nucleic acid sample for hybridization to an array is derived from human blood (including whole blood, lysed blood, centrifuged lysed blood, or peripheral blood leukocytes (PBLs)). More preferably, the nucleic acid sample is single- or double-stranded DNA, RNA, or DNA-RNA hybrids, from human blood and preferably from RNA or mRNA extracts.

As used herein, a "nucleic acid member on an array" or a "nucleic acid member" includes nucleic acid immobilized on an array and capable of binding to a nucleic acid probes or samples of complementary sequence through sets of non-covalent bonding interactions, including complementary base pairing interactions. As used herein, a nucleic acid member or target may include natural (i.e., A, G, C, or T) or modified bases (7-deazaguanosine, inosine, etc.). In addition, the bases in nucleic acids may be joined by a linkage other than a phosphodiester bond, so long as it does not interfere with hybridization (i.e., the nucleic acid target still specifically binds to its complementary sequence under standard stringent or selective hybridization conditions). Thus, nucleic acid members may be peptide nucleic acids in which the constituent bases are joined by peptide bonds rather than phosphodiester linkages. In one embodiment, a conventional nucleic acid array of 'target' sequences bound to the array can be representative of the entire human genome, e.g. Affymetrix chip, and the biomarker or isolated biomarker consisting of or comprising two or more of the 3 genes described in FIG. 1 or gene probes is applied to the conventional array. In another embodiment, sequences bound to the array can be the biomarker or isolated biomarker according to the invention and total cellular RNA is applied to the array.

As used herein, the term "oligonucleotide" is defined as a molecule comprised of two or more deoxyribonucleotides and/or ribonucleotides, and preferably more than three. Its exact size will depend upon many factors which, in turn, depend upon the ultimate function and use of the oligonucleotide. The oligonucleotides may be from about 8 to about 1,000 nucleotides long. Although oligonucleotides of 8 to 100 nucleotides are useful in the invention, preferred oligonucleotides range from about 8 to about 15 bases in length, from about 8 to about 20 bases in length, from about 8 to about 25 bases in length, from about 8 to about 30 bases in length, from about 8 to about 40 bases in length or from about 8 to about 50 bases in length.

As used herein, "patient" or "individual" refers to a mammal who is diagnosed with schizophrenia and/or bipolar disorder.

As used herein, the phrase "pharmaceutically acceptable salt(s)," includes, but is not limited to, salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, "polynucleotide" encompasses double-stranded DNA, single-stranded DNA and double-stranded or single-stranded RNA of more than 8 nucleotides in length. The term "polynucleotide" includes a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components.

As used herein, "polypeptide sequences encoded by" refers to the amino acid sequences obtained after translation of the protein coding region of a gene, as defined herein. The mRNA nucleotide sequence for each of the genes of the invention is identified by its Genbank Accession number (see Table 2) and the corresponding polypeptide sequence is identified by a Protein Accession number (see Table 2) The Genbank Accession numbers identified in Table 2 provides the location of the 5' UTR, protein coding region (CDS) and 3' UTR within the mRNA nucleotide sequence of each of the genes of the invention. When a protein or fragment of a protein is used to immunize a host animal, numerous regions of the protein may induce the production of antibodies which bind specifically to a given region or three-dimensional structure on the protein; these regions or structures are referred to as epitopes or antigenic determinants. As used herein, "antigenic fragments" refers portions of a polypeptide that contains one or more epitopes. Epitopes can be linear, comprising essentially a linear sequence from the antigen, or conformational, comprising sequences which are genetically separated by other sequences but come together structurally at the binding site for the polypeptide ligand. "Antigenic fragments" may be 5000, 1000, 500, 400, 300, 200, 100, 50 or 25 or 20 or 10 or 5 amino acids in length.

As used herein, the terms "prevent", "preventing" and "prevention" refer to the prevention of the development, recurrence or onset of schizophrenia and/or bipolar disorder or one or more symptoms and/or episodes thereof resulting from the administration of one or more compounds identified in accordance the methods of the invention or the administration of a combination of such a compound and another therapy.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art.

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length as long as it is less than the full length of the target gene. Probes can include oligonucleotides modified so as to have a tag which is detectable by fluorescence, chemiluminescence and the like. The probe can also be modified so as to have both a detectable tag and a quencher molecule, for example Taqman® and Molecular Beacon® probes.

The oligonucleotides and analogs thereof may be RNA or DNA, or analogs of RNA or DNA, commonly referred to as antisense oligomers or antisense oligonucleotides. Such RNA or DNA analogs comprise but are not limited to 2-'O-alkyl sugar modifications, methylphosphonate, phosphorothioate, phosphorodithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (Egholm, et al. Peptide Nucleic Acids (PNA)—Oligonucleotide Analogues with an Achiral Peptide Backbone, (1992)).

Probes may also be mixtures of any of the oligonucleotide analog types together or in combination with native DNA or RNA. At the same time, the oligonucleotides and analogs thereof may be used alone or in combination with one or more additional oligonucleotides or analogs thereof.

As used herein, "a plurality of" or "a set of" refers to more than two, for example, 3 or more, 4 or more, 5 or more, 6 or more, 7 or more, 8 or more, 9 or more 10 or more etc.

As used herein, "pre-selected region", "predefined region", or "unique position" refers to a localized area on a substrate which is, was, or is intended to be used for the deposit of a nucleic acid and is otherwise referred to herein in the alternative as a "selected region" or simply a "region." The pre-selected region may have any convenient shape, e.g., circular, rectangular, elliptical, wedge-shaped, etc. In some embodiments, a pre-selected region is smaller than about 1 $cm^2$, more preferably less than 1 $mm^2$, still more preferably less than 0.5 $mm^2$, and in some embodiments less than 0.1 $mm^2$. A nucleic acid member at a "pre-selected region", "predefined region", or "unique position" is one whose identity (e.g., sequence) can be determined by virtue of its position at the region or unique position.

As used herein the term "product of the biomarker" or "products of the biomarkers of the invention" refers to the RNA and/or the protein expressed by the gene corresponding to the biomarker of the invention. In the case of RNA it refers to the RNA transcripts transcribed from genes corresponding to the biomarker of the invention. In the case of protein it refers to proteins translated from the genes corresponding to the biomarker of the invention. The "RNA product of a biomarker of the invention" includes mRNA transcripts, and/or specific spliced variants of mRNA whose measure of expression can be used as a biomarker in accordance with the teachings disclosed herein. The "protein product of a biomarker of the invention" includes proteins translated from the RNA products of the biomarkers of the invention.

As used herein, the terms "prophylactic agent" and "prophylactic agents" refer to any compound(s) which can be used in the prevention of schizophrenia and/or bipolar disorder. In certain embodiments, the term "prophylactic agent" refers to a compound identified in the screening assays described herein. In certain other embodiments, the term "prophylactic agent" refers to an agent other than a compound identified in the screening assays described herein which is known to be useful for, or has been or is currently being used to prevent or impede the onset, development and/or progression of schizophrenia and/or bipolar disorder or one or more symptoms and/or episodes thereof.

As used herein, the phrase "prophylactically effective amount" refers to the amount of a therapy (e.g., a prophylactic agent) which is sufficient to result in the prevention of the development, recurrence or onset or progression of schizophrenia and/or bipolar disorder or one or more symptoms and/or episodes thereof.

As used herein, the terms "protein" and "polypeptide" are used interchangeably to refer to a chain of amino acids linked together by peptide bonds. In a specific embodiment, a protein is composed of less than 200, less than 175, less than 150, less than 125, less than 100, less than 50, less than 45, less than 40, less than 35, less than 30, less than 25, less than 20, less than 15, less than 10, or less than 5 amino acids linked together by peptide bonds. In another embodiment, a protein is composed of at least 200, at least 250, at least 300, at least 350, at least 400, at least 450, at least 500 or more amino acids linked together by peptide bonds.

A "protein coding region" refers to the portion of the mRNA encoding a polypeptide.

As used herein the "reference population" or "test population" refers a population of "control samples" used to develop the classifier to differentiate between (a) schizophrenic and normal individuals; (b) bipolar disorder individuals and normal individuals or (c) schizophrenic individuals and bipolar disorder individuals. The "reference population" or "test population" is comprised of a number of control samples depending upon the classifier to be constructed and can include the following: (a) individuals diagnosed with schizophrenia using conventional diagnostic techniques, (b) individuals diagnosed with bipolar disorder using conventional techniques and (c) individuals having neither bipolar disorder or schizophrenia. In a preferred embodiment the "reference population" or "test population" is comprised of an equal number of "control samples" from each phenotypic subgroup (e.g. wherein said phenotype is a determination of status with regards to schizophrenia or bipolar disorder). In another embodiment, the "reference population" is also matched for other phenotypes e.g. age, sex, drug status, etc.

As used herein, the term "selectively binds" in the context of proteins encompassed by the invention refers to the specific interaction of a any two of a peptide, a protein, a polypeptide an antibody, wherein the interaction preferentially occurs as between any two of a peptide, protein, polypeptide and antibody preferentially as compared with any other peptide, protein, polypeptide and antibody. For example, when the two molecules are protein molecules, a structure on the first molecule recognizes and binds to a structure on the second molecule, rather than to other proteins. "Selective binding", "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As used herein "selective hybridization" in the context of this invention refers to a hybridization which occurs as between a polynucleotide encompassed by the invention and an RNA or protein product of the biomarker of the invention wherein the hybridization is such that the polynucleotide binds to the RNA products of the biomarker of the invention preferentially to the RNA products of other genes in the genome in question. In a preferred embodiment a polynucleotide which "selectively hybridizes" is one which hybridizes with a selectivity of greater than 70%, greater than 80%, greater than 90% and most preferably on 100% (ie cross hybridization with other RNA species preferably occurs at less than 30%, less than 20%, less than 10%). As would be understood to a person skilled in the art, a polynucleotide which "selectively hybridizes" to the RNA product of a biomarker of the invention can be determined taking into account the length and composition.

As used herein, "specifically hybridizes", "specific hybridization" refers to hybridization which occurs when two nucleic acid sequences are substantially complementary (at least about 65% complementary over a stretch of at least 14 to 25 nucleotides, preferably at least about 75% complementary, more preferably at least about 90% complementary). See Kanehisa, M., 1984, Nucleic acids Res., 12:203, incorporated herein by reference. As a result, it is expected that a certain degree of mismatch is tolerated. Such mismatch may be small, such as a mono-, di- or tri-nucleotide. Alternatively, a region of mismatch can encompass loops, which are defined as regions in which there exists a mismatch in an uninterrupted series of four or more nucleotides. Numerous factors influence the efficiency and selectivity of hybridization of two nucleic acids, for example, the hybridization of a nucleic acid member on an array to a target nucleic acid sequence. These factors include nucleic acid member length, nucleotide sequence and/or composition, hybridization temperature, buffer composition and potential for steric hindrance in the region to which the nucleic acid member is required to hybridize. A positive correlation exists between the nucleic acid length and both the efficiency and accuracy with which a nucleic acid will anneal to a target sequence. In particular, longer sequences have a higher melting temperature ($T_M$) than do shorter ones, and are less likely to be repeated within a given target sequence, thereby minimizing non-specific hybridization. Hybridization temperature varies inversely with nucleic acid member annealing efficiency. Similarly the concentration of organic solvents, e.g., formamide, in a hybridization mixture varies inversely with annealing efficiency, while increases in salt concentration in the hybridization mixture facilitate annealing. Under stringent annealing conditions, longer nucleic acids, hybridize more efficiently than do shorter ones, which are sufficient under more permissive conditions As used herein, "spotting" or "attaching" refers to a process of depositing a nucleic acid member onto a solid substrate to form a nucleic acid array such that the nucleic acid is stably bound to the solid substrate via covalent bonds, hydrogen bonds or ionic interactions.

As used herein, "stably associated" refers to a nucleic acid that is stably bound to a solid substrate to form an array via covalent bonds, hydrogen bonds or ionic interactions such that the nucleic acid retains its unique pre-selected position relative to all other nucleic acids that are stably associated with an array, or to all other pre-selected regions on the solid substrate under conditions in which an array is typically analyzed (i.e., during one or more steps of hybridization, washes, and/or scanning, etc.).

As used herein, "substrate" or "support" when referring to an array refers to a material having a rigid or semi-rigid surface. The support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, (poly)tetrafluoroethylene, (poly)vinylidenedifluoride, polystyrene, polycarbonate, a charged membrane, such as nylon 66 or nitrocellulose, or combinations thereof. In a preferred embodiment, the support is glass. Preferably, at least one surface of the substrate will be substantially flat. Preferably, the support will contain reactive groups, including, but not limited to, carboxyl, amino, hydroxyl, thiol, and the like. In one embodiment, the support is optically transparent.

As used herein, "specifically hybridizes", "specific hybridization" refers to hybridization which occurs when two nucleic acid sequences are substantially complementary (at least about 65% complementary over a stretch of at least 14 to 25 nucleotides, preferably at least about 75% complementary, more preferably at least about 90% complementary). See Kanehisa, M., 1984, *Nucleic acids Res.*, 12:203, incorporated herein by reference. As a result, it is expected that a certain degree of mismatch is tolerated. Such mismatch may be small, such as a mono-, di- or tri-nucleotide. Alternatively, a region of mismatch can encompass loops, which are defined as regions in which there exists a mismatch in an uninterrupted series of four or more nucleotides. Numerous factors influence the efficiency and selectivity of hybridization of two nucleic acids, for example, the hybridization of a nucleic acid member on an array to a target nucleic acid sequence. These factors include nucleic acid member length, nucleotide sequence and/or composition, hybridization temperature, buffer composition and potential for steric hindrance in the region to which the nucleic acid member is required to hybridize. A positive correlation exists between the nucleic acid length and both the efficiency and accuracy with which a nucleic acid will anneal to a target sequence. In particular, longer sequences have a higher melting temperature ($T_M$) than do shorter ones, and are less likely to be repeated within a given target sequence, thereby minimizing promiscuous hybridization. Hybridization temperature varies inversely with nucleic acid member annealing efficiency. Similarly the concentration of organic solvents, e.g., formamide, in a hybridization mixture varies inversely with annealing efficiency, while increases in salt concentration in the hybridization mixture facilitate annealing. Under stringent annealing conditions, longer nucleic acids, hybridize more efficiently than do shorter ones, which are sufficient under more permissive conditions.

As herein used, the term "standard stringent conditions" means hybridization will occur only if there is at least 95% and preferably, at least 97% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). The degree of stringency of washing can be varied by changing the temperature, pH, ionic strength, divalent cation concentration, volume and duration of the washing. For example, the stringency of hybridization may be varied by conducting the hybridization at varying temperatures below the melting temperatures of the probes. The melting temperature of the probe may be calculated using the following formulas:

For oligonucleotide probes, between 14 and 70 nucleotides in length, the melting temperature (Tm) in degrees Celcius may be calculated using the formula: $Tm=81.5+16.6(\log [Na+])+0.41(\text{fraction } G+C)-(600/N)$ where N is the length of the oligonucleotide.

For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

If the hybridization is carried out in a solution containing formamide, the melting temperature may be calculated using the equation $Tm=81.5+16.6(\log [Na+])+0.41(\text{fraction } G+C)-(0.63\% \text{ formamide})-(600/N)$, where N is the length of the probe.

For example, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide.

As used herein, the term "significant match", when referring to nucleic acid sequences, means that two nucleic acid sequences exhibit at least 65% identity, at least 70%, at least 75%, at least 80%, at least 85%, and preferably, at least 90% identity, using comparison methods well known in the art (i.e., Altschul, S. F. et al., 1997, *Nucl. Acids Res.*, 25:3389-3402; Schäffer, A. A. et al., 1999, *Bioinformatics* 15: 1000-1011). As used herein, "significant match" encompasses non-contiguous or scattered identical nucleotides so long as the sequences exhibit at least 65%, and preferably, at least 70%, at least 75%, at least 80%, at least 85%, and preferably, at least 90% identity, when maximally aligned using alignment methods routine in the art.

As used herein, the term "synergistic" refers to a combination of a compound identified using one of the methods described herein, and another therapy (e.g., agent), which is more effective than the additive effects of the therapies. Preferably, such other therapy has been or is currently being to prevent, treat, manage or ameliorate schizophrenia and/or bipolar disorder or a symptom thereof. A synergistic effect of a combination of therapies (e.g., prophylactic or therapeutic agents) permits the use of lower dosages of one or more of the therapies and/or less frequent administration of said therapies to a subject with schizophrenia or bipolar disorder. The ability to utilize lower dosages of a therapy (e.g., a prophylactic or therapeutic agent) and/or to administer said therapy less frequently reduces the toxicity associated with the administration of said agent to a subject without reducing the efficacy of said therapies in the prevention, treatment, management or amelioration of schizophrenia or bipolar disorder. In addition, a synergistic effect can result in improved efficacy of therapies (e.g., agents) in the prevention, treatment, management or amelioration of schizophrenia or bipolar disorder. Finally, a synergistic effect of a combination of therapies (e.g., prophylactic or therapeutic agents) may avoid or reduce adverse or unwanted side effects associated with the use of either therapy alone.

As used herein, a "therapeutic agent" or "agent" refers to a compound that increases or decreases the expression of a polynucleotide or polypeptide sequences that are differentially expressed in a tissue or blood sample from an individual having schizophrenia or bipolar disorder. The invention provides for a "therapeutic agent" that 1) prevents the onset of episodes of schizophrenia and/or bipolar disorder; 2) reduces, delays, or eliminates advancement of episodes or severity of schizophrenia and/or bipolar disorder and/or 3) restores one or more expression profiles of one or more disease-indicative nucleic acids or polypeptides of a patient to a profile more similar to that of a normal individual when administered to a patient.

As used herein, the terms "therapeutic agent" and "therapeutic agents" refer to any compound(s) which can be used in the treatment, management or amelioration of schizophrenia and/or bipolar disorder or one or more symptoms and/or episodes thereof. In a specific embodiment, the term "therapeutic agent" refers to a compound that increases or decreases the expression of a polynucleotide or polypeptide sequence that is differentially expressed in a brain cell or brain cell line. The invention provides for a "therapeutic agent" that 1) prevents the onset schizophrenia and/or bipolar disorder or episodes thereof; 2) reduces, delays, or eliminates schizophrenia and/or bipolar disorder symptoms and/or episodes 3) reduces, delays, or eliminates schizophrenia and/or bipolar disorder progression; and/or 4) restores one or more expression profiles of one or more disease-indicative nucleic acids or proteins of a patient to a profile more similar to that of a normal individual when administered to a patient. In certain embodiments, the term "therapeutic agent" refers to a compound identified in the screening assays described herein. In other embodiments, the term "therapeutic agent" refers to an agent other than a compound identified in the screening assays described herein which is known to be useful for, or has been or is currently being used to treat, manage or ameliorate schizophrenia and/or bipolar disorder or one or more symptoms and/or episodes thereof.

As used herein, the term "therapeutically effective amount" refers to that amount of a therapy (e.g., a therapeutic agent) sufficient to result in the amelioration of schizophrenia and/or bipolar disorder or one or more symptoms and/or episodes thereof, prevent advancement of schizophrenia and/or bipolar disorder and/or episodes thereof, cause regression of schizophrenia and/or bipolar disorder and/or episodes thereof, or to enhance or improve the therapeutic effect(s) of another therapy (e.g., therapeutic agent). In a specific embodiment, a therapeutically effective amount refers to the amount of a therapy (e.g., a therapeutic agent) that modulates gene expression of the products of the biomarkers of the inventions. Preferably, a therapeutically effective amount of a therapy (e.g., a therapeutic agent) modulates gene expression of the products of the biomarkers of the invention at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control therapeutic agent such as phosphate buffered saline ("PBS").

As used herein, the terms "treat", "treatment" and "treating" refer to the reduction or amelioration of the progression, severity and/or duration of episodes and/or symptoms of therapeutic agent resulting from the administration of one or more compounds identified in accordance the methods of the invention, or a combination of one or more compounds identified in accordance with the invention and another therapy.

As used herein, a "tissue nucleic acid sample", refers to nucleic acids derived from tissue, preferably brain tissue. Preferably, a tissue nucleic acid sample is total RNA, mRNA or is a nucleic acid corresponding to RNA, for example, cDNA. A tissue nucleic acid sample can also include a PCR product derived from total RNA, mRNA or cDNA.

5.2 Summary

The practice of the present invention employs in part conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference in their entireties.

The invention as disclosed herein identifies biomarkers and biomarker combinations as well as a method of identifying said combinations from blood useful in diagnosing schizophrenia and/or bipolar disorder. In order to use these biomarkers, the invention teaches the measurement of expression of the RNA and/or the protein products of these biomarkers. The invention further discloses the oligonucleotides, cDNA, DNA, RNA, PCR products, synthetic DNA, synthetic RNA, or other combinations of modified nucleotides that specifically and/or selectively hybridize to the RNA products of the biomarkers of the invention allowing measurement of the expression of the RNA products of the biomarkers. The invention further discloses proteins, peptides, antibodies, ligands that specifically or selectively bind to the protein products of the biomarkers of the invention allowing measurement of the expression of the protein products of the invention and kits containing these polypeptides and/or polynucleotides.

The measuring of the expression of the RNA product of the biomarkers and combination of biomarkers of the invention, can be done by using those polynucleotides which are specific and/or selective for the RNA products of the biomarkers of the invention to quantitate the expression of the RNA product. In a specific embodiment of the invention, the polynucleotides which are specific and/or selective for the RNA products are probes or primers. In one embodiment, these polynucleotides are in the form of nucleic acid probes which can be spotted onto an array to measure RNA from the blood of an individual to be diagnosed. In another embodiment, commercial arrays can be used to measure the expression of the RNA product and the invention teaches which combination of genes to analyze. In yet another embodiment, the polynucleotides which are specific and/or selective for the RNA products of the biomarkers of the invention are used in the form of probes and primers in techniques such as quantitative real-time RT PCR, using for example SYBR®Green, or using TaqMan® or Molecular Beacon techniques, where the polynucleotides used are used in the form of a forward primer, a reverse primer, a TaqMan labelled probe or a Molecular Beacon labelled probe. The invention also teaches, in one embodiment, a method of identifying useful combinations of biomarkers by generating classifiers said classifiers able to differentiate as between (a) schizophrenia and non schizophrenia (b) bipolar disorder and non bipolar disorder and (c) schizophrenia and bipolar disorder; or (d) schizophrenia, bipolar disorder and non schizophrenia or non bipolar disorder using one or more of the biomarkers disclosed herein. The classifiers generated are particularly useful, in one embodiment to be used as a means to diagnosis. Classifiers which are able to differentiate as between (a) schizophrenia and non schizophrenia (b) bipolar disorder and non bipolar disorder and (c) schizophrenia and bipolar disorder; (d) schizophrenia, bipolar disorder and normal are generated by measuring the level of expression of the RNA products and/or the protein products of the invention and using the data resulting from said measurement for input into a mathematical model. Classifiers can be evaluated to determine the best combinations of biomarkers of the invention and appropriate weightings to be accorded to said biomarkers, so as to best classify as between two or more of the phenotypes schizophrenia, bipolar disorder or normal of a reference population. Note that it is not necessary that the same method used to generate the classifier as is used to diagnose the test individual.

The invention further contemplates the use of proteins or polypeptides as disclosed herein and would be known by a person skilled in the art to measure the protein products of the biomarkers of the invention. Techniques known to persons skilled in the art (for example, techniques such as Western Blotting, Immunoprecipitation, ELISAs, protein microarray analysis and the like) can then be used to measure the level of protein products corresponding to the biomarkers of the invention. As would be understood to a person skilled in the art, the measure of the level of expression of the protein products of the biomarkers of the invention requires a protein which specifically and/or selectively binds to one or more of the protein products corresponding to each biomarker of the invention. Data representative of the level of expression of the protein products of the biomarker of the invention can then be input into the model used to identify the combination in order to determine a diagnosis as defined by the model. In a preferred embodiment, the same method is used to generate the expression data used to generate the mathematical model as is used to diagnose the test individual.

The invention further contemplates the use of a combination of proteins or polypeptides in combination with polynucleotides so as to measure one or more products of the biomarkers of the invention.

The invention further contemplates a composition comprising a collection of two or more isolated polynucleotides, said polynucleotides which selectively hybridize to at least two biomarkers of the invention, wherein the biomarkers are selected from the group consisting of the genes: adenylosuccinate synthase (ADSS); apolipoprotein B mRNA editing enzyme, catalytic polypeptide-like 3B (APOBEC3B); ataxia telangiectasia mutated (includes complementation groups A, C and D) (ATM); Charcot-Leyden crystal protein (CLC); C-terminal binding protein 1 (CTBP1); chemokine (C-X-C motif) ligand 1 (melanoma growth stimulating activity, alpha) (CXCL1); death associated transcription factor 1 (DATF1); S100 calcium binding protein A9 (calgranulin B) (S100A9), and as set out in Table 1, and wherein the composition is used to measure the level of expression of said biomarker.

The invention further contemplates a composition comprising a collection of two or more isolated polynucleotides which bind selectively to the RNA products of at least two biomarkers, wherein the biomarkers are selected from the group consisting of the genes: adenylosuccinate synthase (ADSS); apolipoprotein B mRNA editing enzyme, catalytic polypeptide-like 3B (APOBEC3B); ataxia telangiectasia mutated (includes complementation groups A, C and D) (ATM); Charcot-Leyden crystal protein (CLC); C-terminal binding protein 1 (CTBP1); chemokine (C-X-C motif) ligand 1 (melanoma growth stimulating activity, alpha) (CXCL1); death associated transcription factor 1 (DATF1); S100 calcium binding protein A9 (calgranulin B) (S100A9), as set out in Table 1. A further aspect of this embodiment encompasses polynucleotides are useful in quantitative RT-PCR (QRT-PCR) of one or two or more of these biomarkers.

The invention further contemplates a composition comprising a collection of two or more isolated proteins which bind selectively to the protein products of at least two biomarkers, wherein the biomarkers are selected from the group consisting of the genes: adenylosuccinate synthase (ADSS); apolipoprotein B mRNA editing enzyme, catalytic polypeptide-like 3B (APOBEC3B); ataxia telangiectasia mutated (includes complementation groups A, C and D) (ATM); Charcot-Leyden crystal protein (CLC); C-terminal binding protein 1 (CTBP1); chemokine (C-X-C motif) ligand 1 (melanoma growth stimulating activity, alpha) (CXCL1); death associated transcription factor 1 (DATF1); S100 calcium binding protein A9 (calgranulin B) (S100A9), as set out in Table 1.

The invention further contemplates a composition comprising a collection of two or more isolated polynucleotides which bind selectively to the RNA products of one or more biomarkers, wherein the biomarkers are selected from the group consisting of the genes: adenylosuccinate synthase (ADSS); death associated transcription factor 1 (DATF1); as listed in Table 3.

The invention further contemplates a composition comprising a collection of one or more isolated proteins, which bind selectively to the protein products of one or more biomarkers, wherein the biomarkers are selected from the group consisting of the genes: adenylosuccinate synthase (ADSS); death associated transcription factor 1 (DATF1); as set out in Table 3.

The invention further contemplates a composition comprising a collection of isolated polynucleotides which bind selectively to the RNA products of biomarkers, wherein the biomarkers are selected from the group of genes: adenylosuccinate synthase (ADSS); death associated transcription factor 1 (DATF1); as set out in Table 3.

The invention further contemplates a composition comprising a collection of two or more isolated polynucleotides which bind selectively to the RNA products of at least one biomarker, wherein the biomarkers are selected from the group as set out in Table 4.

The invention further contemplates a composition comprising a collection of two or more isolated polynucleotides which bind selectively to the RNA products of at least one biomarker, wherein the biomarkers are selected from the group as set out in Table 5.

The invention further contemplates a composition comprising a collection of one or more isolated proteins which bind selectively to the protein products of at least one biomarker, wherein the biomarkers are selected from the group as set out in Table 4.

The invention further contemplates a composition comprising a collection of one or more isolated proteins which bind selectively to the protein products of at least one biomarker, wherein the biomarkers are selected from the group as set out in Table 5.

The invention further contemplates embodiments of any one of the compositions of the invention, wherein the referenced isolated proteins of said compositions are ligands, and/or wherein the ligands are antibodies. In one aspect, these antibodies are monoclonal antibodies.

The invention further contemplates a composition comprising any of the oligonucleotide compositions of the invention, wherein the isolated oligonucleotides are single or double stranded RNA, and/or wherein the isolated polynucleotides are single or double stranded DNA.

The invention further contemplates a method of diagnosing or prognosing schizophrenia in an individual, comprising the steps of:

a) determining the level of one or more RNA transcripts expressed in blood obtained from said individual, wherein said one or more RNA transcripts corresponds to said one or more biomarkers of Table 3, and b) comparing the level of each of said one or more RNA transcripts in said blood according to step a) with the level of each of said one or more RNA transcripts in blood from one or more individuals not having schizophrenia, wherein detecting differential expression of each of said one or more RNA transcripts in the comparison of step b) is indicative of schizophrenia in the individual of step a).

The invention further contemplates a method of diagnosing or prognosing bipolar disorder in an individual, comprising the steps of:

a) determining the level of one or more RNA transcripts expressed in blood obtained from said individual, wherein said one or more RNA transcripts corresponds to said one or more biomarkers of Table 4, and b) comparing the level of each of said one or more RNA transcripts in said blood according to step a) with the level of each of said one or more RNA transcripts in blood from one or more individuals not having bipolar disorder, wherein detecting differential expression of each of said one or more RNA transcripts in the comparison of step b) is indicative of bipolar disorder in the individual of step a).

The invention further contemplates a method of diagnosing or prognosing and individual as having either bipolar disorder or schizophrenia, comprising the steps of:

a) determining the level of one or more RNA transcripts expressed in blood obtained from said individual, wherein said one or more RNA transcripts corresponds to said one or more biomarkers of Table 5, and b) comparing the level of each of said one or more RNA transcripts in said blood according to step a) with the level of each of said one or more RNA transcripts in blood from one or more individuals having schizophrenia, wherein detecting differential expression of each of said one or more RNA transcripts in the comparison of step b) is indicative of bipolar disorder in the individual of step a).

The invention further contemplates a method of diagnosing or prognosing and individual as having either bipolar disorder or schizophrenia, comprising the steps of:

a) determining the level of one or more RNA transcripts expressed in blood obtained from said individual, wherein said one or more RNA transcripts corresponds to said one or more biomarkers of Table 5, and b) comparing the level of each of said one or more RNA transcripts in said blood according to step a) with the level of each of said one or more RNA transcripts in blood from one or more individuals having bipolar disorder, wherein detecting differential expression of each of said one or more RNA transcripts in the comparison of step b) is indicative of schizophrenia in the individual of step a).

The invention further contemplates a method of diagnosing or prognosing schizophrenia in an individual, comprising the steps of:

a) determining the level of two or more RNA transcripts expressed in blood obtained from said individual, wherein said two or more RNA transcripts corresponds to said one or more biomarkers of Table 1 and b) comparing the level of each of said two or more RNA transcripts in said blood according to step a) with the level of each of said two or more RNA transcripts in blood from one or more individuals having schizophrenia, c) comparing the level of each of said two or more RNA transcripts in said blood according to step a) with the level of each of said two or more RNA transcripts in blood from one or more individuals not having schizophrenia, d) determining whether the level of said two or more RNA transcripts of step a) classify with the levels of said transcripts in step b) as compared with levels of said transcripts in step c), wherein said determination is indicative of said individual of step a) having schizophrenia.

The invention further contemplates a method of diagnosing or prognosing bipolar disorder in an individual, comprising the steps of:

a) determining the level of two or more RNA transcripts expressed in blood obtained from said individual, wherein said two or more RNA transcripts corresponds to said two or more biomarkers of Table 1 and b) comparing the level of each of said two or more RNA transcripts in said blood according to step a) with the level of each of said two or more RNA transcripts in blood from one or more individuals having bipolar disorder, c) comparing the level of each of said two or more RNA transcripts in said blood according to step a) with the level of each of said two or more RNA transcripts in blood from one or more individuals not having bipolar disorder, d) determining whether the level of said two or more RNA transcripts of step a) classify with the levels of said transcripts in step b) as compared with levels of said transcripts in step c), wherein said determination is indicative of said individual of step a) having bipolar disorder.

The invention further contemplates a method of diagnosing or prognosing an individual as having bipolar disorder or schizophrenia, comprising the steps of:

a) determining the level of two or more RNA transcripts expressed in blood obtained from said individual, wherein said two or more RNA transcripts corresponds to said two or more biomarkers of Table 1 and b) comparing the level of each of said two or more RNA transcripts in said blood according to step a) with the level of each of said two or more RNA transcripts in blood from one or more individuals having bipolar disorder, c) comparing the level of each of said two or more RNA transcripts in said blood according to step a) with the level of each of said two or more RNA transcripts in blood from one or more individuals having schizophrenia, d) determining whether the level of said two or more RNA transcripts of step a) classify with the levels of said transcripts in step b) as compared with levels of said transcripts in step c), wherein said determination is indicative of said individual of step a) having bipolar disorder.

The invention further contemplates a method of diagnosing or prognosing schizophrenia in an individual, comprising the steps of:

a) determining the level of one or more RNA transcripts expressed in blood obtained from said individual, wherein said one or more RNA transcripts corresponds to said one or more biomarkers of Table 1 and b) using the results from step (a) in combination with a classifier so as to determine a diagnosis with respect to schizophrenia.

The invention further contemplates a method of diagnosing or prognosing bipolar disorder in an individual, comprising the steps of:

a) determining the level of one or more RNA transcripts expressed in blood obtained from said individual, wherein said one or more RNA transcripts corresponds to said one or more biomarkers of Table 1 and b) using the results from step (a) in combination with a classifier so as to determine a diagnosis with respect to bipolar disorder.

The invention further contemplates that any of the methods of the invention comprising a blood sample, that in these methods said blood sample consists of whole blood, and/or consists of a drop of blood, and/or consists of blood that has been lysed.

The invention further contemplates that any of the methods of the invention comprising a blood sample, that in these methods there comprises a further step of isolating RNA from said blood samples.

The invention further contemplates the instantly disclosed methods wherein the referenced step of determining the level of each of said one or more RNA transcripts comprises quantitative RT-PCR (QRT-PCR), wherein said one or more transcripts are from step a) and/or step b) of the above instantly disclosed methods. The invention further contemplates the instantly disclosed methods wherein the referenced QRT-PCR utilizes primers which hybridize to said one or more transcripts or the complement thereof, wherein said one or more transcripts are from step a) and/or step b) of the above disclosed methods.

The invention further contemplates that any of the methods of the invention which comprises one or more steps of determining the level of each of said one or more RNA transcripts, comprises quantitative RT-PCR (QRT-PCR). In one aspect, the said one or more transcripts are from step a) and/or step b) of the instant methods. In a further embodiment of these methods, said QRT-PCR utilizes primers which hybridize to said one or more transcripts or the complement thereof, wherein said one or more transcripts are from Tables 1-6.

The invention further contemplates that any of the methods of the invention comprising primers, said primers are 15-25 nucleotides in length.

The invention further contemplates that any of the methods of the invention comprising one or more steps of determining the level of each of said one or more RNA transcripts, the step of determining the level of each of said one or more RNA transcripts comprises hybridizing a first plurality of isolated nucleic acid molecules that correspond to said one or more transcripts, to an array comprising a second plurality of isolated nucleic acid molecules. In an aspect of these embodied methods, the first plurality of isolated nucleic acid molecules comprises RNA, DNA, cDNA, PCR products or ESTs. In an aspect of these embodied methods, the array comprises a plurality of isolated nucleic acid molecules comprising RNA, DNA, cDNA, PCR products or ESTs. In an aspect of these embodied methods, the second plurality of isolated nucleic acid molecules on said array comprises polynucleotides corresponding to one or more of the biomarkers of Table 1.

The invention further contemplates a kit for diagnosing or prognosing schizophrenia comprising:

a) at least two sets of biomarker specific priming means wherein each set of biomarker specific priming means produces double stranded DNA complementary to a unique biomarker selected from Table 1; wherein each first priming means of said sets contains a sequence which can selectively hybridize to RNA, cDNA or an EST complementary to one of said biomarkers to create an extension product and each said second priming means of said sets is capable of selectively hybridizing to said extension product;

b) an enzyme with reverse transcriptase activity;

c) an enzyme with thermostable DNA polymerase activity, and d) a labeling means;

wherein each of said primer sets is used to detect the quantitative expression levels of said biomarker in a test subject.

The invention further contemplates a kit for diagnosing or prognosing bipolar disorder comprising:

a) at least two sets of biomarker specific priming means wherein each set of biomarker specific priming means produces double stranded DNA complementary to a unique biomarker selected from Table 1; wherein each first priming means of said sets contains a sequence which can selectively hybridize to RNA, cDNA or an EST complementary to one of said biomarkers to create an extension product and each said second priming means of said sets is capable of selectively hybridizing to said extension product;

b) an enzyme with reverse transcriptase activity;

c) an enzyme with thermostable DNA polymerase activity, and d) a labeling means;

wherein each said primer set is used to detect the quantitative expression levels of a biomarker in a test subject.

The invention further contemplates a method of diagnosing or prognosing schizophrenia in an individual, comprising the steps of:

a) determining the level of two or more proteins expressed in blood obtained from said individual, wherein said two or more proteins are encoded by two or more biomarkers of Table 1, and b) comparing the level of each of said two or more proteins in said blood according to step a) with the level of each of said two or more proteins in blood from one or more individuals having schizophrenia, c) comparing the level of each of said two or more proteins in said blood according to step a) with the level of each of said two or more proteins in blood from one or more individuals not having schizophrenia, d) determining whether the level of said two or more proteins of step a) classify with the levels of said proteins in step b) as compared with levels of said proteins in step c), wherein said determination is indicative of said individual of step a) having schizophrenia.

The invention further contemplates a method of diagnosing or prognosing bipolar disorder in an individual, comprising the steps of:

a) determining the level of two or more proteins expressed in blood obtained from said individual, wherein said two or more proteins are encoded by two or more biomarkers of Table 1, and b) comparing the level of each of said two or more proteins in said blood according to step a) with the level of each of said two or more proteins in blood from one or more individuals having bipolar disorder c) comparing the level of each of said two or more proteins in said blood according to step a) with the level of each of said two or more proteins in blood from one or more individuals not having bipolar disorder, d) determining whether the level of said two or more proteins of step a) classify with the levels of said proteins in step b) as compared with levels of said proteins in step c), wherein said determination is indicative of said individual of step a) having bipolar disorder.

The invention further contemplates a method of diagnosing or prognosing an individual with bipolar disorder as compared with schizophrenia, comprising the steps of:

a) determining the level of two or more proteins expressed in blood obtained from said individual, wherein said two or more proteins are encoded by two or more biomarkers of Table 1, and b) comparing the level of each of said two or more proteins in said blood according to step a) with the level of each of said two or more proteins in blood from one or more individuals having bipolar disorder c) comparing the level of each of said two or more proteins in said blood according to step a) with the level of each of said two or more proteins in blood from one or more individuals having schizophrenia, d) determining whether the level of said two or more proteins of step a) classify with the levels of said proteins in step b) as compared with levels of said proteins in step c), wherein said determination is indicative of said individual of step a) having bipolar disorder.

The invention further contemplates a method of diagnosing or prognosing schizophrenia in an individual, comprising the steps of:

a) determining the level of two or more protein products expressed in blood obtained from said individual, wherein said two or more protein products corresponds to two or more biomarkers of Table 1 and b) using the results from step (a) in combination with a classifier designed to differentiate schizophrenia from non schizophrenia so as to determine a diagnosis with respect to schizophrenia.

The invention further contemplates a method of diagnosing or prognosing bipolar disorder in an individual, comprising the steps of:

a) determining the level of two or more protein products expressed in blood obtained from said individual, wherein said two or more protein products corresponds to two or more biomarkers of Table 1 and b) using the results from step (a) in combination with a classifier designed to differentiate bipolar disorder from non bipolar disorder so as to determine a diagnosis with respect to bipolar disorder.

The invention further contemplates a method of diagnosing or prognosing and individual as having bipolar disorder or schizophrenial, comprising the steps of:

a) determining the level of two or more protein products expressed in blood obtained from said individual, wherein said two or more protein products corresponds to two or more biomarkers of Table 1 and b) using the results from step (a) in combination with a classifier designed to differentiate bipolar disorder from schizophrenia so as to determine a diagnosis with respect to bipolar disorder or schizophrenia.

The invention further contemplates that in any method of the invention which comprises one or more steps of determining the level of each of said one or more proteins, that the step of determining the level of each of said one or more proteins comprises the use of two or more antibodies, wherein each of said two or more antibodies is specific for a protein product of a biomarker listed in Table 1. In an aspect of these methods, it is contemplated that the one or more antibodies is selected from the group consisting of a monoclonal antibody, fv. scfv, dab, fd, fab, and fab'2.

The invention further contemplates a method of developing a classifier useful for diagnosing schizophrenia, said method comprising:

(a) measuring the level of expression of the products of the biomarkers identified in Table 1 in a training population wherein said training population is comprised of two subgroups, a first subgroup diagnosed as having schizophrenia and said second subgroup diagnosed as not having schizophrenia.

(b) apply one or more mathematical models to the levels of expression of step (a) to develop one or more classifiers which differentiate between said first subgroup and said second subgroup. In one aspect of this invention, this method further comprises the step of evaluating one or more of said classifiers of step (b) for the classifier's ability to properly characterize each individual of the training population. In one aspect of this invention, this method further comprises the step of evaluating one or more of said classifiers of step (b) for the classifier's ability to properly characterize one or more individuals of a population which is not the training population. In one aspect of this invention, this method further comprises the step of evaluating one or more of said classifiers of step (b) for the classifier's ability to properly characterize one or more individuals of a population which is not the training population.

The invention further contemplates a method of developing a classifier useful for diagnosing bipolar disorder, said method comprising:

(a) measuring the level of expression of the products of the biomarkers identified in Table 1 in a training population wherein said training population is comprised of two subgroups, a first subgroup diagnosed as having bipolar disorder and said second subgroup diagnosed as not having bipolar disorder.

(b) apply one or more mathematical models to the levels of expression of step (a) to develop one or more classifiers which differentiate between said first subgroup and said second subgroup. In one aspect of this invention, this method further comprises the step of evaluating one or more of said classifiers of step (b) for the classifier's ability to properly characterize each individual of the training population. In one aspect of this invention, this method further comprises the step of evaluating one or more of said classifiers of step (b) for the classifier's ability to properly characterize one or more individuals of a population which is not the training population. In one aspect of this invention, this method further comprises the step of evaluating one or more of said classifiers of step (b) for the classifier's ability to properly characterize one or more individuals of a population which is not the training population.

The invention further contemplates a method of developing a classifier useful for diagnosing bipolar disorder or schizophrenia, said method comprising:

(a) measuring the level of expression of the products of the biomarkers identified in Table 1 in a training population wherein said training population is comprised of two subgroups, a first subgroup diagnosed as having bipolar disorder and said second subgroup diagnosed as having schizophrenia.

(b) apply one or more mathematical models to the levels of expression of step (a) to develop one or more classifiers which differentiate between said first subgroup and said second subgroup. In one aspect of this invention, this method further comprises the step of evaluating one or more of said classifiers of step (b) for the classifier's ability to properly characterize each individual of the training population. In one aspect of this invention, this method further comprises the step of evaluating one or more of said classifiers of step (b) for the classifier's ability to properly characterize one or more individuals of a population which is not the training population. In one aspect of this invention, this method further comprises the step of evaluating one or more of said classifiers of step (b) for the classifier's ability to properly characterize one or more individuals of a population which is not the training population.

The invention further contemplates the instantly disclosed methods which further comprises the step of evaluating one or more of said classifiers of step (b) for the classifier's ability to properly characterize one or more individuals of a population which is not the training population.

5.3 Samples For Use in the Invention

Unless otherwise indicated herein, blood samples obtained from any subject may be used in accordance with the methods of the invention. Examples of subjects from which such a sample may be obtained and utilized in accordance with the methods of the invention include, but are not limited to, asymptomatic subjects, subjects manifesting or exhibiting 1, 2, 3, 4 or more symptoms of schizophrenia and/or bipolar disorder, subjects clinically diagnosed as having schizophrenia and/or bipolar disorder, subjects predisposed to schizophrenia and/or bipolar disorder (e.g., subjects with a family history of schizophrenia and/or bipolar disorder, subjects with a genetic predisposition to schizophrenia and/or bipolar disorder, subjects suspected of having schizophrenia and/or bipolar disorder, subjects undergoing therapy for schizophrenia and/or bipolar disorder, subjects with schizophrenia and/or bipolar disorder and at least one other condition (e.g., subjects with 2, 3, 4, 5 or more conditions), subjects not undergoing treatment for schizophrenia and/or bipolar disorder, subjects determined by a medical practitioner (e.g., a physician) to be healthy or schizophrenia or bipolar disorder-free (i.e., normal), subjects that have been cured of schizophrenia and/or bipolar disorder, subjects that are managing their schizophrenia and/or bipolar disorder, and subjects that have not been diagnosed with schizophrenia and/or bipolar disorder.

In a further embodiment, the subject from which a sample may be obtained is a test individual wherein it is unknown whether the person has schizophrenia or bipolar disorder, and/or it is unknown what degree of schizophrenia or bipolar disorder the test individual might have, if any.

5.3.1. Blood

In one aspect of the invention, a sample of blood is obtained from a subject according to methods well known in the art. A sample of blood may be obtained from a subject, for example a subject having schizophrenia, having bipolar disorder or not having schizophrenia or bipolar disorder. In some embodiments, a drop of blood is collected from a simple pin prick made in the skin of a subject. Blood may be drawn from a subject from any part of the body (e.g., a finger, a hand, a wrist, an arm, a leg, a foot, an ankle, a stomach, and a neck) using techniques known to one of skill in the art, in particular methods of phlebotomy known in the art.

The amount of blood collected will vary depending upon the site of collection, the amount required for a method of the invention, and the comfort of the subject. However, an advantage of one embodiment of the present invention is that the amount of blood required to implement the methods of the present invention can be so small that more invasive procedures are not required to obtain the sample. For example, in some embodiments, all that is required is a drop of blood. This drop of blood can be obtained, for example, from a simple pinprick. In some embodiments, any amount of blood is collected that is sufficient to detect the expression of one, two, three, four, five, six, seven or all of the genes in Table 1. As such, in some embodiments, the amount of blood that is collected is 1 μl or less, 0.5 μl or less, 0.1 μl or less, or 0.01 μl or less. However, the present invention is not limited to such embodiments. In some embodiments more blood is available and in some embodiments, more blood can be used to effect the methods of the present invention. As such, in various specific embodiments, 0.001 ml, 0.005 ml, 0.01 ml, 0.05 ml, 0.1 ml, 0.15 ml, 0.2 ml, 0.25 ml, 0.5 ml, 0.75 ml, 1 ml, 1.5 ml, 2 ml, 3 ml, 4 ml, 5 ml, 10 ml, 15 ml or more of blood is collected from a subject. In another embodiment, 0.001 ml to 15 ml, 0.01 ml to 10 ml, 0.1 ml to 10 ml, 0.1 ml to 5 ml, 1 to 5 ml of blood is collected from a subject.

In some embodiments of the present invention, blood is stored within a K3/EDTA tube. In another embodiment, one can utilize tubes for storing blood which contain stabilizing agents such as disclosed in U.S. Pat. No. 6,617,170 (which is incorporated herein by reference). In another embodiment the PAXgene™ blood RNA system:provided by PreAnalytiX, a Qiagen/BD company may be used to collect blood. In yet another embodiment, the Tempus™ blood RNA collection tubes, offered by Applied Biosystems may be used. Tempus™ collection tubes provide a closed evacuated plastic tube containing RNA stabilizing reagent for whole blood collection.

The blood collected is preferably utilized immediately or within 1 hour, 2 hours, 3 hours, 4 hours, 5 hours or 6 hours or is optionally stored at temperatures such as 4° C., or at −20° C. prior to use in accordance with the methods of the invention. In some embodiments, a portion of the blood sample is used in accordance with the invention at a first instance of time whereas one or more remaining portions of the blood sample (or fractions thereof) are stored for a period of time for later use. For longer term storage, storage methods well known in the art, such as storage at cryo temperatures (e.g. below −60° C.) can be used. In some embodiments, in addition to storage of the blood or instead of storage of the blood, plasma, serum, isolated nucleic acid or proteins are stored for a period of time for later use in accordance with methods known in the art.

In one aspect, whole blood is obtained from an individual according to the methods of phlebotomy well known in the art. Whole blood includes blood which can be used directly, and includes blood wherein the serum or plasma has been removed and the RNA or mRNA from the remaining blood sample has been isolated in accordance with methods well known in the art (e.g., using, preferably, gentle centrifugation at 300 to 800×g for 5 to 10 minutes). In a specific embodiment, whole blood (i.e., unfractionated blood) obtained from a subject is mixed with lysing buffer (e.g., Lysis Buffer (IL): 0.6 g EDTA; 1.0 g $KHCO_2$, 8.2 g $NH_4Cl$ adjusted to pH 7.4 (using NaOH)), the sample is centrifuged and the cell pellet retained, and RNA or mRNA extracted in accordance with methods known in the art ("lysed blood") (see for example Sambrook et al.). The use of unfractionated whole blood is preferred since it avoids the costly and time-consuming process to separate out the cell types within the blood (Kimoto, 1998, Mol. Gen. Genet. 258:233-239; Chelly J et al., 1989, Proc. Nat. Acad. Sci. USA 86:2617-2621; Chelly J et al., 1988, Nature 333:858-860).

In some embodiments of the present invention, whole blood collected from a subject is fractionated (i.e., separated into components). In specific embodiments of the present invention, blood cells are separated from whole blood collected from a subject using techniques known in the art. For example, blood collected from a subject can be subjected to Ficoll-Hypaque (Pharmacia) gradient centrifugation. Such centrifugation separates erythrocytes (red blood cells) from various types of nucleated cells and from plasma. In particular, Ficoll-Hypaque gradient centrifugation is useful to isolate peripheral blood leukocytes (PBLs) which can be used in accordance with the methods of the invention.

By way of example but not limitation, macrophages can be obtained as follows. Mononuclear cells are isolated from peripheral blood of a subject, by syringe removal of blood followed by Ficoll-Hypaque gradient centrifugation. Tissue culture dishes are pre-coated with the subject's own serum or with AB+human serum and incubated at 37° C. for one hour. Non-adherent cells are removed by pipetting. Cold (4° C.) 1 mM EDTA in phosphate-buffered saline is added to the adherent cells left in the dish and the dishes are left at room temperature for fifteen minutes. The cells are harvested, washed with RPMI buffer and suspended in RPMI buffer. Increased numbers of macrophages can be obtained by incubating at 37° C. with macrophage-colony stimulating factor (M-CSF). Antibodies against macrophage specific surface markers, such as Mac-1, can be labeled by conjugation of an affinity compound to such molecules to facilitate detection and separation of macrophages. Affinity compounds that can be used include but are not limited to biotin, photobiotin, fluorescein isothiocyante (FITC), or phycoerythrin (PE), or other compounds known in the art. Cells retaining labeled antibodies are then separated from cells that do not bind such antibodies by techniques known in the art such as, but not limited to, various cell sorting methods, affinity chromatography, and panning.

Blood cells can be sorted using a using a fluorescence activated cell sorter (FACS). Fluorescence activated cell sorting (FACS) is a known method for separating particles, including cells, based on the fluorescent properties of the particles. See, for example, Kamarch, 1987, Methods Enzymol 151:150-165. Laser excitation of fluorescent moieties in the individual particles results in a small electrical charge allowing electromagnetic separation of positive and negative particles from a mixture. An antibody or ligand used to detect a blood cell antigenic determinant present on the cell surface of particular blood cells is labeled with a fluorochrome, such as FITC or phycoerythrin. The cells are incubated with the fluorescently labeled antibody or ligand for a time period sufficient to allow the labeled antibody or ligand to bind to cells. The cells are processed through the cell sorter, allowing separation of the cells of interest from other cells. FACS sorted particles can be directly deposited into individual wells of microtiter plates to facilitate separation.

Magnetic beads can be also used to separate blood cells in some embodiments of the present invention. For example, blood cells can be sorted using a using a magnetic activated cell sorting (MACS) technique, a method for separating particles based on their ability to bind magnetic beads (0.5-100 m diameter). A variety of useful modifications can be performed on the magnetic microspheres, including covalent addition of an antibody which specifically recognizes a cell-solid phase surface molecule or hapten. A magnetic field is then applied, to physically manipulate the selected beads. In a specific embodiment, antibodies to a blood cell surface marker are coupled to magnetic beads. The beads are then mixed with the blood cell culture to allow binding. Cells are then passed through a magnetic field to separate out cells having the blood cell surface markers of interest. These cells can then be isolated.

In some embodiments, the surface of a culture dish may be coated with antibodies, and used to separate blood cells by a method called panning. Separate dishes can be coated with antibody specific to particular blood cells. Cells can be added first to a dish coated with blood cell specific antibodies of interest. After thorough rinsing, the cells left bound to the dish will be cells that express the blood cell markers of interest. Examples of cell surface antigenic determinants or markers include, but are not limited to, CD2 for T lymphocytes and natural killer cells, CD3 for T lymphocytes, CD11a for leukocytes, CD28 for T lymphocytes, CD19 for B lymphocytes, CD20 for B lymphocytes, CD21 for B lymphocytes, CD22 for B lymphocytes, CD23 for B lymphocytes, CD29 for leukocytes, CD14 for monocytes, CD41 for platelets, CD61 for platelets, CD66 for granulocytes, CD67 for granulocytes and CD68 for monocytes and macrophages.

Whole blood can be separated into cell types such as leukocytes, platelets, erythrocytes, etc. and such cell types can be used in accordance with the methods of the invention. Leukocytes can be further separated into granulocytes and agranulocytes using standard techniques and such cells can be used in accordance with the methods of the invention. Granulocytes can be separated into cell types such as neutrophils, eosinophils, and basophils using standard techniques and such cells can be used in accordance with the methods of the invention. Agranulocytes can be separated into lymphocytes (e.g., T lymphocytes and B lymphocytes) and monocytes using standard techniques and such cells can be used in accordance with the methods of the invention. T lymphocytes can be separated from B lymphocytes and helper T cells separated from cytotoxic T cells using standard techniques and such cells can be used in accordance with the methods of the invention. Separated blood cells (e.g., leukocytes) can be frozen by standard techniques prior to use in the present methods.

A blood sample that is useful according to the invention is in an amount that is sufficient for the detection of one or more nucleic acid or amino acid sequences according to the invention. In a specific embodiment, a blood sample useful according to the invention is in an amount ranging from 1 μl to 100 ml, preferably 10 μl to 50 ml, more preferably 10 μl to 25 ml and most preferably 10 μl to 1 ml.

5.4 RNA Preparation

In one aspect of the invention, RNA is isolated from an individual in order to measure the RNA products of the biomarkers of the invention. RNA is isolated from blood samples from individuals diagnosed with schizophrenia or diagnoised with bipolar disorder, individuals not having schizophrenia or bipolar disorder, or test individuals.

Preferably, RNA is isolated from blood by the following protocol. Lysis Buffer is added to blood sample in a ratio of 3 parts Lysis Buffer to 1 part blood (Lysis Buffer (IL) 0.6 g EDTA; 1.0 g $KHCO_2$, 8.2 g $NH_4Cl$ adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol® (GIBCO/BRL) in a ratio of approximately 6 ml of TRIzol® for every 10 ml of the original blood sample and vortexed well. Samples are left for 5 minutes at room temperature. RNA is extracted using 1.2 ml of chloroform per 1 ml of TRIzol®. Sample is centrifuged at 12,000×g for 5 minutes at 4° C. and upper layer is collected. To upper layer, isopropanol is added in ratio of 0.5 ml per 1 ml of TRIzol®. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

Purity and integrity of RNA can be assessed by absorbance at 260/280 nm and agarose gel electrophoresis followed by inspection under ultraviolet light. Preferably RNA integrity is assessed using more sensitive techniques such as the Agilent 2100 Bioanalyzer 6000 RNA Nano Chip.

5.5 Biomarkers of the Invention

In one aspect, the invention provides biomarkers and biomarker combinations wherein the measure of the level of expression of the product or products of said biomarkers is indicative of the existence of schizophrenia and/or bipolar disorder.

Table 1 provides a list of the gene names and the associated locus link ID for the biomarkers of the invention wherein the measure of the level of expression of the biomarkers, in combination can be used to diagnose an individual as having schizophrenia and/or bipolar disorder and/or differentiate between schizophrenia and bipolar disorder.

TABLE 1

| Alternative Gene Symbols | HGNC_Symbol | Assigned Label | Locus Link ID | Rta_Transcript A notation |
|---|---|---|---|---|
| ADSS | | ADS | 159 | adenylosuccinate synthase |
| APOBEC3B | | APO | 9582 | apolipoprotein B mRNA editing enzyme, catalytic polypeptide-like 3B |
| ATM | | ATM | 472 | ataxia telangiectasia mutated (includes complementation groups A, C and D) |
| CLC | | CLC | 1178 | Charcot-Leyden crystal protein |
| CTBP1 | | CTB | 1487 | C-terminal binding protein 1 |
| CXCL1 | | CXC | 2919 | chemokine (C-X-C motif) ligand 1 (melanoma growth stimulating activity, alpha) |
| DATF1 | | DAT | 11083 | death associated transcription factor 1 |
| S100A9 | | S10 | 6280 | S100 calcium binding protein A9 (calgranulin B) |

The genes of Table 1 are identified on the basis of their name, Hugo Gene name and locus link ID.

As would be understood by a person skilled in the art, the locus link ID can be used to determine the sequence of all the RNA transcripts and all of the proteins which correspond to the biomarkers of the invention.

Table 2 provides, in one embodiment of the invention, is a selection of the sequences of the RNA products corresponding to the biomarkers of the invention as disclosed in Table 1 and whose sequences can be used to measure the level of expression of the biomarkers of the invention using those techniques known to a person skilled in the art. Table 2 also provides, in one embodiment of the invention, sequences of the proteins corresponding to the biomarkers of the invention which can be measured to determine the level of expression of the biomarkers of the invention.

TABLE 2

| HGNC_Gene Symbols | Alternative Symbol | Ref Sequence Gene Accession Number | Ref Sequence Protein Accession Number | Locus Link ID | Rta_Transcript A notation |
|---|---|---|---|---|---|
| ADSS | | NM_001126 | NP_001117 | 159 | adenylosuccinate synthase |
| APOBEC3B | | NM_004900 | NP_004891 | 9582 | apolipoprotein B mRNA editing enzyme, catalytic polypeptide-like 3B |
| ATM | | NM_000051 | NP_000042 | 472 | ataxia telangiectasia mutated (includes complementation groups A, C and D) |
| ATM | | NM_138292 | NP_612149 | 472 | ataxia telangiectasia mutated (includes complementation groups A, C and D) transcript variant 2, mRNA. |
| ATM | | NM_138293 | NP_612150 | 472 | ataxia telangiectasia mutated protein isoform 3 |
| CLC | | NM_001828 | NP_001819 | 1178 | Charcot-Leyden crystal protein |
| CTBP1 | | NM_001328 | NP_001319 | 1487 | C-terminal binding protein 1 |
| CXCL1 | | NM_001511 | NP_001502 | 2919 | Chemokine (C—X—C motif) ligand 1 (melanoma growth stimulating activity, alpha) |
| DATF1 | | NM_022105 | NP_071388 | 11083 | death associated transcription factor 1 isoform a |

TABLE 2-continued

| HGNC_Gene Symbols | Alternative Symbol | Ref Sequence Gene Accession Number | Ref Sequence Protein Accession Number | Locus Link ID | Rta_Transcript A notation |
|---|---|---|---|---|---|
| DATF1 | | NM_080796 | NP_542986 | 11083 | death associated transcription factor 1, isoform a |
| DATF1 | | NM_080797 | NP_542987 | 11083 | death associated transcription factor 1 isoform b |
| S100A9 | | NM_002965 | NP_002956 | 6280 | S100 calcium binding protein A9 (calgranulin B) |

Table 3 provides a list of the gene names and the associated locus link ID for the biomarkers of the invention which have been newly identified as a biomarker which individually differentiates as between schizophrenia and non schizophrenia individuals. Genes are identified on the basis of their name, Hugo Gene name and locus link ID. Genes have been selected which demonstrate a p value of <0.2

TABLE 3

| Alternative Gene Symbols | HGNC_Symbol | Assigned Label | Locus Link ID | Rta_Transcript A notation |
|---|---|---|---|---|
| ADSS | | ADS | 159 | adenylosuccinate synthase |
| DATF1 | | DAT | 11083 | death associated transcription factor 1 |

Table 4 provides a list of the gene names and the associated locus link ID for the biomarkers of the invention which have been newly identified as a biomarker which individually can differentiate as between individuals with bipolar disorder or not having bipolar disorder. Genes have been selected which demonstrate differential expression with a p value of <0.2. Table 4 identifies the genes on the basis of their name, Hugo Gene name and locus link ID.

TABLE 4

| Alternative Gene Symbols | HGNC_Symbol | Assigned Label | Locus Link ID | Rta_Transcript A notation |
|---|---|---|---|---|
| ADSS | | ADS | 159 | adenylosuccinate synthase |
| APOBEC3B | | APO | 9582 | apolipoprotein B mRNA editing enzyme, catalytic polypeptide-like 3B |
| CXCL1 | | CXC | 2919 | chemokine (C—X—C motif) ligand 1 (melanoma growth stimulating activity, alpha) |

Table 5 provides a list of the gene names and the associated locus link ID for the biomarkers of the invention which have been newly identified as a biomarker which individually differentiates as between individuals with bipolar disorder or individuals having schizophrenia. Table 5 identifies the genes on the basis of their name, Hugo Gene name and locus link ID.

TABLE 5

| Alternative Gene Symbols | HGNC_Symbol | Assigned Label | Locus Link ID | Rta_Transcript A notation |
|---|---|---|---|---|
| ADSS | | ADS | 159 | adenylosuccinate synthase |
| DATF1 | | DAT | 11083 | death associated transcription factor 1 |

The invention thus encompasses the use of those methods known to a person skilled in the art to measure the expression of these biomarkers and combinations of biomarkers for each of the purposes outlined above.

5.6 Combinations oF Biomarkers

In one embodiment, combinations of biomarkers of the present invention includes any combination of 2, 3, 4, 5, 6, 7, or all 8, of the biomarkers listed in Table 1. For instance, the number of possible combinations of a subset m of n genes in any of the Tables above is described in Feller, *Intro to Probability Theory*, Third Edition, volume 1, 1968, ed. J. Wiley, using the general formula:

$$m!/(n)!(m-n)!$$

In one embodiment of the invention, where n is 2 and m is 8, the number of combinations of markers selected from Table 1 is:

$$\begin{aligned}\frac{8!}{2!(8-2)!} &= \frac{8\times7\times6\times5\times4\times3\times2\times1}{(2\times1)(6\times5\times4\times3\times2\times1)} \\ &= 40320/1440 \\ &= 28\end{aligned}$$

unique two-gene combinations. The measurement of the gene expression of each of these two-gene combinations can independently be used to determine whether a patient has schizophrenia. In another specific embodiment in which m is 8 and n is three, there are 8!/3!(8−3)! unique three-gene combinations. Each of these unique three-gene combinations can independently serve as a model for determining whether a patient has schizophrenia and/or bipolar disorder.

5.7 Identifying Species of Useful Combinations of Biomarkers by Generating Classifiers The invention further provides a means of selecting those combinations of biomarkers from Table 1 particularly useful for each of the following (a) differentiating between schizophrenia and non schizophrenia individuals (b) differentiating between bipolar disorder and non bipolar disorder individuals (c) differentiating between schizophrenia individuals and individuals with bipolar disorder. The invention further provides a method of evaluating the combinations identified for each of the utilities described above and using the classifiers identified to diagnose an individual as having schizophrenia or having bipolar disorder.

In order to identify useful combinations of biomarkers and generate classifiers, a mathematical model of the invention is used to test the possible combinations of the biomarkers of the invention for each combination's ability to separate as between the two (e.g. binary models such as logistic regression) or more (e.g. models such as neural networks) phenotypic traits of a training population used for input into the model. The phenotypic traits of the training population used for input into the model are phenotypic traits for use in (a) differentiating between schizophrenia and non schizophrenia individuals (b) differentiating between bipolar disorder and non bipolar disorder individuals (c) differentiating between schizophrenia individuals and individuals with bipolar disorder or (d) differentiating between schizophrenia, bipolar disorder and individuals having neither schizophrenia or bipolar disorder. The phenotypic traits of the training population used for input into the mathematical model, and the model used, will determine the utility of the combinations generated by the model for use as a means of diagnosing schizophrenia and/or bipolar disorder. The result of the choice of phenotypic traits of the training population used for entry into the mathematical model is described more thoroughly below.

The mathematical model generated can be subsequently evaluated by determining the ability of the model to correctly call each individual for one of the two (or more) phenotypic traits of the population used for input into the model. In a preferred embodiment, the individuals of the training population used to derive the model are different from the individuals of the training population used to test the model. As would be understood by a person skilled in the art, this allows one to predict the ability of the combinations as to their ability to properly characterize an individual whose phenotypic characterization is unknown.

The data which is input into the mathematical model can be any data which is representative of the expression level of the product of the biomarkers being evaluated. Mathematical models useful in accordance with the invention include those using both supervised or unsupervised learning. In a preferred embodiment of the invention, the mathematical model chosen uses supervised learning in conjunction with a "training population" to evaluate each of the possible combination of biomarkers of the invention. In one embodiment of the invention, the mathematical model used is selected from the following: a regression model, a logistic regression model, a neural network, a clustering model, principal component analysis, nearest neighbour classifier analysis, linear discriminant analysis, quadratic discriminant analysis, a support vector machine, a decision tree, a genetic algorithm, classifier optimization using bagging, classifier optimization using boosting, classifier optimization using the Random Subspace Method, a projection pursuit, genetic programming and weighted voting. In a preferred embodiment, a logistic regression model is used. In another preferred embodiment, a neural network model is used.

The results of applying a mathematical model of the invention to the data will generate one or more classifiers using one or more biomarkers. Classifiers generated can be used to diagnosis an unknown or test individual. As would be understood by a person skilled in the art, the use of the classifier depends upon the phenotypes of the population used to generate the classifier and the mathematical model used. In one embodiment, the diagnosis result from equations generated by logistic regression to answer one of the following questions: (a) does an individual have schizophrenia, (b) does an individual have bipolar disorder or (c) is an individual "normal". In yet another embodiment of the invention, the answer to any of the questions above may be an answer of non determinable.

In one preferred embodiment of the invention, each classifier is evaluated for its ability to properly characterize each individual of the training population using those methods known to a person skilled in the art. For example one can evaluate the classifier using cross validation, Leave One out Cross Validation (LOOCV), n-fold cross validation, jackknife analysis using standard statistical methods as disclosed. In an even more preferred embodiment of the invention, each classifier is evaluated for its ability to properly characterize those individuals of the training population which were not used to generate the classifier.

In one embodiment, the method used to evaluate the classifier for its ability to properly characterize each individual of the training population is a method which evaluates the models sensitivity (TPF, true positive fraction) and 1-specificity (TNF, true negative fraction). In a preferred embodiment, the method used to test the model is Receiver Operating Characteristic ("ROC") which provides several parameters to evaluate both the sensitivity and specificity of the diagnostic result of the equation generated. In a particularly preferred embodiment, the ROC area (area under the curve) is used to evaluate the equations. A ROC area greater than 0.5, 0.6, 0.7, 0.8, 0.9 is preferred. A perfect ROC area score of 1.0 indicates with both 100% sensitivity and 100% specificity.

As would be understood by a person skilled in the art, the utility of the combinations and equations determined by a mathematical model will depend upon the phenotypes of the populations used to generate the data for input into the model. Examples of specific embodiments are described more thoroughly herein.

5.8 Populations for Input into the Mathematical Models

Populations used for input should be chosen so as to result in statistically significant resulting biomarker combinations. In some embodiments, the reference or training population includes between 10 and 30 subjects. In another embodiment the reference population contains between 30-50 subjects. In still other embodiments, the reference population includes two or more populations each containing between 50 and 100, 100 and 500, between 500 and 1000, or more than 1000 subjects. The reference population includes two or more subpopulations. In a preferred embodiment, the phenotypic characteristics of the subpopulations are similar but for the diagnosis with respect to schizophrenia and/or bipolar disorder, for example the subpopulations are of a similar age and sex. It is also preferred that the subpopulations are of roughly equivalent numbers.

For example, for populations for input into a binary mathematical model to identify those biomarkers which are useful in diagnosing an individual as having schizophrenia, or not having schizophrenia, the reference population is comprised of individuals having schizophrenia (the first subpopulation), and individuals not have schizophrenia (the second subpopulation). For purposes of characterizing the subpopulations as having or not having schizophrenia, any verified method can be used. Preferably only those individuals whose diagnoses are certain are utilized as part of the reference population.

In another embodiment, populations for input into a binary mathematical model to identify those biomarkers which are useful in diagnosing an individual as having bipolar disorder, or not having bipolar disorder are used. The reference population is comprised of individuals having bipolar disorder (the first subpopulation), and individuals not have bipolar disorder (the second subpopulation). For purposes of characterizing the subpopulations as having or not having bipolar disorder, any verified method can be used. Preferably only those individuals whose diagnoses are certain are utilized as part of the reference population.

In another embodiment, populations for input into a binary mathematical model to identify those biomarkers which are useful in diagnosing an individual as having either bipolar disorder, or having schizophrenia are used. The reference population is comprised of individuals having bipolar disorder (the first subpopulation), and individuals having schizophrenia (the second subpopulation). For purposes of characterizing the subpopulations having schizophrenia or bipolar disorder, any verified method can be used. Preferably only those individuals whose diagnoses are certain are utilized as part of the reference population.

In another embodiment, populations for input into a non-binary mathematical model is used to identify those biomarkers which are useful in diagnosing an individual as having either bipolar disorder, or having schizophrenia. The reference population is comprised of individuals having bipolar disorder (the first subpopulation), individuals having schizophrenia (the second subpopulation) and individuals having neither (the third subpopulation). For purposes of characterizing the subpopulations having schizophrenia or bipolar disorder, or neither any verified method can be used. Preferably only those individuals whose diagnosis are certain are utilized as part of the reference population.

5.9 Data for Input into the Mathematical Models to Identify Classifiers for Diagnosis Data for input into the mathematical models is data representative of the level of gene expression of the products of the biomarkers of the invention. As such the data is the measure of the products of the biomarkers of the invention including either mRNA and/or protein expression.

In one embodiment of the invention, the RNA products of the biomarkers of the invention which are measured are the population of RNA products including the mRNA, and all of the spliced variants of the mRNA. In another embodiment of the invention the products measured are the mRNA expressed in blood. In yet another embodiment of the invention, the products measured one or more specific spliced variants of the mRNA which are expressed in blood. In yet another embodiment of the invention, the products measured are the RNA products listed in Table 2.

Protein products of the biomarkers of the invention are also included within the scope of the invention. To practice the invention, measurement of the protein products of the biomarkers of the invention can be used for purposes of diagnosis. More particularly, measurement of those populations of protein products of the biomarkers which are differentially expressed during schizophrenia and/or bipolar disorder are useful for purposes of diagnosis and are encompassed herein.

In one embodiment of the invention the protein products are those translated from the biomarkers listed in Table 1. In another embodiment, the protein products are those which are expressed in blood. In yet another embodiment of the invention, the protein products are those corresponding to the proteins listed in Table 2.

In yet another embodiment, data reflective of the level of expression of a combination of protein products and RNA products of the biomarkers are used. As would be understood by a person skilled in the art, other combinations of input data can be utilized to generate classifiers useful in accordance with the invention.

5.10 Mathematical Models

Regression Models

In some embodiments the expression data for some or all of the biomarkers identified in the present invention are used in a regression model, preferably a logistic regression model so as to identify classifiers useful in diagnosing schizophrenia and/or bipolar disorder. The regression model is used to test various combinations of two or more of the biomarkers identified in Table 1 to generate classifiers. In the case of regression models, the classifiers which result are in the form of equations where the data representing the expression of each of the biomarkers in the equation is multiplied by a weighted coefficient as generated by the regression model. The classifiers generated can be used to analyze expression data from a test individual and provide a diagnosis. In general, the multiple regression equation of interest can be written $$Y=\alpha+\beta_1X_1+\beta_2X_2+\ldots+\beta_kX_k+\epsilon$$

where Y, the dependent variable, is present (when Y is positive) or absent (when Y is negative) of the biological feature (e.g., absence or presence of schizophrenia and/or bipolar disorder) associated with the first subgroup. This model says that the dependent variable Y depends on k explanatory variables (the measured characteristic values for the k select genes (e.g. the biomarkers) from subjects in the first and second subgroups in the reference population), plus an error term that encompasses various unspecified omitted factors. In the above-identified model, the parameter $\beta_1$ gauges the effect of the first explanatory variable $X_1$ on the dependent variable Y (e.g. a weighting factor), holding the other explanatory variables constant. Similarly, $\beta_2$ gives the effect of the explanatory variable $X_2$ on Y, holding the remaining explanatory variables constant.

The logistic regression model is a non-linear transformation of the linear regression. The logistic regression model is termed the "logit" model and can be expressed as $$ln[p/(1-p)]=\alpha+\beta_1X_1+\beta_2X_2+\ldots+\beta_kX_k+\epsilon \text{ or}$$

$$[p/(1-p)]=\exp^{\alpha}\exp^{\beta_1X_1}\exp^{\beta_2X_2}\times\ldots\times\exp^{\beta_kX_k}\exp^{\epsilon}$$

where, where $\alpha$ and $\epsilon$ are constants ln is the natural logarithm, $\log^{exp}$, where exp=2.71828 . . .

p is the probability that the event Y occurs, p(Y=1), p/(1−p) is the "odds ratio", ln[p/(1−p)] is the log odds ratio, or "logit", and all other components of the model are the same as the general regression equation described above. It will be appreciated by those of skill in the art that the term for $\alpha$ and $\epsilon$ can be folded into the same constant. Indeed, in preferred embodiments, a single term is used to represent $\alpha$ and $\epsilon$. The "logistic" distribution is an S-shaped distribution function. The logit distribution constrains the estimated probabilities (p) to lie between 0 and 1.

In some embodiments of the present invention, the logistic regression model is fit by maximum likelihood estimation (MLE). In other words, the coefficients (e.g., $\alpha, \beta_1, \beta_2, \ldots$) are determined by maximum likelihood. A likelihood is a conditional probability (e.g., P(Y|X), the probability of Y given X). The likelihood function (L) measures the probability of observing the particular set of dependent variable values ($Y_1, Y_2, \ldots, Y_n$) that occur in the sample data set. It is written as the probability of the product of the dependent variables:

$$L=\text{Prob}(Y_1*Y_2***Y_n)$$

The higher the likelihood function, the higher the probability of observing the Ys in the sample. MLE involves finding the coefficients ($\alpha, \beta_1, \beta_2, \ldots$) that makes the log of the likelihood function (LL<0) as large as possible or −2 times the log of the likelihood function (−2LL) as small as possible. In MLE, some initial estimates of the parameters $\alpha, \beta_1, \beta_2, \ldots$ are made. Then the likelihood of the data given these parameter estimates is computed. The parameter estimates are improved the likelihood of the data is recalculated. This process is repeated until the parameter estimates do not change much (for example, a change of less than 0.01 or 0.001 in the probability). Examples of logistic regression and fitting logistic logistic regression models are found in Hastie, *The Elements of Statistical Learning*, Springer, N.Y., 2001, pp. 95-100 which is incorporated herein in its entirety.

Neural Networks

In another embodiment, the expression measured for each of the biomarkers of the present invention can be used to train a neural network. A neural network is a two-stage regression or classification model. A neural network can be binary or non binary. A neural network has a layered structure that includes a layer of input units (and the bias) connected by a layer of weights to a layer of output units. For regression, the layer of output units typically includes just one output unit. However, neural networks can handle multiple quantitative responses in a seamless fashion. As such a neural network can be applied to allow identification of biomarkers which differentiate as between more than two populations. In one specific example, a neural network can be trained using expression data from the biomarkers in Table 1 to identify those combinations of biomarkers which are specific for schizophrenia as compared with not having schizophrenia. As a result, the trained neural network can be used to directly identify combination of biomarkers useful as schizophrenia diagnostic biomarkers. In some embodiments, the back-propagation neural network (see, for example Abdi, 1994, "A neural network primer", J. Biol System. 2, 247-283) containing a single hidden layer of ten neurons (ten hidden units) found in EasyNN-Plus version 4.0 g software package (Neural Planner Software Inc.) is used.

Neural networks are described in Duda et al., 2001, *Pattern Classification*, Second Edition, John Wiley & Sons, Inc., New York; and Hastie et al., 2001, *The Elements of Statistical Learning*, Springer-Verlag, New York which is incorporated herein in its entirety.

Other Mathematical Models

The pattern classification and statistical techniques described above are merely examples of the types of models that can be used to construct classifiers useful for diagnosing schizophrenia and/or bipolar disorder, for example clustering as described on pages 211-256 of Duda and Hart, *Pattern Classification and Scene Analysis*, 1973, John Wiley & Sons, Inc., New York, incorporated herein by reference in its entirety; Principal component analysis, (see for Jolliffe, 1986, *Principal Component* Analysis, Springer, N.Y., incorporated herein by reference); nearest neighbour classifier analysis, (see for example Duda, *Pattern Classification*, Second Edition, 2001, John Wiley & Sons, Inc; and Hastie, 2001, *The Elements of Statistical Learning*, Springer, N.Y.); linear discriminant analysis, (see for example Duda, *Pattern Classification*, Second Edition, 2001, John Wiley & Sons, Inc; and Hastie, 2001, *The Elements of Statistical Learning*, Springer, N.Y.; Venables & Ripley, 1997, *Modern Applied Statistics with s-plus*, Springer, N.Y.); Support Vector Machines (see, for example, Cristianini and Shawe-Taylor, 2000, *An Introduction to Support Vector Machines*, Cambridge University Press, Cambridge, Boser et al., 1992, "A training algorithm for optimal margin classifiers, in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York, incorporated herein by reference.)

5.8 Use of the Biomarkers of the Invention for Diagnosis

As would be understood by a person skilled in the art, the identification of one or more biomarkers can be used to allow the diagnosis of schizophrenia and/or bipolar disorder by measuring the expression of the products of the biomarkers (gene) in an individual to be diagnosed (the "test individual").

In one embodiment, the results from the test individual are compared with the a control wherein the control can be results from one or more individuals having schizophrenia and/or one or more individuals not having schizophrenia. In another embodiment the results from the test individual are compared with both a control population having bipolar disorder and a control population not having bipolar disorder.

In another embodiment, one can input expression data of the expression of the products of the biomarkers of the test individual into a classifier of the invention resulting in a determination of whether said test individual has schizophrenia or has bipolar disorder. In a preferred embodiment, one would use the same classifier used to generate the biomarkers as to diagnose an individual, but this is not necessary. Data representative of the RNA or protein products of the biomarkers of the invention is input into a classifier of the invention so as to determine a diagnosis. The data can be generated using any technique known to measure the level of expression of either the RNA and protein products of the biomarkers of the invention.

In one embodiment, use of the classifier results in a determination of whether the test individual has schizophrenia or does not have schizophrenia. For example, using logistic regression as the model, Y is used as a predictor of schizophrenia, where when Y>0 a person is diagnosed as having schizophrenia and where Y<0, a person is diagnosed as not having schizophrenia. In yet another embodiment, one can also include a third category of prediction wherein diagnosis is indeterminable. For example, one can determine the standard deviation inherent within the methodology used to measure gene expression of the biomarkers ($\delta$). If $Y<\delta$ but >0 or $Y>-\delta$ but <0, then the diagnosis is considered indeterminable.

5.11 Polynucleotides Used to Measure the Products of the Biomarkers of the Invention Polynucleotides capable of specifically or selectively binding to the RNA products of the biomarkers of the invention are used to measure the level of expression of the biomarkers. For example: oligonucleotides, cDNA, DNA, RNA, PCR products, synthetic DNA, synthetic RNA, or other combinations of naturally occurring or modified nucleotides which specifically and/or selectively hybridize to one or more of the RNA products of the biomarker of the invention are useful in accordance with the invention.

In a preferred embodiment, the oligonucleotides, cDNA, DNA, RNA, PCR products, synthetic DNA, synthetic RNA, or other combinations of naturally occurring or modified nucleotides oligonucleotides which both specifically and selectively hybridize to one or more of the RNA products of the biomarker of the invention are used.

5.12 Techniques to Measure the RNA Products of the Biomarkers of the Invention

5.12.1 Array Hybridization

In one embodiment of the invention, the polynucleotide used to measure the RNA products of the invention can be used as nucleic acid members stably associated with a support to comprise an array according to one aspect of the invention. The length of a nucleic acid member can range from 8 to 1000 nucleotides in length and are chosen so as to be specific for the RNA products of the biomarkers of the invention. In one embodiment, these members are selective for the RNA products of the biomarkers of the invention. The nucleic acid members may be single or double stranded, and/or may be oligonucleotides or PCR fragments amplified from cDNA. Preferably oligonucleotides are approximately 20-30 nucleotides in length. ESTs are preferably 100 to 600 nucleotides in length. It will be understood to a person skilled in the art that one can utilize portions of the expressed regions of the biomarkers of the invention as a probe on the array. More particularly oligonucleotides complementary to the genes of the invention and or cDNA or ESTs derived from the genes of the invention are useful. For oligonucleotide based arrays, the selection of oligonucleotides corresponding to the gene of interest which are useful as probes is well understood in the art. More particularly it is important to choose regions which will permit hybridization to the target nucleic acids. Factors such as the Tm of the oligonucleotide, the percent GC content, the degree of secondary structure and the length of nucleic acid are important factors. See for example U.S. Pat. No. 6,551,784.

Construction of a Nucleic Acid Array

In the subject methods, an array of nucleic acid members stably associated with the surface of a substantially support is contacted with a sample comprising target nucleic acids under hybridization conditions sufficient to produce a hybridization pattern of complementary nucleic acid members/target complexes in which one or more complementary nucleic acid members at unique positions on the array specifically hybridize to target nucleic acids. The identity of target nucleic acids which hybridize can be determined with reference to location of nucleic acid members on the array.

The nucleic acid members may be produced using established techniques such as polymerase chain reaction (PCR) and reverse transcription (RT). These methods are similar to those currently known in the art (see e.g., *PCR Strategies*, Michael A. Innis (Editor), et al. (1995) and PCR: *Introduction to Biotechniques Series*, C. R. Newton, A. Graham (1997)). Amplified nucleic acids are purified by methods well known in the art (e.g., column purification or alcohol precipitation). A nucleic acid is considered pure when it has been isolated so as to be substantially free of primers and incomplete products produced during the synthesis of the desired nucleic acid. Preferably, a purified nucleic acid will also be substantially free of contaminants which may hinder or otherwise mask the specific binding activity of the molecule.

An array, according to one aspect of the invention, comprises a plurality of nucleic acids attached to one surface of a support at a density exceeding 20 different nucleic acids/$cm^2$, wherein each of the nucleic acids is attached to the surface of the support in a non-identical pre-selected region (e.g. a microarray). Each associated sample on the array comprises a nucleic acid composition, of known identity, usually of known sequence, as described in greater detail below. Any conceivable substrate may be employed in the invention.

In one embodiment, the nucleic acid attached to the surface of the support is DNA. In a preferred embodiment, the nucleic acid attached to the surface of the support is cDNA or RNA. In another preferred embodiment, the nucleic acid attached to the surface of the support is cDNA synthesized by polymerase chain reaction (PCR). Preferably, a nucleic acid member in the array, according to the invention, is at least 10, 25 or 50 nucleotides in length. In one embodiment, a nucleic acid member is at least 150 nucleotides in length. Preferably, a nucleic acid member is less than 1000 nucleotides in length. More preferably, a nucleic acid member is less than 500 nucleotides in length.

In the arrays of the invention, the nucleic acid compositions are stably associated with the surface of a support, where the support may be a flexible or rigid support. By "stably associated" is meant that each nucleic acid member maintains a unique position relative to the support under hybridization and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the nucleic acids and a functional group present on the surface of the rigid support (e.g., —OH), where the functional group may be naturally occurring or present as a member of an introduced linking group, as described in greater detail below The amount of nucleic acid present in each composition will be sufficient to provide for adequate hybridization and detection of target nucleic acid sequences during the assay in which the array is employed. Generally, the amount of each nucleic acid member stably associated with the support of the array is at least about 0.001 ng, preferably at least about 0.02 ng and more preferably at least about 0.05 ng, where the amount may be as high as 1000 ng or higher, but will usually not exceed about 20 ng. Where the nucleic acid member is "spotted" onto the support in a spot comprising an overall circular dimension, the diameter of the "spot" will generally range from about 10 to 5,000 μm, usually from about 20 to 2,000 μm and more usually from about 100 to 200 μm.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key" gene of interest is expressed, but rather to provide other useful information, such as background or basal level of expression.

Other control nucleic acids are spotted on the array and used as target expression control nucleic acids and mismatch control nucleotides to monitor non-specific binding or cross-hybridization to a nucleic acid in the sample other than the target to which the probe is directed. Mismatch probes thus indicate whether a hybridization is specific or not. For example, if the target is present, the perfectly matched probes should be consistently brighter than the mismatched probes. In addition, if all control mismatches are present, the mismatch probes are used to detect a mutation.

Spotting Method

In one aspect, the invention provides for arrays where each nucleic acid member comprising the array is spotted onto a support.

Preferably, spotting is carried out as follows. PCR products (~40 ul) biomarkers of the invention, in the same 96-well tubes used for amplification, are precipitated with 4 ul (1/10 volume) of 3M sodium acetate (pH 5.2) and 100 ul (2.5 volumes) of ethanol and stored overnight at −20° C. They are then centrifuged at 3,300 rpm at 4° C. for 1 hour. The obtained pellets are washed with 50 ul ice-cold 70% ethanol and centrifuged again for 30 minutes. The pellets are then air-dried and resuspended well in 20 ul 3×SSC or in 50% dimethylsulfoxide (DMSO) overnight. The samples are then spotted, either singly or in duplicate, onto slides using a robotic GMS 417 or 427 arrayer (Affymetrix, Ca).

The boundaries of the spots on the microarray may be marked with a diamond scriber (as the spots become invisible after post-processing). The arrays are rehydrated by suspending the slides over a dish of warm particle free $ddH_2O$ for approximately one minute (the spots will swell slightly but will not run into each other) and snap-dried on a 70-80° C. inverted heating block for 3 seconds. Nucleic acid is then UV crosslinked to the slide (Stratagene, Stratalinker, 65 mJ—set display to "650" which is 650×100 uJ) or the array is baked at 80 C for two to four hours prior to hybridization. The arrays are placed in a slide rack. An empty slide chamber is prepared and filled with the following solution: 3.0 grams of succinic anhydride (Aldrich) was dissolved in 189 ml of 1-methyl-2-pyrrolidinone (rapid addition of reagent is crucial); immediately after the last flake of succinic anhydride is dissolved, −21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. $ddH_2O$ for 2 minutes, followed by plunging five times in 95% ethanol. The slides are then air dried by allowing excess ethanol to drip onto paper towels. The arrays are stored in the slide box at room temperature until use.

Numerous methods may be used for attachment of the nucleic acid members of the invention to the substrate (a process referred to as "spotting"). For example, nucleic acids are attached using the techniques of, for example U.S. Pat. No. 5,807,522, which is incorporated herein by reference, for teaching methods of polymer attachment.

Alternatively, spotting may be carried out using contact printing technology as is known in the art.

Use of a Microarray

Nucleic acid arrays according to the invention can be used to assay nucleic acids in a sample comprising one or more target nucleic acid sequences. The arrays of the subject invention find use in a variety of applications diagnosis of schizophrenia, screening for therapeutic targets and the like.

The arrays are also useful in broad scale expression screening for drug discovery and research, such as the effect of a particular active agent on the expression pattern of biomarkers of the invention, where such information is used to reveal drug efficacy and toxicity, environmental monitoring, disease research and the like.

Arrays can be made using at least one, more preferably a combination of these sequences, as a means of diagnosing schizophrenia.

The choice of a standard sample would be well understood by a person skilled in the art, and would include a sample complementary to RNA isolated from one or more normal individuals, wherein a normal individual is an individual not having schizophrenia or bipolar disorder.

Preparation of Nucleic Acid Sample for Hybridization to an Array

The samples for hybridization with the arrays according to the invention are preferably derived from total RNA from blood. In another embodiment, targets for the arrays are derived from mRNA from blood The nucleic acid sample is capable of binding to a nucleic acid member of complementary sequence through one or more types of chemical bonds, usually through complementary base pairing, usually through hydrogen bond formation.

As used herein, a "nucleic acid derived from an mRNA transcript: or a "nucleic acid corresponding to an mRNA" refers to a nucleic acid for which synthesis of the mRNA transcript or a sub-sequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from or correspond to the mRNA transcript and detection of such derived or corresponding products is indicative of or proportional to the presence and/or abundance of the original transcript in a sample. Thus, suitable nucleic acid samples include, but are not limited to, mRNA transcripts of a gene or genes, cDNA reverse transcribed from the mRNA, cRNA transcribed from the cDNA, DNA amplified from a gene or genes, RNA transcribed from amplified DNA, and the like. The nucleic acid samples used herein are preferably derived from blood. Nucleic acids can be single- or double-stranded DNA, RNA, or DNA-RNA hybrids synthesized from human blood using methods known in the art, for example, reverse transcription or PCR.

In the simplest embodiment, such a nucleic acid sample comprises total mRNA or a nucleic acid sample corresponding to mRNA (e.g., cDNA) isolated from blood samples. In another embodiment, total mRNA is isolated from a given sample using, for example, an acid guanidinium-phenol-chloroform extraction method and polyA+ mRNA is isolated by oligo dT column chromatography or by using (dT)n magnetic beads (see, e.g., Sambrook et al., *Molecular Cloning: A Laboratory Manual* (2nd ed.), Vols. 1-3, Cold Spring Harbor Laboratory, (1989), or Current Protocols in Molecular Biology, F. Ausubel et al., ed. Greene Publishing and Wiley-Interscience, New York (1987). In a preferred embodiment, total RNA is extracted using TRIzol® reagent (GIBCO/BRL, Invitrogen Life Technologies, Cat. No. 15596). Purity and integrity of RNA is assessed by absorbance at 260/280 nm and agarose gel electrophoresis followed by inspection under ultraviolet light.

In some embodiments, it is desirable to amplify the nucleic acid sample prior to hybridization, for example, when only limited amounts of sample can be used (e.g. drop of blood). One of skill in the art will appreciate that whatever amplification method is used, if a quantitative result is desired, care must be taken to use a method that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A Guide to Methods and Application*. Academic Press, Inc. San Diego, (1990)), ligase chain reaction (LCR) (see Wu and Wallace, 1989*, Genomics,* 4:560; Landegren, et al., 1988*, Science,* 241:1077 and Barringer, et al., 1990*, Gene,* 89:117, transcription amplification (Kwoh, et al., 1989*, Proc. Natl. Acad. Sci. USA,* 86: 1173), and self-sustained sequence replication (Guatelli, et al., 1990*, Proc. Nat. Acad. Sci. USA,* 87: 1874).

In a particularly preferred embodiment, the nucleic acid sample mRNA is reverse transcribed with a reverse transcriptase and a primer consisting of oligo dT and a sequence encoding the phage T7 promoter to provide single-stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro transcription are well known to those of skill in the art (see, e.g., Sambrook, supra.) and this particular method is described in detail by Van Gelder, et al., 1990*, Proc. Natl. Acad. Sci. USA,* 87: 1663-1667 who demonstrate that in vitro amplification according to this method preserves the relative frequencies of the various RNA transcripts. Moreover, Eberwine et al. *Proc. Natl. Acad. Sci. USA,* 89: 3010-3014 provide a protocol that uses two rounds of amplification via in vitro transcription to achieve greater than 106 fold amplification of the original starting material thereby permitting expression monitoring even where biological samples are limited.

Labeling of Nucleic Acid Sample or Nucleic Acid Probe.

Nucleic acid samples are labelled so as to allow detection of hybridization to an array of the invention. Any analytically detectable marker that is attached to or incorporated into a molecule may be used in the invention. An analytically detectable marker refers to any molecule, moiety or atom which is analytically detected and quantified.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^{3}$H, $^{125}$I, 35S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, the entireties of which are incorporated by reference herein.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

In a preferred embodiment, the fluorescent modifications are by cyanine dyes e.g. Cy-3/Cy-5 dUTP, Cy-3/Cy-5 dCTP (Amersham Pharmacia) or alexa dyes (Khan, et al., 1998*, Cancer Res.* 58:5009-5013).

In a preferred embodiment, the two Nucleic Acid Sample samples used for comparison are labeled with different fluorescent dyes which produce distinguishable detection signals, for example, nucleic acid samples made from normal brain cells are labeled with Cy5 and nucleic acid samples made from brain tissue cells are labeled with Cy3. The differently labeled target samples are hybridized to the same microarray simultaneously. In a preferred embodiment, the labeled nucleic acid samples are purified using methods known in the art, e.g., by ethanol purification or column purification.

In a preferred embodiment, the nucleic acid samples will include one or more control molecules which hybridize to control probes on the microarray to normalize signals generated from the microarray. Preferably, labeled normalization nucleic acid samples are nucleic acid sequences that are perfectly complementary to control oligonucleotides that are spotted onto the microarray as described above. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes, thereby normalizing the measurements.

Preferred normalization nucleic acid samples are selected to reflect the average length of the other nucleic acid samples present in the sample, however, they are selected to cover a range of lengths. The normalization control(s) also can be selected to reflect the (average) base composition of the other probes in the array, however, in a preferred embodiment, only one or a few normalization probes are used and they are selected such that they hybridize well (i.e., have no secondary structure and do not self hybridize) and do not match any nucleic acids on the array.

Normalization probes are localized at any position in the array or at multiple positions throughout the array to control for spatial variation in hybridization efficiency. In a preferred embodiment, normalization controls are located at the corners or edges of the array as well as in the middle.

Hybridization Conditions

Nucleic acid hybridization involves providing a nucleic acid sample under conditions where the sample and the complementary nucleic acid member can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The invention provides for hybridization conditions comprising the Dig hybridization mix (Boehringer); or formamide-based hybridization solutions, for example as described in Ausubel et al., supra and Sambrook et al. supra.

Methods of optimizing hybridization conditions are well known to those of skill in the art (see, e.g., *Laboratory Techniques in Biochemistry and Molecular Biology, Vol.* 24*: Hybridization With Nucleic acid Probes*, P. Tijssen, ed. Elsevier, N.Y., (1993)).

Following hybridization, non-hybridized labeled or unlabeled nucleic acid is removed from the support surface, conveniently by washing, thereby generating a pattern of hybridized target nucleic acid on the substrate surface. A variety of wash solutions are known to those of skill in the art and may be used. The resultant hybridization patterns of labeled, hybridized oligonucleotides and/or nucleic acids may be visualized or detected in a variety of ways, with the particular manner of detection being chosen based on the particular label of the test nucleic acid, where representative detection means include scintillation counting, autoradiography, fluorescence measurement, calorimetric measurement, light emission measurement and the like.

Image Acquisition and Data Analysis

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding to the signal emitted by a known number of end labeled target nucleic acids to obtain a count or absolute value of the copy number of each end-labeled target that is hybridized to a particular spot on the array in the hybridization pattern.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data is displayed as an image with the intensity in each region varying according to the binding affinity between associated oligonucleotides and/or nucleic acids and the test nucleic acids.

The following detection protocol is used for the simultaneous analysis of two samples to be compared, where each sample is labeled with a different fluorescent dye.

Each element of the microarray is scanned for the first fluorescent color. The intensity of the fluorescence at each array element is proportional to the expression level of that gene in the sample.

The scanning operation is repeated for the second fluorescent label. The ratio of the two fluorescent intensities provides a highly accurate and quantitative measurement of the relative gene expression level in the two samples.

In a preferred embodiment, fluorescence intensities of immobilized nucleic acid sequences were determined from images taken with a custom confocal microscope equipped with laser excitation sources and interference filters appropriate for the Cy3 and Cy5 fluors. Separate scans were taken for each fluor at a resolution of 225 $\mu m^2$ per pixel and 65,536 gray levels. Image segmentation to identify areas of hybridization, normalization of the intensities between the two fluor images, and calculation of the normalized mean fluorescent values at each target are as described (Khan, et al., 1998*, Cancer Res.* 58:5009-5013. Chen, et al., 1997*, Biomed. Optics* 2:364-374). Normalization between the images is used to adjust for the different efficiencies in labeling and detection with the two different fluors. This is achieved by equilibrating to a value of one the signal intensity ratio of a set of internal control genes spotted on the array.

In another preferred embodiment, the array is scanned in the Cy3 and Cy5 channels and stored as separate 16-bit TIFF images. The images are incorporated and analysed using software which includes a gridding process to capture the hybridization intensity data from each spot on the array. The fluorescence intensity and background-subtracted hybridization intensity of each spot is collected and a ratio of measured mean intensities of Cy5 to Cy3 is calculated. A linear regression approach is used for normalization and assumes that a scatter plot of the measured Cy5 versus Cy3 intensities should have a slope of one. The average of the ratios is calculated and used to rescale the data and adjust the slope to one. A ratio of expression not equal to 1 is used as an indication of differential gene expression.

In a particularly preferred embodiment, where it is desired to quantify the transcription level (and thereby expression) of one or more nucleic acid sequences in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear and still provide meaningful results. Thus, for example, an assay where a 5 fold difference in concentration of the sample mRNA results in a 3- to 6-fold difference in hybridization intensity is sufficient for most purposes. Where more precise quantification is required, appropriate controls are run to correct for variations introduced in sample preparation and hybridization as described herein. In addition, serial dilutions of "standard" mRNA sampels are used to prepare calibration curves according to methods well known to those of skill in the art. Of course, where simple detection of the presence or absence of a transcript is desired, no elaborate control or calibration is required.

For example, if an nucleic acid member on an array is not labeled after hybridization, this indicates that the gene comprising that nucleic acid member is not expressed in either sample. If a nucleic acid member is labeled with a single color, it indicates that a labeled gene was expressed only in one sample. The labeling of a nucleic acid member comprising an array with both colors indicates that the gene was expressed in both samples. Even genes expressed once per cell are detected (1 part in 100,000 sensitivity). A difference in expression intensity in the two samples being compared is indicative of differential expression, the ratio of the intensity in the two samples being not equal to 1.0, preferably less than 0.7 or greater than 1.2, more preferably less than 0.5 or greater than 1.5.

5.12.2 RT-PCR

In aspect of the invention, the level of the expression of the RNA products of the biomarkers of the invention can be measured by amplifying the RNA products of the biomarkers from a sample using reverse transcription (RT) in combination with the polymerase chain reaction (PCR). In accordance with one embodiment of the invention, the RT can be quantitative as would be understood to a person skilled in the art.

Total RNA, or mRNA from a sample is used as a template and a primer specific to the transcribed portion of a biomarker of the invention is used to initiate reverse transcription. Methods of reverse transcribing RNA into cDNA are well known and described in Sambrook et al., 1989, supra. Primer design can be accomplished utilizing commercially available software (e.g., Primer Designer 1.0, Scientific Sofware etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts.

The method of PCR is well known in the art. PCR, is performed as described in Mullis and Faloona, 1987, Methods Enzymol., 155: 335, which is incorporated herein by reference. PCR is performed using template DNA (at least lfg; more usefully, 1-1000 ng) and at least 25 μmol of oligonucleotide primers. A typical reaction mixture includes: 2 μl of DNA, 25 μmol of oligonucleotide primer, 2.5 μl of 10H PCR buffer 1 (Perkin-Elmer, Foster City, Calif.), 0.4 μl of 1.25 μM dNTP, 0.15 μl (or 2.5 units) of Taq DNA polymerase (Perkin Elmer, Foster City, Calif.) and deionized water to a total volume of 25 μl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

QRT-PCR (Quantitative RT-PCR), which is quantitative in nature, can also be performed to provide a quantitative measure of gene expression levels. In QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions can be performed in 96 well plates, 384 well plates and the like so that samples derived from many individuals are processed and measured simultaneously. The Taqman system has the additional advantage of not requiring gel electrophoresis and allows for quantification when used with a standard curve.

A second technique useful for detecting PCR products quantitatively without is to use an intercolating dye such as the commercially available QuantiTect SYBR Green PCR (Qiagen, Valencia Calif.). RT-PCR is performed using SYBR green as a fluorescent label which is incorporated into the PCR product during the PCR stage and produces a flourescense proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the flourescense increases giving a quantitative measurement of gene expression.

Additional techniques to quantitatively measure RNA expression include, but are not limited to, polymerase chain reaction, ligase chain reaction, Qbeta replicase (see, e.g., International Application No. PCT/US87/00880), isothermal amplification method (see, e.g., Walker et al. (1992) PNAS 89:382-396), strand displacement amplification (SDA), repair chain reaction, Asymmetric Quantitative PCR (see, e.g., U.S. Publication No. US200330134307A1) and the multiplex microsphere bead assay described in Fuja et al., 2004, Journal of Biotechnology 108:193-205.

The level of gene expression can be measured by amplifying RNA from a sample using transcription based amplification systems (TAS), including nucleic acid sequence amplification (NASBA) and 3SR. See, e.g., Kwoh et al (1989) PNAS USA 86:1173; International Publication No. WO 88/10315; and U.S. Pat. No. 6,329,179. In NASBA, the nucleic acids may be prepared for amplification using conventional phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques may be used to separate amplification products. For example, amplification products may be separated by agarose, agarose-acrylamide or polyacrylamide gel electrophoresis using conventional methods. See Sambrook et al., 1989. Several techniques for detecting PCR products quantitatively without electrophoresis may also be used according to the invention (see for example *PCR Protocols, A Guide to Methods and Applications*, Inis et al., Academic Press, Inc. N.Y., (1990)). For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982).

Another example of a separation methodology is done by covalently labeling the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by the Raggio Italgene company under the C-Track trade name.

Amplification products must be visualized in order to confirm amplification of the nucleic acid sequences of interest. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified nucleic acid sequence of interest. The probe preferably is conjugated to a chromophore but may be radiolabeled. In another embodiment, the probe is conjugated to a binding partner, such as an antibody or biotin, where the other member of the binding pair carries a detectable moiety.

In another embodiment, detection is by Southern blotting and hybridization with a labeled probe. The techniques involved in Southern blotting are well known to those of skill in the art and may be found in many standard books on molecular protocols. See Sambrook et al., 1989, supra. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

5.12.3 Nuclease Protection Assays

In another embodiment of the invention, Nuclease protection assays (including both ribonuclease protection assays and S1 nuclease assays) can be used to detect and quantitate the RNA products of the biomarkers of the invention. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

5.12.4 Northern Blots

A standard Northern blot assay can also be used to ascertain an RNA transcript size, identify alternatively spliced RNA transcripts, and the relative amounts of RNA products of the biomarker of the invention, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Non-limiting examples of isotopes include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

5.13 Techniques to Measure the Protein Products of the Biomarkers of the Invention

5.13.1 Antibody Based Methodologies

Standard techniques can also be utilized for determining the amount of the protein or proteins of interest present in a sample. For example, standard techniques can be employed using, e.g., immunoassays such as, for example, Western blot, immunoprecipitation followed by sodium dodecyl sulfate polyacrylamide gel electrophoresis (SDS-PAGE), immunocytochemistry, and the like to determine the amount of the protein or proteins of interest present in a sample. A preferred agent for detecting a protein of interest is an antibody capable of binding to a protein of interest, preferably an antibody with a detectable label.

For such detection methods, protein from the sample to be analyzed can easily be isolated using techniques which are well known to those of skill in the art. Protein isolation methods can, for example, be such as those described in Harlow and Lane (Harlow, E. and Lane, D., *Antibodies: A Laboratory Manual*, Cold Spring Harbor Laboratory Press, Cold Spring Harbor, N.Y. (1988)).

Preferred methods for the detection of the protein or proteins of interest involve their detection via interaction with a protein-specific antibody. For example, antibodies directed a protein of interest can be utilized as described herein. Antibodies can be generated utilizing standard techniques well known to those of skill in the art. See, e.g., Section 15.13.2 of this application and Section 5.2 of U.S. Publication No. 20040018200 for a more detailed discussion of such antibody generation techniques, which is incorporated herein by reference. Briefly, such antibodies can be polyclonal, or more preferably, monoclonal. An intact antibody, or an antibody fragment (e.g., Fab or $F(ab')_2$) can, for example, be used. Preferably, the antibody is a human or humanized antibody.

Table 5 is a table showing, in one embodiment of the invention, antibodies which are used to detect the proteins of the biomarkers of the invention.

TABLE 6

| Gene Symbol | Description | Commercial Reference | Scientific Reference | Related Antibodies Commercially Available |
|---|---|---|---|---|
| ADSS | adenylosuccinate synthase | | | |
| APOBEC3B | apolipoprotein B mRNA editing enzyme, catalytic polypeptide-like 3B | | | APOBEC1 (ADI Catologue # APOBEC1-1A); (SantaCruz Biotechnology; sc11738) |
| ATM | ataxia telangiectasia mutated (includes complementation groups A, C and D) | Ab2629 (AbCam ®) | | |
| CLC | Charcot-Leyden crystal protein | | Ultrastructural localization of the Charcot-Leyden crystal protein (lysophospholipase) to a distinct crystalloid-free granule population in mature human eosinophils AM Dvorak, L Letourneau, GR Login, PF Weller and SJ Ackerman American Society of Haemotology Vol 72 Issue 1 pg. 150. | |
| CTBP1 | C-terminal binding protein 1 | Ab14411 (Abcam ®) | | |

TABLE 6-continued

| Gene Symbol | Description | Commercial Reference | Scientific Reference | Related Antibodies Commercially Available |
|---|---|---|---|---|
| CXCL1 | chemokine (C—X—C motif) ligand 1 (melanoma growth stimulating activity, alpha) | Ab14026 (Abcam ®) | | |
| DATF1 | death associated transcription factor 1 | | | |
| S100A9 | S100 calcium binding protein A9 (calgranulin B) | CYT402 (Chemicon International) | | |

For example, antibodies, or fragments of antibodies, specific for a protein of interest can be used to quantitatively or qualitatively detect the presence of the protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a histological specimen (e.g., a biopsy specimen) from a patient, and applying thereto a labeled antibody thereto that is directed to a protein. The antibody (or fragment) is preferably applied by overlaying the labeled antibody (or fragment) onto a biological sample. Through the use of such a procedure, it is possible to determine not only the presence of the protein of interest, but also its distribution, its presence in cells (e.g., brain cells and lymphocytes) within the sample. A wide variety of well-known histological methods (such as staining procedures) can be utilized in order to achieve such in situ detection.

Immunoassays for a protein of interest typically comprise incubating a biological sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

For example, the biological sample can be brought in contact with and immobilized onto a solid phase support or carrier such as nitrocellulose, or other support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on support can then be detected by conventional means.

By "solid phase support or carrier" in the context of proteinaceous agents is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which a specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}I$, $^{131}I$, $^{35}S$ or $^{3}H$) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.13.2 Protein Arrays

Polypeptides which specifically and/or selectively bind to the protein products of the biomarkers of the invention can be immobilized on a protein array. The protein array can be used as a diagnostic tool, e.g., to screen individiual samples (such as isolated cells, blood, synovial fluid, sera, biopsies, and the like) for the presence of the polypeptides protein products of the biomarkers of the invention. The protein array can also include antibodies as well as other ligands, e.g., that bind to the polypeptides encoded by the biomarkers of the invention. Methods of producing polypeptide arrays are described, e.g., in De Wildt et al., 2000, Nature Biotech. 18:989-994; Lueking et al., 1999, Anal. Biochem. 270:103-111; Ge, 2000, Nuc. Acids Res. 28:e3; MacBeath and Schreiber, 2000, Science 289:1760-1763; International Publication Nos. WO 01/40803 and WO 99/51773A1; and U.S. Pat. No. 6,406,921. Polypeptides for the array can be spotted at high speed, e.g., using commercially available robotic apparatus, e.g., from Genetic MicroSystems and Affymetrix (Santa Clara, Calif., USA) or BioRobotics (Cambridge, UK). The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the polypeptide ligands can be grown on a filter in an arrayed format. Polypeptide production is induced, and the expressed antibodies are immobilized to the filter at the location of the cell. Information about the extent of binding at each address of the array can be stored as a profile, e.g., in a computer database.

In one embodiment the array is an array of protein products of the 1, 2, 3, 4, 5, 6, 7, 8, 9, 10, 15, 20 or all or any combination of the biomarkers of the invention. In one aspect, the invention provides for antibodies that are bound to an array which selectively bind to the protein products of the biomarkers of the invention.

5.14 Protein Production

Standard recombinant nucleic acid methods can be used to express a polypeptide or antibody of the invention (e.g., a protein product of a biomarker of the invention). Generally, a nucleic acid sequence encoding the polypeptide is cloned into a nucleic acid expression vector. Of course, if the protein includes multiple polypeptide chains, each chain must be cloned into an expression vector, e.g., the same or different vectors, that are expressed in the same or different cells. If the protein is sufficiently small, i.e., the protein is a peptide of less than 50 amino acids, the protein can be synthesized using automated organic synthetic methods. Polypeptides comprising the 5' region, 3' region or internal coding region of a biomarker of the invention, are expressed from nucleic acid expression vectors containing only those nucleotide sequences corresponding to the 5' region, 3' region or internal coding region of a biomarker of the invention. Methods for producing antibodies directed to protein products of a biomarker of the invention, or polypeptides encoded by the 5' region, 3' region or internal coding regions of a biomarker of the invention.

The expression vector for expressing the polypeptide can include, in addition to the segment encoding the polypeptide or fragment thereof, regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXTI, pSG (Stratagene) pSVK3, pBPV, pMSG, and pSVL (Pharmacia). One preferred class of preferred libraries is the display library, which is described below.

Methods well known to those skilled in the art can be used to construct vectors containing a polynucleotide of the invention and appropriate transcriptional/translational control signals. These methods include in vitro recombinant DNA techniques, synthetic techniques and in vivo recombination/genetic recombination. See, for example, the techniques described in Sambrook & Russell, *Molecular Cloning: A Laboratory Manual,* 3$^{rd}$ Edition, Cold Spring Harbor Laboratory, N.Y. (2001) and Ausubel et al., *Current Protocols in Molecular Biology* (Greene Publishing Associates and Wiley Interscience, N.Y. (1989). Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda P, and trc. Eukaryotic promoters include CMV immediate early, HSV thymidine kinase, early and late SV40, LTRs from retrovirus, mouse metallothionein-I, and various art-known tissue specific promoters. In specific embodiments, the promoter is an inducible promoter. In other embodiments, the promoter is a constitutive promoter. In yet other embodiments, the promoter is a tissue-specific promoter.

Generally, recombinant expression vectors will include origins of replication and selectable markers permitting transformation of the host cell, e.g., the ampicillin resistance gene of *E. coli* and *S. cerevisiae* auxotrophic markers (such as URA3, LEU2, HIS3, and TRP1 genes), and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The polynucleotide of the invention is assembled in appropriate phase with translation initiation and termination sequences, and preferably, a leader sequence capable of directing secretion of translated protein into the periplasmic space or extracellular medium. Optionally, a nucleic acid of the invention can encode a fusion protein including an N-terminal identification peptide imparting desired characteristics, e.g., stabilization or simplified purification of expressed recombinant product. Useful expression-vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

The present invention provides host cells genetically engineered to contain the polynucleotides of the invention. For example, such host cells may contain nucleic acids of the invention introduced into the host cell using known transformation, transfection or infection methods. The present invention also provides host cells genetically engineered to express the polynucleotides of the invention, wherein such polynucleotides are in operative association with a regulatory sequence heterologous to the host cell which drives expression of the polynucleotides in the cell.

The present invention further provides host cells containing the vectors of the present invention, wherein the nucleic acid has been introduced into the host cell using known transformation, transfection or infection methods. The host cell can be a eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example, by calcium phosphate transfection, DEAE, dextran mediated transfection, or electroporation (Davis, L. et al., *Basic Methods in Molecular Biology* (1986)). Cell-free translation systems can also be employed to produce such proteins using RNAs derived from the DNA constructs of the present invention.

Any host/vector system can be used to express one or more of the proteins listed in Table 2. Appropriate cloning and expression vectors for use with prokaryotic and eukaryotic hosts are described by Sambrook et al., in *Molecular Cloning: A Laboratory Manual*, Second Edition, Cold Spring Harbor, N.Y. (1989), the disclosure of which is incorporated herein by reference in its entirety. The most preferred host cells are those which do not normally express the particular polypeptide or which expresses the polypeptide at low natural level.

In a specific embodiment, the host cells are engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The host of the present invention may also be a yeast or other fungi. In yeast, a number of vectors containing constitutive or inducible promoters may be used. For a review see, Ausubel et al. (eds), *Current Protocols in Molecular Biology*, Vol. 2, Greene Publish. Assoc. & Wiley Interscience, Ch. 13 (1988); Grant et al., 1987, "Expression and Secretion Vectors for Yeast", Methods Enzymol. 153:516-544; Glover, *DNA Cloning*, Vol. II, IRL Press, Wash., D.C., Ch. 3 (1986); Bitter, 1987, "Heterologous Gene Expression in Yeast", Methods Enzymol. 152:673-684; and Strathern et al. (eds), *The Molecular Biology of the Yeast Saccharomyces*, Cold Spring Harbor Press, Vols. I and II (1982).

Potentially suitable yeast strains include *Saccharomyces cerevisiae, Schizosaccharomyces pombe, Kluyveromyces strains, Candida*, or any yeast strain capable of expressing heterologous proteins. Potentially suitable bacterial strains include *Escherichia coli*, enterobacteriaceae such as *Serratia marescans*, bacilli such as *Bacillus subtilis, Salmonella typhimurium*, pseudomonads or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

Various mammalian cell culture systems can also be employed to express recombinant protein. Examples of mammalian expression systems include the monkey COS cells such as COS-7 lines of monkey kidney fibroblasts, described by Gluzman, 1981, Cell 23:175 (1981), Chinese Hamster Ovary (CHO) cells, human kidney 293 cells, human epidermal A431 cells, human Colo205 cells, 3T3 cells, CV-1 cells, normal diploid cells, cell strains derived from in vitro culture of primary tissue, primary explants, HeLa cells, mouse L cells, BHK, HL-60, U937, HaK, C127, 3T3, or Jurkat cells, and other cell lines capable of expressing a compatible vector. Mammalian expression vectors will comprise an origin of replication, a suitable promoter and also any necessary ribosome-binding sites, polyadenylation site, splice donor and acceptor sites, transcriptional termination sequences, and 5' flanking nontranscribed sequences.

Microbial cells employed in expression of proteins can be disrupted by any convenient method, including freeze-thaw cycling, sonication, mechanical disruption, or use of cell lysing agents. Recombinant polypeptides produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine.

Recombinant proteins can be isolated using an techniqe well-known in the art. Scopes (*Protein Purification: Prin-*

*ciples and Practice*, Springer-Verlag, New York (1994)), for example, provides a number of general methods for purifying recombinant (and non-recombinant) proteins. The methods include, e.g., ion-exchange chromatography, size-exclusion chromatography, affinity chromatography, selective precipitation, dialysis, and hydrophobic interaction chromatography.

Variations, modifications, and other implementations of what is described herein will occur to those of ordinary skill in the art without departing from the spirit and scope of the invention.

In order that the invention described herein may be more fully understood, the following example is set forth. It should be understood that this example is for illustrative purposes only and are not to be construed as limiting this invention in any manner.

5.15 Methods for Identifying Compounds for Use in the Prevention, Treatment, Management or Amelioration Schizophrenia and/or Bipolar Disorder or a Symptom Thereof

5.15.1 Methods to Identify Compounds that Modulate the Expression or Activity of a Biomarker The present invention provides methods of identifying compounds that bind to the products of the biomarkers of the invention. The present invention also provides methods for identifying compounds that modulate the expression and/or activity of the products of the biomarkers of the invention. The compounds identified via such methods are useful for the development of one or more animal models to study schizophrenia or bipolar disorder. Further, the compounds identified via such methods are useful as lead compounds in the development of prophylactic and therapeutic compositions for prevention, treatment, management and/or amelioration of Schizophrenia and/or Bipolar Disorder or a symptom thereof. Such methods are particularly useful in that the effort and great expense involved in testing potential prophylactics and therapeutics in vivo is efficiently focused on those compounds identified via the in vitro and ex vivo methods described herein.

The present invention provides a method for identifying a compound to be tested for an ability to prevent, treat, manage or ameliorate Schizophrenia and/or Bipolar Disorder or a symptom thereof, said method comprising: (a) contacting a cell expressing a protein product of one or more biomarkers of the invention or a fragment thereof, or a RNA product of one or more biomarkers of the invention or a fragment thereof with a test compound; and (b) determining the ability of the test compound to bind to the protein product, protein fragment, RNA product, or RNA portion so that if a compound binds to the protein product, protein fragment, RNA product, RNA portion, a compound to be tested for an ability to prevent, treat, manage or ameliorate Schizophrenia and/or Bipolar Disorder or a symptom thereof is identified. The cell, for example, can be a prokaryotic cell, yeast cell, viral cell or a cell of mammalian origin. Determining the ability of the test compound to bind to the protein product, protein fragment, RNA product, or RNA portion can be accomplished, for example, by coupling the test compound with a radioisotope or enzymatic label such that binding of the test compound to the protein product, protein fragment, RNA product, or RNA portion can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a specific embodiment, the assay comprises contacting a cell which expresses a protein product of one or more biomarkers of the invention or a fragment thereof, or a RNA product of one or more biomarkers of the invention or a fragment thereof, with a known compound which binds the protein product, protein fragment, RNA product, or RNA portion to form an assay mixture, contacting the assay mixture with a test compound, and determining the ability of the test compound to interact with the protein product, protein fragment, RNA product, or RNA portion, wherein determining the ability of the test compound to interact with the protein product, protein fragment, RNA product, or RNA portion comprises determining the ability of the test compound to preferentially bind to the protein product, protein fragment, RNA product, or RNA portion as compared to the known compound.

The present invention provides a method for identifying a compound to be tested for an ability to prevent, treat, manage or ameliorate schizophrenia and/or bipolar disorder or a symptom thereof, said method comprising: (a) contacting a protein product of one or more biomarkers of the invention or a fragment thereof, or a RNA product of one or more biomarkers of the invention or a portion thereof with a test compound; and (b) determining the ability of the test compound to bind to the protein product, protein fragment, RNA product, or RNA portion so that if a compound binds to the protein product, protein fragment, RNA product, or RNA portion, a compound to be tested for an ability to prevent, treat, manage or ameliorate Schizophrenia and/or Bipolar Disorder or a symptom thereof is identified. Binding of the test compound to the protein product or protein fragment can be determined either directly or indirectly. In a specific embodiment, the assay includes contacting a protein product of one or more biomarkers of the invention or a fragment thereof, or a RNA product of one or more biomarkers of the invention or a portion thereof with a known compound which binds the protein product, protein fragment, RNA product, or RNA portion to form an assay mixture, contacting the assay mixture with a test compound, and determining the ability of the test compound to interact with the protein product, protein fragment, RNA product, or RNA portion, wherein determining the ability of the test compound to interact with the protein product, protein fragment, RNA product, or RNA portion comprises determining the ability of the test compound to preferentially bind to the protein product, protein fragment, RNA product, or RNA portion as compared to the known compound. Techniques well known in the art can be used to determine the binding between a test compound and a protein product of a biomarker of the invention or a fragment thereof, or a RNA product of a biomarker of the invention or a portion thereof.

In some embodiments of the above assay methods of the present invention, it may be desirable to immobilize a RNA product of a biomarker of the invention or a portion thereof, or its target molecule to facilitate separation of complexed from uncomplexed forms of the RNA product or RNA portion, the target molecule or both, as well as to accommodate automation of the assay. In more than one embodiment of the above assay methods of the present invention, it may be desirable to immobilize either a protein product of a biomarker of the invention or a fragment thereof, or its target molecule to facilitate separation of complexed from uncomplexed forms of one or both of the proteins, as well as to accommodate automation of the assay. Binding of a test compound to a protein product of a biomarker of the invention or a fragment thereof can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase (GST) fusion proteins can be adsorbed onto glutathione sepharose beads (Sigma Chemical; St. Louis, Mo.) or glutathione derivatized microtiter plates, which are then combined with the test compound or the test compound and either the non-adsorbed target protein or a protein product of a biomarker of the invention or a fragment thereof, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding of a protein product of a biomarker of the invention or a fragment thereof can be determined using standard techniques.

Other techniques for immobilizing proteins on matrices can also be used in the screening assays of the invention. For example, either a protein product of a biomarker of the invention or a fragment thereof, or a target molecule can be immobilized utilizing conjugation of biotin and streptavidin. A biotinylated protein product of a biomarker of the invention or a target molecule can be prepared from biotin-NHS(N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with a protein product of a biomarker of the invention or a fragment thereof can be derivatized to the wells of the plate, and protein trapped in the wells by antibody conjugation. Methods for detecting such complexes, in addition to those described above for the GST-immobilized complexes, include immunodetection of complexes using antibodies reactive with a protein product of a biomarker of the invention, as well as enzyme-linked assays which rely on detecting an enzymatic activity associated with a protein product of a biomarker of the invention or a fragment thereofor target molecule.

The interaction or binding of a protein product of a biomarker of the invention or a fragment thereof to a test compound can also be determined using such proteins or protein fragments as "bait proteins" in a two-hybrid assay or three hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and International Publication No. WO 94/10300).

The present invention provides a method for identifying a compound to be tested for an ability to prevent, treat, manage or ameliorate Schizophrenia and/or Bipolar Disorder or a symptom thereof, said method comprising: (a) contacting a cell expressing a protein or RNA product of one or more biomarkers of the invention with a test compound; (b) determining the amount of the protein or RNA product present in (a); and (c) comparing the amount in (a) to that present in a corresponding control cell that has not been contacted with the test compound, so that if the amount of the protein or RNA product is altered relative to the amount in the control, a compound to be tested for an ability to prevent, treat, manage or ameliorate Schizophrenia and/or Bipolar Disorder or a symptom thereof is identified. In a specific embodiment, the expression level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the expression level in the control as determined by utilizing an assay described herein (e.g., a microarray or RT-PCR) or an assay well known to one of skill in the art. In alternate embodiments, such a method comprises determining the amount of the protein or RNA product of at least 2, at least 3, at least 4, at least 5, at least 6, at least 7, 1 to 3, 1 to 5, 1-7, all or any combination of the biomarkers of the invention present in the cell and comparing the amounts to those present in the control.

The cells utilized in the cell-based assays described herein can be engineered to express a biomarker of the invention utilizing techniques known in the art. See, e.g., Section III entitled "Recombinant Expression Vectors and Host Cells" of U.S. Pat. No. 6,245,527, which is incorporated herein by reference. Alternatively, cells that endogenously express a biomarker of the invention can be used. For example, brain cells may be used.

In a specific embodiment, brain cells are isolated from a "normal" individual, or an individual with schizophrenia and/or bipolar disorder and are incubated in the presence and absence of a test compound for varying amounts of time (i.e., 30 min, 1 hr, 5 hr, 24 hr, 48 hr and 96 hrs). When screening for prophylactic or therapeutic agents, a clone of the full sequence of a biomarker of the invention or functional portion thereof is used to transfect brain cells. The transfected brain cells are cultured for varying amounts of time (i.e., 1, 2, 3, 5, 7, 10, or 14 days) in the presence or absence of test compound. Following incubation, target nucleic acid samples are prepared from the brain cells and hybridized to a nucleic acid probe corresponding to a nucleic acid sequence which are differentially expressed in schizophrenia and/or bipolar disorder. The nucleic acid probe is labeled, for example, with a radioactive label, according to methods well-known in the art and described herein. Hybridization is carried out by northern blot, for example as described in Ausubel et al., supra or Sambrook et al., supra). The differential hybridization, as defined herein, of the target to the samples on the array from normal relative to RNA from schizophrenia and/or bipolar disorder is indicative of the level of expression of RNA corresponding to a differentially expressed specific nucleic acid sequence. A change in the level of expression of the target sequence as a result of the incubation step in the presence of the test compound, is indicative of a compound that increases or decreases the expression of the corresponding schizophrenia and/or bipolar disorder biomarker specific nucleic acid sequence.

The present invention also provides a method for identifying a compound to be tested for an ability to prevent, treat, manage or ameliorate schizophrenia and/or bipolar disorder or a symptom thereof, said method comprises: (a) contacting a cell-free extract (e.g., a brain cell extract) with a nucleic acid sequence encoding a protein or RNA product of one or more biomarkers of the invention and a test compound; (b) determining the amount of the protein or RNA product present in (a); and (c) comparing the amount(s) in (a) to that present to a corresponding control that has not been contacted with the test compound, so that if the amount of the protein or RNA product is altered relative to the amount in the control, a compound to be tested for an ability to prevent, treat, manage or ameliorate schizophrenia and/or bipolar disorder or a symptom thereof is identified. In a specific embodiment, the expression level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the expression level in the control sample determined by utilizing an assay described herein (e.g., a microarray or RT-PCR) or an assay well known to one of skill in the art. In alternate embodiments, such a method comprises determining the amount of a protein or RNA product of at least 2, at least 3, at least 4, at least 5, at least 6, at least 7, 1 to 3, 1 to 5, 1-7, all or any combination of the biomarkers of the invention present in the extract and comparing the amounts to those present in the control. In certain embodiments, the amount of RNA product of a biomarker of the invention is determined, in other embodiments, the amount of protein product of a biomarker of the invention is determined, while in still other embodiments, the amount of RNA and protein product of a biomarker of the invention is determined. Standard methods and compositions for determining the amount of RNA or protein product of a biomarker of the invention can be utilized. Such methods and compositions are described in detail above.

In specific embodiments, in a screening assay described herein, the amount of protein or RNA product of a biomarker of the invention is determined utilizing kits. Such kits comprise materials and reagents required for measuring the expression of at least 1, at least 2, at least 3, at least 4, at least 5, at least 6, at least 7, at least 8 or more protein or RNA products of at least 1, at least 2, at least 3, at least 4, at least 5, at least 6, at least 7, at least 8, all or any combination of the biomarkers of the invention. In specific embodiments, the kits may further comprise one or more additional reagents employed in the various methods, such as: (1) reagents for purifying RNA from blood, brain cells; (2) primers for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization and washing buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA transcript (preferably, mRNA) for use as a control.

In some embodiments, the kits are RT-PCR kits. In other embodiments, the kits are nucleic acid arrays and protein arrays. Such kits according to the subject invention will at least comprise an array having associated protein or nucleic acid members of the invention and packaging means therefore. Alternatively the protein or nucleic acid members of the invention may be prepackaged onto an array.

In a specific embodiment, kits for measuring a RNA product of a biomarker of the invention comprise materials and reagents that are necessary for measuring the expression of the RNA product. For example, a microarray or RT-PCR kit may be used and contain only those reagents and materials necessary for measuring the levels of RNA products of at least 1, at least 2, at least 3, at least 4, at least 5, at least 6, at least 7, at least 8, all or any combination of the biomarkers of the invention. Alternatively, in some embodiments, the kits can comprise materials and reagents that are not limited to those required to measure the levels of RNA products of 1, 2, 3, 4, 5, 6, 7, 8 all or any combination of the biomarkers of the invention. For example, a microarray kit may contain reagents and materials necessary for measuring the levels of RNA products 1, 2, 3, 4, 5, 6, 7, 8, all or any combination of the biomarkers of the invention, in addition to reagents and materials necessary for measuring the levels of the RNA products of at least 1, at least 2, at least 3, at least 4, at least 5, at least 6, at least 7, at least 8, or more genes other than the biomarkers of the invention. In a specific embodiment, a microarray or RT-PCR kit contains reagents and materials necessary for measuring the levels of RNA products of at least 1, at least 2, at least 3, at least 4, at least 5, at least 6, at least 7, at least 8, all or any combination of the biomarkers of the invention, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not biomarkers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not biomarkers of the invention. For nucleic acid microarray kits, the kits generally comprise probes attached to a support surface. The probes may be labeled with a detectable label. In a specific embodiment, the probes are specific for the 5' region, the 3' region, the internal coding region, an exon(s), an intron(s), an exon junction(s), or an exon-intron junction(s), of 1, 2, 3, 4, 5, 6, 7, 8, all or any combination of the biomarkers of the invention. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For RT-PCR kits, the kits generally comprise pre-selected primers specific for particular RNA products (e.g., an exon(s), an intron(s), an exon junction(s), and an exon-intron junction(s)) of 1, 2, 3, 4, 5, 6, 7, 8, all or any combination of the biomarkers of the invention. The RT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for 1, 2, 3, 4, 5, 6, 7, 8, all or any combination of the biomarkers of the invention. The probes may or may not be labeled with a detectable label (e.g., a fluorescent label). Each component of the RT-PCR kit is generally in its own suitable container. Thus, these kits generally comprise distinct containers suitable for each individual reagent, enzyme, primer and probe. Further, the RT-PCR kits may comprise instructions for performing the assay and methods for interpreting and analyzing the data resulting from the performance of the assay. For antibody based kits, the kit can comprise, for example: (1) a first antibody (which may or may not be attached to a support) which binds to protein of interest (e.g., a protein product of 1, 2, 3, 4, 5, 6, 7, 8, all or any combination of the biomarkers of the invention); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay.

Reporter gene-based assays may also be conducted to identify a compound to be tested for an ability to prevent, treat, manage or ameliorate schizophrenia and/or bipolar disorder or a symptom thereof. In a specific embodiment, the present invention provides a method for identifying a compound to be tested for an ability to prevent, treat, manage or ameliorate schizophrenia and/or bipolar disorder or a symptom thereof, said method comprising: (a) contacting a compound with a cell expressing a reporter gene construct comprising a reporter gene operably linked to a regulatory element of a biomarker of the invention (e.g., a promoter/enhancer element); (b) measuring the expression of said reporter gene; and (c) comparing the amount in (a) to that present in a corresponding control cell that has not been contacted with the test compound, so that if the amount of expressed reporter gene is altered relative to the amount in the control cell, a compound to be tested for an ability to prevent, treat, manage or ameliorate schizophrenia and/or bipolar disorder or a symptom thereof is identified. In accordance with this embodiment, the cell may naturally express the biomarker or be engineered to express the biomarker. In another embodiment, the present invention provides a method for identifying a compound to be tested for an ability to prevent, treat, manage or ameliorate schizophrenia and/or bipolar disorder or a symptom thereof, said method comprising: (a) contacting a compound with a cell-free extract and a reporter gene construct comprising a reporter gene operably linked to a regulatory element of a biomarker of the invention (e.g., a promoter/enhancer element); (b) measuring the expression of said reporter gene; and (c) comparing the amount in (a) to that present in a corresponding control that has not been contacted with the test compound, so that if the amount of expressed reporter gene is altered relative to the amount in the control, a compound to be tested for an ability to prevent, treat, manage or ameliorate schizophrenia and/or bipolar disorder or a symptom thereof is identified. Any reporter gene well-known to one of skill in the art may be used in reporter gene constructs used in accordance with the methods of the invention. Reporter genes refer to a nucleotide sequence encoding a RNA transcript or protein that is readily detectable either by its presence (by, e.g., RT-PCR, Northern blot, Western Blot, ELISA, etc.) or activity. Non-limiting examples of reporter genes are listed in Table 6, infra. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

TABLE 7

Reporter Genes and the Properties of the Reporter Gene Products

| Reporter Gene | Protein Activity & Measurement |
|---|---|
| CAT (chloramphenicol acetyltransferase) | Transfers radioactive acetyl groups to chloramphenicol or detection by thin layer chromatography and autoradiography |
| GAL (beta-galactosidase) | Hydrolyzes colorless galactosides to yield colored products. |
| GUS (beta-glucuronidase) | Hydrolyzes colorless glucuronides to yield colored products. |
| LUC (luciferase) | Oxidizes luciferin, emitting photons |
| GFP (green fluorescent protein) | Fluorescent protein without substrate |
| SEAP (secreted alkaline phosphatase) | Luminescence reaction with suitable substrates or with substrates that generate chromophores |
| HRP (horseradish peroxidase) | In the presence of hydrogen oxide, oxidation of 3,3',5,5'-tetramethylbenzidine to form a colored complex |
| AP (alkaline phosphatase) | Luminescence reaction with suitable substrates or with substrates that generate chromophores |

In accordance with the invention, cells that naturally or normally express one or more, all or any combination of the biomarkers of the invention can be used in the methods described herein. Alternatively, cells can be engineered to express one or more, all or any combination of the biomarkers of the invention, or a reporter gene using techniques well-known in the art and used in the methods described herein. Examples of such techniques include, but are not to, calcium phosphate precipitation (see, e.g., Graham & Van der Eb, 1978, Virol. 52:546), dextran-mediated transfection, calcium phosphate mediated transfection, polybrene mediated transfection, protoplast fusion, electroporation, encapsulation of the nucleic acid in liposomes, and direct microinjection of the nucleic acid into nuclei.

In a specific embodiment, the cells used in the methods described herein are brain cells or cell lines, lymphocytes (T or B lymphocytes), monocytes, neutrophils, macrophages, eosinophils, basophils, erythrocytes or platelets. In a preferred embodiment, the cells used in the methods described herein are brain cells. In another preferred embodiment, the cells used in the methods described herein are lymphocytes. In another embodiment, the cells used in the methods described herein are immortalized cell lines derived from a source, e.g., a tissue. Any cell-free extract that permits the translation, and optionally but preferably, the transcription, of a nucleic acid can be used in accordance with the methods described herein. The cell-free extract may be isolated from cells of any species origin. For example, the cell-free translation extract may be isolated from human cells, cultured mouse cells, cultured rat cells, Chinese hamster ovary (CHO) cells, *Xenopus* oocytes, rabbit reticulocytes, wheat germ, or rye embryo (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). In a preferred embodiment, the cell-free extract is an extract isolated from human cells. In a specific embodiment, the human cells are HeLa cells, lymphocytes, or brain cells or cell lines. In addition to the ability to modulate the expression levels of RNA and/or protein products a biomarker of the invention, it may be desirable, at least in certain instances, that compounds modulate the activity of a protein product of a biomarker of the invention. Thus, the present invention provides methods of identifying compounds to be tested for an ability to prevent, treat, manage or ameliorate schizophrenia and/or bipolar disorder or a symptom thereof, comprising methods for identifying compounds that modulate the activity of a protein product of one or more biomarkers of the invention. Such methods can comprise: (a) contacting a cell expressing a protein product of one or more biomarkers of the invention with a test compound; (b) determining the activity level of the protein product; and (c) comparing the activity level to that in a corresponding control cell that has not been contacted with the test compound, so that if the level of activity in (a) is altered relative to the level of activity in the control cell, a compound to be tested for an ability to prevent, treat, manage or ameliorate schizophrenia and/or bipolar disorder or a symptom thereof is identified. In a specific embodiment, the activity level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the activity level in the control as determined by utilizing an assay described herein (e.g., a microarray or RT-PCR) or an assay well known to one of skill in the art. In alternate embodiments, such a method comprises determining the activity level of a protein product of at least 2, at least 3, at least 4, at least 5, at least 6, at least 7, at least 8, at least 9, at least 10, at least 12, at least 15, at least 20, at least 25, 1 to 5, 1-10, 5-10, 5-25, or 10-40, all or any combination of the biomarkers of the invention present in the cell and comparing the activity levels to those present in the control.

The present invention provides methods of identifying compounds to be tested for an ability to prevent, treat, manage or ameliorate schizophrenia and/or bipolar disorder or a symptom thereof, comprising: (a) contacting a cell-free extract with a nucleic acid encoding a protein product of one or more biomarkers of the invention and a test compound; (b) determining the activity level of the protein product; and (c) comparing the activity level to that in a corresponding control that has not been contacted with the test compound, so that if the level of activity in (a) is altered relative to the level of activity in the control, a compound to be tested for an ability to prevent, treat, manage or ameliorate schizophrenia and/or bipolar disorder or a symptom thereof is identified. In a specific embodiment, the activity level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the activity level in the control as determined by utilizing an assay described herein (e.g., a microarray or RT-PCR) or an assay well known to one of skill in the art. In alternate embodiments, such a method comprises determining the activity level of a protein product of at least 2, at least 3, at least 4, at least 5, at least 6, at least 7, at least 8, 1 to 3, 1 to 5, 1-7 all or any combination of the biomarkers of the invention present in the sample and comparing the activity levels to those present in the control.

Standard techniques can be utilized to determine the level of activity of a protein product of a biomarker of the invention. Activities of protein products of biomarkers of the invention that can be determined using techniques well known in the art.

5.15.2 Method to Utilize the Biological Activity of the Compounds

Upon identification of compounds to be tested for an ability to prevent, treat, manage or ameliorate schizophrenia and/or bipolar disorder or a symptom thereof (for convenience referred to herein as a "lead" compound), the compounds can be further investigated. For example, the compounds identified via the present methods can be further tested in vivo in accepted animal models of schizophrenia and/or bipolar disorder. Further, the compounds identified via the methods can be analyzed with respect to their specificity. Techniques for such additional compound investigation are well known to one of skill in the art.

In one embodiment, the effect of a lead compound can be assayed by measuring the cell growth or viability of the target cell. Such assays can be carried out with representative cells of cell types involved in schizophrenia and/or bipolar disorder (e.g., brain cells; cells isolated from different portions of the brain; stem cells and the like). Alternatively, instead of culturing cells from a patient, a lead compound may be screened using cells of a cell line. Many assays well-known in the art can be used to assess the survival and/or growth of a patient cell or cell line following exposure to a lead compound; for example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H)-thymidine incorporation (see, e.g., Chen, J., 1996, Oncogene 13:1395-403; Jeoung, J., 1995, J. Biol. Chem. 270:18367-73), by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and RNA (e.g., mRNA) and activity can be determined by any method well known in the art. For example, protein can be quantitated by known immunodiagnostic methods such as Western blotting or immunoprecipitation using commercially available antibodies. mRNA can be quantitated using methods that are well known and routine in the art, for example, using northern analysis, RNase protection, the polymerase chain reaction in connection with the reverse transcription. Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

5.15.3 Animal Models

Compounds can be tested in suitable animal model systems prior to use in humans. Such animal model systems include but are not limited to rats, mice, chicken, cows, monkeys, pigs, dogs, rabbits, etc. Any animal system well-known in the art may be used. In certain embodiments, compounds are tested in a mouse model. Compounds can be administered repeatedly.

Accepted animal models can be utilized to determine the efficacy of the compounds identified via the methods described above for the prevention, treatment, management and/or amelioration of schizophrenia and/or bipolar disorder or a symptom thereof 5.15.4 Toxicity The toxicity and/or efficacy of a compound identified in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Cells and cell lines that can be used to assess the cytotoxicity of a compound identified in accordance with the invention include, but are not limited to, peripheral blood mononuclear cells (PBMCs), Caco-2 cells, and Huh7 cells. The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects. The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

5.15.5 Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu. Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to the proteins of interest (i.e., the protein products of a biomarker of the invention) using the above-described screens for biologic activity. Alternatively, lead compounds with little or no biologic activity, as ascertained in the screen, can also be used to design analogs and congeners of the compound that have biologic activity.

5.15.6 Compounds

Compounds that can be tested and identified methods described herein can include, but are not limited to, compounds obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, NY 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, LA 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the methods of the invention, including microbial, fungal, plant or animal extracts.

Compounds from large libraries of synthetic or natural compounds can be screened. Numerous means are currently used for random and directed synthesis of saccharide, peptide, and nucleic acid-based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and are prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Furthermore, diversity libraries of test compounds, including small molecule test compounds, may be utilized. Libraries screened using the methods of the present invention can comprise a variety of types of compounds. Examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as $\alpha$-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a specific embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available For example, libraries may be commercially obtained from, e.g., Specs and BioSpecs B.V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), Asinex (Moscow, Russia), ComGenex (Princeton, N.J.), Ru, Tripos, Inc. (St. Louis, Mo.), ChemStar, Ltd (Moscow, Russia), 3D Pharmaceuticals (Exton, Pa.), and Martek Biosciences (Columbia, Md.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry. Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multistep solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial compound libraries useful for the methods of the present invention can be synthesized on supports. In one embodiment, a split synthesis method, a protocol of separating and mixing supports during the synthesis, is used to synthesize a library of compounds on supports (see e.g., Lam et al., 1997, Chem. Rev. 97:41-448; Ohlmeyer et al., 1993, Proc. Natl. Acad. Sci. USA 90:10922-10926 and references cited therein). Each support in the final library has substantially one type of compound attached to its surface. Other methods for synthesizing combinatorial libraries on supports, wherein one product is attached to each support, will be known to those of skill in the art (see, e.g., Nefzi et al., 1997, Chem. Rev. 97:449-472).

In some embodiments of the present invention, compounds can be attached to supports via linkers. Linkers can be integral and part of the support, or they may be nonintegral that are either synthesized on the support or attached thereto after synthesis. Linkers are useful not only for providing points of compound attachment to the support, but also for allowing different groups of molecules to be cleaved from the support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the support prior to high throughput screening of the compounds.

If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds. Examples of such techniques include, but are not limited to, mass spectrometry, NMR spectroscopy, X-ray crytallography and vibrational spectroscopy.

5.16 Use of Identified Compounds to Prevent, Treat, Manage or Ameliorate Schizophrenia And/or Bipolar Disorder or a Symptom Thereof The present invention provides methods of preventing, treating, managing or ameliorating schizophrenia and/or bipolar disorder or a symptom thereof, said methods comprising administering to a subject in need thereof one or more compounds identified in accordance with the methods of the invention. In certain embodiments, the subject has mild, moderate, marked or severe schizophrenia and/or bipolar disorder.

In a preferred embodiment, the subject is human. In one embodiment, the invention provides a method of preventing, treating, managing or ameliorating schizophrenia and/or bipolar disorder or a symptom thereof, said method comprising administering to a subject in need thereof a dose of a prophylactically or therapeutically effective amount of one or more compounds identified in accordance with the methods of the invention. In a specific embodiment, a compound identified in accordance with the methods of the invention is not administered to prevent, treat, or ameliorate schizophrenia and/or bipolar disorder or a symptom thereof, if such compound has been used previously to prevent, treat, manage or ameliorate schizophrenia and/or bipolar disorder or a symptom thereof. In another embodiment, a compound identified in accordance with the methods of the invention is not administered to prevent, treat, or ameliorate schizophrenia and/or bipolar disorder or a symptom thereof, if such compound has suggested to be used to prevent, treat, manage or ameliorate schizophrenia and/or bipolar disorder or a symptom thereof. In another embodiment, a compound identified in accordance with the methods of the invention specifically binds to and/or alters the expression and/or activity level of a protein or RNA product of only one biomarker of the invention. In another embodiment, a compound identified in accordance with the methods of the invention is not administered to prevent, treat, or ameliorate schizophrenia and/or bipolar disorder or a symptom thereof, if such compound binds to and/or alters the expression and/or activity of a protein or RNA product of one, two, three, all or any combination of the following biomarkers of Table 1. In yet another embodiment, a compound identified in accordance with the methods of the invention binds to and/or alters the expression and/or activity level of a protein or RNA product of at least 2, at least 3, at least 4, at least 5, at least 10, at least 15, at least 20, at least 25, a or more biomarkers of the invention.

The invention also provides methods of preventing, treating, managing or ameliorating schizophrenia and/or bipolar disorder or a symptom thereof, said methods comprising administering to a subject in need thereof one or more of the compounds identified utilizing the screening methods described herein, and one or more other therapies (e.g., prophylactic or therapeutic agents and surgery). In a specific embodiment, such therapies are currently being used, have been used or are known to be useful in the prevention, treatment, management or amelioration of schizophrenia and/or bipolar disorder or a symptom thereof (including, but not limited to the prophylactic or therapeutic agents listed herein). The therapies (e.g., prophylactic or therapeutic agents) of the combination therapies of the invention can be administered sequentially or concurrently. In a specific embodiment, the combination therapies of the invention comprise a compound identified in accordance with the invention and at least one other therapy that has the same mechanism of action as said compound. In another specific embodiment, the combination therapies of the invention comprise a compound identified in accordance with the methods of the invention and at least one other therapy (e.g., prophylactic or therapeutic agent) which has a different mechanism of action than said compound. The combination therapies of the present invention improve the prophylactic or therapeutic effect of a compound of the invention by functioning together with the compound to have an additive or synergistic effect. The combination therapies of the present invention reduce the side effects associated with the therapies (e.g., prophylactic or therapeutic agents). The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In specific embodiment, a pharmaceutical composition comprising one or more compounds identified in an assay described herein is administered to a subject, preferably a human, to prevent, treat, manage or ameliorate schizophrenia and/or bipolar disorder or a symptom thereof. In accordance with the invention, the pharmaceutical composition may also comprise one or more prophylactic or therapeutic agents. Preferably, such agents are currently being used, have been used or are known to be useful in the prevention, treatment, management or amelioration of schizophrenia and/or bipolar disorder or a symptom thereof.

A compound identified in accordance with the methods of the invention may be used as a first, second, third, fourth or fifth line of therapy for schizophrenia and/or bipolar disorder. The invention provides methods for treating, managing or ameliorating schizophrenia and/or bipolar disorder or a symptom thereof in a subject refractory to conventional therapies for schizophrenia and/or bipolar disorder, said methods comprising administering to said subject a dose of a prophylactically or therapeutically effective amount of a compound identified in accordance with the methods of the invention.

The invention provides methods for treating, managing or ameliorating schizophrenia and/or bipolar disorder or a symptom thereof in a subject refractory to existing single agent therapies for schizophrenia and/or bipolar disorder, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating or managing a schizophrenia and/or bipolar disorder by administering a compound identified in accordance with the methods of the invention in combination with any other therapy (e.g., surgery) to patients who have proven refractory to other therapies but are no longer on these therapies. The invention also provides methods for the treatment or management of a patient having schizophrenia and/or bipolar disorder and immunosuppressed by reason of having previously undergone other therapies. The invention also provides alternative methods for the treatment or management of schizophrenia and/or bipolar disorder where hormonal therapy and/or biological therapy/immunotherapy has proven or may prove too toxic, i.e., results in unacceptable or unbearable side effects, for the subject being treated or managed.

5.17 Compounds of the Invention

Representative, non-limiting examples of compounds that can used in accordance with the methods of the invention to prevent, treat, manage and/or ameliorate schizophrenia and/or bipolar disorder or a symptom thereof are described in detail below.

First, such compounds can include, for example, antisense, ribozyme, or triple helix compounds that can downregulate the expression or activity of a protein or RNA product of a biomarker of the invention. Such compounds are described in detail in the subsection below.

Second, such compounds can include, for example, antibody compositions that can modulate the expression of a protein or RNA product of a biomarker of the invention, or the activity of a protein product of a biomarker of the invention.

In a specific embodiment, the antibody compositions down-regulate the expression a protein or RNA product of a biomarker of the invention, or the activity of a protein product of a biomarker of the invention. Such compounds are described in detail in the subsection below.

Third, such compounds can include, for example, protein products of a biomarker of the invention. The invention encompasses the use of peptides or peptide mimetics selected to mimic a protein product of a biomarker of the invention to prevent, treat, manage or ameliorate schizophrenia and/or bipolar disorder or a symptom thereof. Further, such compounds can include, for example, dominant-negative polypeptides that can modulate the expression a protein or RNA product of a biomarker of the invention, or the activity of a protein product of a biomarker of the invention.

The methods also encompasses the use derivatives, analogs and fragments of a protein product of a biomarker of the invention to prevent, treat, manage or ameliorate schizophrenia and/or bipolar disorder or a symptom thereof. In particular, the invention encompasses the use of fragments of a protein product of a biomarker of the invention comprising one or more domains of such a protein(s) to prevent, treat, manage or ameliorate schizophrenia and/or bipolar disorder or a symptom thereof. In another specific embodiment, the invention encompasses the use of a protein product of a biomarker of the invention, or an analog, derivative or fragment of such a protein which is expressed as a fusion, or chimeric protein product (comprising the protein, fragment, analog, or derivative joined via a peptide bond to a heterologous protein sequence). In specific embodiments, an antisense oligonucleotide of at least 1, at least 2, at least 3, at least 4, at least 5, at least 6, at least 7, at least 8, at least 9, at least 10, at least 15, at least 20, at least 25, a, or more of biomarkers of the invention are administered to prevent, treat, manage or ameliorate schizophrenia and/or bipolar disorder or a symptom thereof. In other embodiments, one or more of protein products of a biomarker of the invention or a fragment, analog, or derivative thereof are administered to prevent, treat, manage or ameliorate schizophrenia and/or bipolar disorder or a symptom thereof. In other embodiment, one or more antibodies that specifically bind to a protein product of the invention are administered to prevent, treat, manage or ameliorate schizophrenia and/or bipolar disorder or a symptom thereof. In other embodiments, one or more dominant-negative polypeptides are administered to prevent, treat, manage or ameliorate schizophrenia and/or bipolar disorder or a symptom thereof.

5.17.1 Antisense, Ribozyme, Triple-Helix Compositions

Standard techniques can be utilized to produce antisense, triple helix, or ribozyme molecules reactive to one or more of the genes listed in Tables 1-4, and transcripts of the genes the genes listed in Tables 1-4, for use as part of the methods described herein. First, standard techniques can be utilized for the production of antisense nucleic acid molecules, i.e., molecules which are complementary to a sense nucleic acid encoding a polypeptide of interest, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of interest. The non-coding regions ("5' and 3' untranslated regions") are the 5' and 3' sequences that flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest). Antisense nucleic acid molecules administered to a subject or generated in situ such that they hybridize with or bind to cellular mRNA encoding the polypeptide of interest to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue, e.g., a joint (e.g., a knee, hip, elbow, and knuckle), site. Alternatively, antisense nucleic acid molecules can be modified to target selected cells and then administered systemically. For example, for systemic administration, antisense molecules can be modified such that they specifically bind to receptors or antigens expressed on a selected cell, e.g., a T cell or brain cell, surface, e.g., by linking the antisense nucleic acid molecules to peptides or antibodies which bind to cell surface receptors or antigens. The antisense nucleic acid molecules can also be delivered to cells using vectors, e.g., gene therapy vectors, described below. To achieve sufficient intracellular concentrations of the antisense molecules, vector constructs in which the antisense nucleic acid molecule is placed under the control of a strong pol II or pol III promoter are preferred.

An antisense nucleic acid molecule of interest can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330). Ribozymes are catalytic RNA molecules with ribonuclease activity that are capable of cleaving a single-stranded nucleic acid, such as an mRNA, to which they have a complementary region, and can also be generated using standard techniques. Thus, ribozymes (e.g., hammerhead ribozymes (described in Haselhoff and Gerlach, 1988, Nature 334:585-591)) can be used to catalytically cleave mRNA transcripts to thereby inhibit translation of the protein encoded by the mRNA. A ribozyme having specificity for a nucleic acid molecule encoding a polypeptide of interest can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of interest can be used to select a catalytic RNA having a specific ribonuclease activity from a pool of RNA molecules. See, e.g., Bartel and Szostak, 1993, Science 261:1411-1418.

Triple helical structures can also be generated using well known techniques. For example, expression of a polypeptide of interest can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, Anticancer Drug Des. 6(6):569-84; Helene, 1992, Ann. N.Y. Acad. Sci. 660: 27-36; and Maher, 1992, Bioassays 14(12):807-15.

In various embodiments, nucleic acid compositions can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, supra; Perry-O'Keefe et al., 1996, Proc. Natl. Acad. Sci. USA 93: 14670-675. PNAs can, for example, be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn-et al., 1996, Nucleic Acids Res. 24(17):3357-63. For example, a DNA chain can be synthesized on a support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, Nucleic Acids Res. 17:5973-88). PNA monomers are then coupled in a stepwise manner to produce a chimeric molecule with a 5' PNA segment and a 3' DNA segment (Finn et al., 1996, Nucleic Acids Res. 24(17):3357-63). Alternatively, chimeric molecules can be synthesized with a 5' DNA segment and a 3' PNA segment (Peterser et al., 1975, Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; International Publication No. WO 88/09810) or the blood-brain barrier (see, e.g., International Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

5.17.2 Antibody Compositions

In one embodiment, antibodies that specifically bind to one or more protein products of one or more biomarkers of the invention are administered to a subject, preferably a human, to prevent, treat, manage or ameliorate schizophrenia and/or bipolar disorder or a symptom thereof. In another embodiment, any combination of antibodies that specifically bind to one or more protein products of one or more biomarkers of the invention are administered to a subject, preferably a human, to prevent, treat, manage or ameliorate schizophrenia and/or bipolar disorder or a symptom thereof. In a specific embodiment, one or more antibodies that specifically bind to one or more protein products of one or more biomarkers of the invention are administered to a subject, preferably a human, in combination with other types of therapies (e.g., NSAIDS) to prevent, treat, manage or ameliorate schizophrenia and/or bipolar disorder or a symptom thereof. In certain embodiments, antibodies known in the art that specifically bind to one or more protein products of one or more biomarkers of the invention are administered to a subject, preferably a human, alone or in combination with other types of therapies (e.g., NSAIDS) to prevent, treat, manage or ameliorate schizophrenia and/or bipolar disorder or a symptom thereof. In other embodiments, antibodies known in the art that specifically bind to one or more protein products of one or more biomarkers of the invention are not administered to a subject, preferably a human, alone or in combination with other types of therapies (e.g., NSAIDS) to prevent, treat, manage or ameliorate schizophrenia and/or bipolar disorder or a symptom thereof.

One or more antibodies that specifically bind to one or more protein products of one or more biomarkers of the invention can be administered to a subject, preferably a human, using various delivery systems are known to those of skill in the art. For example, such antibodies can be administered by encapsulation in liposomes, microparticles or microcapsules. See, e.g., U.S. Pat. Nos. 5,762,904, 6,004,534, and International Publication No. WO 99/52563. In addition, such antibodies can be administered using recombinant cells capable of expressing the antibodies, or retroviral, other viral vectors or non-viral vectors capable of expressing the antibodies.

Antibodies that specifically bind one or more protein products of one or more biomarkers of the invention can be obtained from any known source. For example, Table 5 provides a list of commercially available antibodies specific for one or more of the protein products of the biomarkers of the invention. Alternatively, antibodies that specifically bind to one or more protein products of one or more biomarkers of the invention can be produced by any method known in the art for the synthesis of antibodies, in particular, by chemical synthesis or preferably, by recombinant expression techniques.

Antibodies include, but are not limited to, polyclonal antibodies, monoclonal antibodies, bispecific antibodies, multispecific antibodies, human antibodies, humanized antibodies, camelised antibodies, chimeric antibodies, single-chain Fvs (scFv) (see e.g., Bird et al. (1988) *Science* 242:423-426; and Huston et al. (1988) *Proc. Natl. Acad. Sci. USA* 85:5879-5883), single chain antibodies, single domain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. The term "antibody", as used herein, refers to immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. Examples of immunologically active fragments of immunoglobulin molecules include F(ab) fragments (a monovalent fragment consisting of the VL, VH, CL and CH1 domains) and F(ab')2 fragments (a bivalent fragment comprising two Fab fragments linked by a disulfide bridge at the hinge region) which can be generated by treating the antibody with an enzyme such as pepsin or papain. Immunologically active fragments also include, but are not limited to, Fd fragments (consisting of the VH and CH1 domains), Fv fragments (consisting of the VL and VH domains of a single arm of an antibody), dAb fragments (consisting of a VH domain; Ward et al., (1989) *Nature* 341:544-546), and isolated complementarity determining regions (CDRs). Antibodies that specifically bind to an antigen can be produced by any method known in the art for the synthesis of antibodies, in particular, by chemical synthesis or preferably, by recombinant expression techniques.

Polyclonal antibodies that specifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

The term "monospecific antibody" refers to an antibody that displays a single binding specificity and affinity for a particular target, e.g., epitope. This term includes monoclonal antibodies. Monoclonal antibodies can be prepared using a wide variety of techniques known in the art including the use of hybridoma, recombinant, and phage display technologies, or a combination thereof. See, e.g., U.S. Pat. Nos. RE 32,011, 4,902,614, 4,543,439, 4,411,993 and 4,196,265; Kennett et al (eds.), *Monoclonal Antibodies, Hybridomas: A New Dimension in Biological Analyses*, Plenum Press (1980); and Harlow and Lane (eds.), *Antibodies. A Laboratory Manual*, Cold Spring Harbor Laboratory Press (1988), which are incorporated herein by reference. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981) (said references incorporated by reference in their entireties). Other techniques that enable the production of antibodies through recombinant techniques (e.g., techniques described by William D. Huse et al., 1989, Science, 246: 1275-1281; L. Sastry et al., 1989, Proc. Natl. Acad. Sci. USA, 86: 5728-5732; and Michelle Alting-Mees et al., Strategies in Molecular Biology, 3: 1-9 (1990) involving a commercial system available from Stratacyte, La Jolla, Calif.) may also be utilized to construct monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a protein product of a biomarker of the invention, and once an immune response is detected, e.g., antibodies specific for the protein are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilptrack et al., 1997, Hybridoma 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting an antibody of the invention wherein, preferably, the hybridoma is generated by fusing splenocytes isolated from a mouse immunized with a protein product of a biomarker of the invention, with myeloma cells and then screening the hybridomas resulting from the fusion for hybridoma clones that secrete an antibody able to bind to the protein or protein fragment.

Antibody fragments which recognize specific epitopes of a protein product of a biomarker of the invention may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art. For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Antibodies can also be produced by a transgenic animal. In particular, human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

U.S. Pat. No. 5,849,992, for example, describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety. A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immuoglobulin. A humanized antibody comprises substantially all of at least one, and typically two, variable domains (Fab, Fab', F(ab').sub.2, Fabc, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., 2002, J. Immunol. 169:1119-25, Caldas et al., 2000, Protein Eng. 13(5):353-60, Morea et al., 2000, Methods 20(3):267-79, Baca et al., 1997, J. Biol. Chem. 272(16):10678-84, Roguska et al., 1996, Protein Eng. 9(10):895-904, Couto et al., 1995, Cancer Res. 55 (23 Supp):5973s-5977s, Couto et al., 1995, Cancer Res. 55(8):1717-22, Sandhu JS, 1994, Gene 150(2):409-10, and Pedersen et al., 1994, J. Mol. Biol. 235 (3):959-73. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.) Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety. Further, the antibodies that specifically bind to an antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438). Such antibodies can be used, alone or in combination with other therapies, in the prevention, treatment, management or amelioration of schizophrenia and/or bipolar disorder or a symptom thereof.

The invention encompasses polynucleotides comprising a nucleotide sequence encoding an antibody or fragment thereof that specifically binds to an antigen. The invention also encompasses polynucleotides that hybridize under high stringency, intermediate or lower stringency hybridization conditions to polynucleotides that encode an antibody of the invention. The polynucleotides may be obtained, and the nucleotide sequence of the polynucleotides determined, by any method known in the art. The nucleotide sequences encoding known antibodies can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

Once a polynucleotide encoding an antibody molecule, heavy or light chain of an antibody, or fragment thereof (preferably, but not necessarily, containing the heavy or light chain variable domain) of the invention has been obtained, the vector for the production of the antibody molecule may be produced by recombinant DNA technology using techniques well-known in the art.

In one preferred embodiment, monoclonal antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin (1980, Proc. Natl. Acad. Sci. USA 77:4216-4220), used with a DHFR selectable marker, e.g., as described in Kaufman and Sharp (1982, Mol. Biol. 159:601-621), lymphocytic cell lines, e.g., NS0 myeloma cells and SP2 cells, COS cells, and a cell from a transgenic animal, e.g., a transgenic mammal. For example, the cell is a mammary epithelial cell. In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr$^-$ host cells with methotrexate selection/amplification) and the neo gene (for G418 selection). In an exemplary system for recombinant expression of an antibody, or antigen-binding portion thereof, of the invention, a recombinant expression vector encoding both the antibody heavy chain and the antibody light chain is introduced into dhfr$^-$ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof, 1992, Adv. Immunol. 51:1-84; Jefferis et al., 1998, Immunol. Rev. 163:59-76). In a preferred embodiment, the Fc domain is produced in a mammalian expression system that appropriately glycosylates the residue corresponding to asparagine 297. The Fc domain can also include other eukaryotic post-translational modifications.

Once an antibody molecule has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or fragments thereof may be fused to heterologous polypeptide sequences known in the art to facilitate purification.

5.17.3 Gene Therapy Techniques

Gene therapy refers to therapy performed by the administration to a subject of an expressed or expressible nucleic acid. Any of the methods for gene therapy available in the art can be used according to the present invention. Exemplary methods are described below.

In specific embodiments, one or more antisense oligonucleotides for one or more biomarkers of the invention are administered to prevent, treat, manage or ameliorate schizophrenia and/or bipolar disorder or a symptom thereof, by way of gene therapy. In other embodiments, one or more nucleic acid molecules comprising nucleotides encoding one or more antibodies that specifically bind to one or more protein products of one or more biomarkers of the invention are administered to prevent, treat, manage or ameliorate schizophrenia and/or bipolar disorder or a symptom thereof, by way of gene therapy. In other embodiments, one or more nucleic acid molecules comprising nucleotides encoding protein products of one or more biomarkers of the invention or analogs, derivatives or fragments thereof, are administered to prevent, treat, manage or ameliorate schizophrenia and/or bipolar disorder or a symptom thereof, by way of gene therapy. In yet other embodiments, one or more nucleic acid molecules comprising nucleotides encoding one or more dominant-negative polypeptides of one or more protein products of one or more biomarker of the invention are administered to prevent, treat, manage or ameliorate schizophrenia and/or bipolar disorder or a symptom thereof, by way of gene therapy.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY. In one aspect, a composition of the invention comprises nucleic acid sequences encoding one or more antibodies that specifically bind to one or more protein products of one or more biomarkers of the invention, said nucleic acid sequences being part of expression vectors that express one or more antibodies in a suitable host. In particular, such nucleic acid sequences have promoters operably linked to the antibodies, said promoter being inducible or constitutive, and, optionally, tissue-specific.

In another aspect, a composition of the invention comprises nucleic acid sequences encoding dominant-negative polypeptides of one or protein products of one or more biomarkers of the invention, said nucleic acid sequences being part of expression vectors that express dominant-negative polypeptides in a suitable host. In particular, such nucleic acid sequences have promoters operably linked to the dominant-negative polypeptides, said promoter being inducible or constitutive, and, optionally, tissue-specific. In another particular embodiment, nucleic acid molecules are used in which the dominant-negative coding sequences and any other desired sequences are flanked by regions that promote homologous recombination at a desired site in the genome, thus providing for intrachromosomal expression of the dominant-negative nucleic acids (Koller and Smithies, 1989, Proc. Natl. Acad. Sci. USA 86:8932-8935; Zijlstra et al., 1989, Nature 342: 435-438).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequence is directly administered in vivo, where it is expressed to produce the encoded product. This can be accomplished by any of numerous methods known in the art, e.g., by constructing it as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., International Publication Nos. WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO 93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijistra et al., 1989, Nature 342:435-438).

For example, a retroviral vector can be used. These retroviral vectors have been modified to delete retroviral sequences that are not necessary for packaging of the viral genome and integration into host cell DNA. The nucleic acid sequences encoding the antibodies of interest, or proteins of interest or fragments thereof to be used in gene therapy are cloned into one or more vectors, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang, et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) and/or schizophrenia and/or bipolar disorder cells are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, schizophrenia and/or bipolar disorder cells, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In one embodiment in which recombinant cells are used in gene therapy, nucleic acid sequences encoding antibodies of interest, or proteins of interest or fragments thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., International Publication No. WO 94/08598, dated Apr. 28, 1994; Stemple and Anderson, 1992, Cell 71:973-985; Rheinwald, 1980, Meth. Cell Bio. 21A:229; and Pittelkow and Scott, 1986, Mayo Clinic Proc. 61:771).

Promoters that may be used to control the expression of nucleic acid sequences encoding antibodies of interest, proteins of interest or fragments thereof may be constitutive, inducible or tissue-specific. Non-limiting examples include the SV40 early promoter region (Bemoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42); prokaryotic expression vectors such as the β-lactamase promoter (VIIIa-Kamaroff et al., 1978, Proc. Natl. Acad. Sci. USA 75:3727-3731), or the tac promoter (DeBoer et al., 1983, Proc. Natl. Acad. Sci. USA 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.18 Pharmaceutical Compositions

Biologically active compounds identified using the methods of the invention or a pharmaceutically acceptable salt thereof can be administered to a patient, preferably a mammal, more preferably a human, suffering from schizophrenia or bipolar disorder. In a specific embodiment, a compound or pharmaceutically acceptable salt thereof is administered to a patient, preferably a mammal, more preferably a human, suffering from schizophrenia or bipolar disorder: In another embodiment, a compound or a pharmaceutically acceptable salt thereof is administered to a patient, preferably a mammal, more preferably a human, as a preventative measure against schizophrenia and/or bipolar disorder. In accordance with these embodiments, the patient may be a child, an adult or elderly, wherein a "child" is a subject between the ages of 24 months of age and 18 years of age, an "adult" is a subject 18 years of age or older, and "elderly" is a subject 65 years of age or older.

When administered to a patient, the compound or a pharmaceutically acceptable salt thereof is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In a specific embodiment, a compound is administered locally to one or more sections of the brain affected by schizophrenia and/or bipolar disorder.

In certain embodiments, it may be desirable to introduce the compound or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound and pharmaceutically acceptable salts thereof can be formulated as a suppository, with traditional binders and vehicles such as triglycerides. In another embodiment, the compound and pharmaceutically acceptable salts thereof can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compound and pharmaceutically acceptable salts thereof can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

The compounds described herein can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of interest. Such methods comprise formulating a pharmaceutically acceptable carrier with an agent that modulates expression or activity of a polypeptide or nucleic acid of interest. Such compositions can further include additional active agents. Thus, the invention further includes methods for preparing a pharmaceutical composition by formulating a pharmaceutically acceptable carrier with an agent that modulates expression or activity of a polypeptide or nucleic acid of interest and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Intravenous administration is preferred. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (more preferably, 0.1 to 20 mg/kg, 0.1-10 mg/kg, or 0.1 to 1.0 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. (1997, J. Acquired Immune Deficiency Syndromes and Human Retrovirology 14:193).

In a specific embodiment, an effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 0.1 to 1.0 mg/kg, 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In addition to those compounds described above, the present invention encompasses the use of small molecules that modulate expression or activity of a nucleic acid or polypeptide of interest. Non-limiting examples of small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to a subject (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

5.18 Kits

The present invention provides kits for measuring the expression of the protein and RNA products of at least 1, at least 2, at least 3, at least 4, at least 5, at least 6, at least 7, at least 8, at least 9, at least 10, at least 12, at least 15, at least 20, at least 25, or all or any combination of the biomarkers of the invention. Such kits comprise materials and reagents required for measuring the expression of such protein and RNA products. In specific embodiments, the kits may further comprise one or more additional reagents employed in the various methods, such as: (1) reagents for purifying RNA from blood; (2) primers for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization and washing buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA isolated from a sample (e.g., blood) for use as a control.

In some embodiments, the kits are RT-PCR kits. In other embodiments, the kits are nucleic acid arrays and protein arrays. Such kits according to the subject invention will at least comprise an array having associated protein or nucleic acid members of the invention and packaging means therefore. Alternatively the protein or nucleic acid members of the invention may be prepackaged onto an array.

In some embodiments, the kits are Quantitative RT-PCR kits. In one embodiment, the quantitative RT-PCR kit includes the following: (a) primers used to amplify each of a combination of biomarkers of the invention; (b) buffers and enzymes including an reverse transcripate; (c) one or more thermos table polymerases; and (d) Sybr® Green. In a preferred embodiment, the kit of the invention also includes (a) a reference control RNA and (b) a spiked control RNA.

The invention provides kits that are useful for diagnosing schizophrenia and/or bipolar disorder. For example, in a particular embodiment of the invention a kit is comprised a forward and reverse primer wherein the forward and reverse primer are designed to quantitate expression of all of the species of mRNA corresponding to each of the biomarkers as identified in Table 2. In certain embodiments, at least one of the primers is designed to span an exon junction.

The invention provides kits that are useful for detecting, diagnosing, monitoring and prognosing schizophrenia and/or bipolar disorder based upon the expression of protein or RNA products of at least 1, at least 2, at least 3, at least 4, at least 5, at least 6, at least 7, or all or any combination of the biomarkers of the invention in a sample. In certain embodiments, such kits do not include the materials and reagents for measuring the expression of a protein or RNA product of a biomarker of the invention that has been suggested by the prior art to be associated with schizophrenia and/or bipolar disorder. In other embodiments, such kits include the materials and reagents for measuring the expression of a protein or RNA product of a biomarker of the invention that has been suggested by the prior art to be associated with schizophrenia and/or bipolar disorder and at least 1, at least 2, at least 3, at least 4, at least 5, at least 6, at least 7, or more genes other than the biomarkers of the invention.

The invention provides kits useful for monitoring the efficacy of one or more therapies that a subject is undergoing based upon the expression of a protein or RNA product of at least 1, at least 2, at least 3, at least 4, at least 5, at least 6, at least 7, or all or any combination of the biomarkers of the invention in a sample. In certain embodiments, such kits do not include the materials and reagents for measuring the expression of a protein or RNA product of a biomarker of the invention that has been suggested by the prior art to be associated with schizophrenia and/or bipolar disorder. In other embodiments, such kits include the materials and reagents for measuring the expression of a protein or RNA product of a biomarker of the invention that has been suggested by the prior art to be associated with schizophrenia and/or bipolar disorder and at least 1, at least 2, at least 3, at least 4, at least 5, at least 6, at least 7, or more genes other than the biomarkers of the invention.

The invention provides kits using for determining whether a subject will be responsive to a therapy based upon the expression of a protein or RNA product of at least 1, at least 2, at least 3, at least 4, at least 5, at least 6, at least 7, or all or any combination of the biomarkers of the invention in a sample. In certain embodiments, such kits do not include the materials and reagents for measuring the expression of a protein or RNA product of a biomarker of the invention that has been suggested by the prior art to be associated with schizophrenia and/or bipolar disorder. In other embodiments, such kits include the materials and reagents for measuring the expression of a protein or RNA product of a biomarker of the invention that has been suggested by the prior art to be associated with schizophrenia and/or bipolar disorder and at least 1, at least 2, at least 3, at least 4, at least 5, at least 6, at least 7, or more genes other than the biomarkers of the invention.

The invention provides kits for measuring the expression of a RNA product of at least 1, at least 2, at least 3, at least 4, at least 5, at least 6, at least 7, or all or any combination of the biomarkers of the invention in a sample. In a specific embodiment, such kits comprise materials and reagents that are necessary for measuring the expression of a RNA product of a biomarker of the invention. For example, a microarray or RT-PCR kit may be produced for schizophrenia and/or bipolar disorder and contain only those reagents and materials necessary for measuring the levels of RNA products of at least 1, at least 2, at least 3, at least 4, at least 5, at least 6, at least 7, or all or any combination of the biomarkers of the invention. Alternatively, in some embodiments, the kits can comprise materials and reagents that are not limited to those required to measure the levels of RNA products of 1, 2, 3, 4, 5, 6, 7 or all or any combination of the biomarkers of the invention. For example, a microarray kit may contain reagents and materials necessary for measuring the levels of RNA products of not necessarily associated with or indicative of schizophrenia and/or bipolar disorder, in addition to reagents and materials necessary for measuring the levels of the RNA products of at least 1, at least 2, at least 3, at least 4, at least 5, at least 6, at least 7, or all or any combination of the biomarkers of the invention. In a specific embodiment, a microarray or RT-PCR kit contains reagents and materials necessary for measuring the levels of RNA products of at least 1, at least 2, at least 3, at least 4, at least 5, at least 6, at least 7, or all or any combination of the biomarkers of the invention, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes other than the biomarkers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, 500-1000 other genes than the biomarkers of the invention.

For nucleic acid micoarray kits, the kits generally comprise probes attached to a support surface. The probes may be labeled with a detectable label. In a specific embodiment, the probes are specific for an exon(s), an intron(s), an exon junction(s), or an exon-intron junction(s)), of RNA products of 1, 2, 3, 4, 5, 6, 7, all or any combination of the biomarkers of the invention. The microarray kits may comprise instructions for performing the assay and methods for interpreting and analyzing the data resulting from the performance of the assay. In a specific embodiment, the kits comprise instructions for diagnosing schizophrenia and/or bipolar disorder. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For RT-PCR kits, the kits generally comprise pre-selected primers specific for particular RNA products (e.g., an exon(s), an intron(s), an exon junction(s), and an exon-intron junction(s)) of 1, 2, 3, 4, 5, 6, 7, or all or any combination of the biomarkers of the invention. The RT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for RNA products of 1, 2, 3, 4, 5, 6, 7, or all or any combination of the biomarkers of the invention. The probes may or may not be labeled with a detectable label (e.g., a fluorescent label). Each component of the RT-PCR kit is generally in its own suitable container. Thus, these kits generally comprise distinct containers suitable for each individual reagent, enzyme, primer and probe. Further, the RT-PCR kits may comprise instructions for performing the assay and methods for interpreting and analyzing the data resulting from the performance of the assay. In a specific embodiment, the kits contain instructions for diagnosing schizophrenia and/or bipolar disorder.

In a specific embodiment, the kit is a real-time RT-PCR kit. Such a kit may comprise a 96 well plate and reagents and materials necessary for SYBR Green detection. The kit may comprise reagents and materials so that beta-actin can be used to normalize the results. The kit may also comprise controls such as water, phospate buffered saline, and phage MS2 RNA. Further, the kit may comprise instructions for performing the assay and methods for interpreting and analyzing the date resulting from the performance of the assay. In a specific embodiment, the instructions state that the level of a RNA product of 1, 2, 3, 4, 5, 6, 7, all or any combination of the biomarkers of the invention should be examined at two concentrations that differ by, e.g., 5 fold to 10-fold.

For antibody based kits, the kit can comprise, for example: (1) a first antibody (which may or may not be attached to a support) which binds to protein of interest (e.g., a protein product of 1, 2, 3, 4, 5, 6, 7, all or any combination of the biomarkers of the invention); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for diagnosing schizophrenia and/or bipolar disorder.

5.19 SNPs

A Single Nucleotide Polymorphism (SNP) is a single nucleotide variation at a specific location in the genome of different individuals. SNPs are found in both coding and non-coding regions of genomic DNA. In spite of the paucity of scorable phenotypes, SNPs are found in large numbers throughout the human genome (Cooper et al., Hum Genet. 69:201-205, 1985). SNPs are stable genetic variations frequently found in genes, and contribute to the wide range of phenotypic variations found in organisms. Single nucleotide polymorphisms (SNPs) can be of predictive value in identifying many genetic diseases, as well as phenotypic characteristics. It is known for example that certain SNPs result in disease-causing mutations such as the SNP correlated with heritable breast cancer (Cannon-Albright and Skolnick, Semin Oncol 23:1-5, 1996).

A SNP may be identified in the DNA of an organism by a number of methods well known to those of skill in the art, including but not limited to identifying the SNP by DNA sequencing, by amplifying a PCR product and sequencing the PCR product, by Oligonucleotide Ligation Assay (OLA), by Doublecode OLA, by Single Base Extension Assay, by allele specific primer extension, or by mismatch hybridization.

The instant invention offers a more focused and efficient method of screening SNPs to identify those SNPs which are specifically associated with schizophrenia and/or bipolar disorder by having identified a selection of genes which are differentially expressed in blood from individuals having schizophrenia and/or bipolar disorder. In one aspect of the invention, a selection of SNPs to be screened are those SNPs found in the genes listed in Tables 1 and 3. In another aspect of the invention, the SNPs to be screened are those SNPs listed in FIG. 3. In yet another aspect of the invention, novel SNPs can be identified in the disease-associated biomarkers using those methods listed above.

In particular, this invention focuses on methods for identifying those SNPs which are associated with schizophrenia and/or bipolar disorder by screening only those SNPs in the biomarkers identified herein. Those SNPs which are identified using the methods disclosed herein will be convenient diagnostic markers. One preferred aspect of identifying schizophrenia and/or bipolar disorder associated SNPs encompasses isolating DNA from a sample such as blood from a population of individuals, some of said individuals having been diagnosed with schizophrenia and/or bipolar disorder, some of those individuals not having schizophrenia and/or bipolar disorder, and screening the genes for the SNPs identified in FIG. 3 to identify one or more SNPs as diagnostic markers of schizophrenia and/or bipolar disorder. More specifically a SNP is considered to be a schizophrenia and/or bipolar disorder associated snp if those individuals having schizophrenia and/or bipolar disorder have a different polymorphism at the SNP locus than those individuals not having schizophrenia and/or bipolar disorder. Further, a particular SNP is considered to be diagnostic for schizophrenia and/or bipolar disorder if a particular polymorphism of the snp is found to present at a statistically significant higher frequency in those individuals having schizophrenia and/or bipolar disorder than in those individuals not having schizophrenia and/or bipolar disorder. Indices of statistical significance include $p<0.05$, $p<0.001$, $p<0.01$, and $p<0.10$. However this invention is not limited to identifying schizophrenia and/or bipolar disorder diagnostic SNPs from FIG. 3, and includes methods of identifying new SNPs in the schizophrenia and/or bipolar disorder biomarker genes listed in Tables 1 and 2, and methods of determining their diagnostic value with respect to schizophrenia and/or bipolar disorder.

As would be understood, a preferred sample is blood, but these methods encompass any samples from which DNA can be obtained including epithelial cells, buccal cells, hair, saliva, tissue cells and the like. There are a variety of available methods for obtaining and storing tissue and/or blood samples. These alternatives allow tissue and blood samples to be stored and transported in a form suitable for the recovery of genomic DNA from the samples for genotype analysis. DNA samples can be collected and stored on a variety of solid mediums, including Whatmann paper, Guthrie cards, tubes, swabs, filter paper, slides, or other containers. When whole blood is collected on filter paper, for example, it can be dried and stored at room temperature.

In another aspect of the invention, schizophrenia and/or bipolar disorder associated SNPs can be identified from RNA transcripts of the schizophrenia and/or bipolar disorder biomarker genes, listed in Tables 1, instead of from genomic DNA. In one embodiment, RNA is isolated from a sample such as blood, from individuals with and without the given disease or disorder, and transcripts encoded by these schizophrenia and/or bipolar disorder biomarker genes are reversed transcribed into cDNA. The cDNA is amplified and analyzed to determine the presence of SNPs in the schizophrenia and/or bipolar disorder biomarker genes. A schizophrenia and/or bipolar disorder associated snp, can be identified by then comparing the distribution of each of the SNPs identified in the schizophrenia and/or bipolar disorder associated biomarker gene(s) differentially expressed in those individuals having schizophrenia and/or bipolar disorder, with those of individuals who do not have schizophrenia and/or bipolar disorder. In a further variation of this embodiment, instead analyzing cDNA for the presence of SNPs, the RNA transcripts of the disease specific biomarker genes, or their amplified products, are analyzed for the presence of SNPs.

Analysis of genomic DNA comprising the schizophrenia and/or bipolar disorder biomarker genes has the potential to identify SNPs in the coding region as well as in regulatory regions, the latter which may contribute to the change in expression levels of the gene. Analysis of cDNA encoded SNPs has the potential to identify only SNPs in the coding region of the schizophrenia and/or bipolar disorder biomarker genes, which may be instrumental in deciphering protein based mechanisms of schizophrenia and/or bipolar disorder. Methods of analyzing cDNA encoded SNPs can be carried out by analyzing the cDNA generated in the rt-PCR reactions described herein that are used to identify the level of the biomarker in samples from patients and non patients.

A schizophrenia and/or bipolar disorder associated SNP may be identified in the DNA of the schizophrenia and/or bipolar disorder biomarker genes by a number of methods well known to those of skill in the art, (see for example U.S. Pat. Nos. 6,221,592 and 5,679,524), including but not limited to identifying the SNP by PCR or DNA amplification, Oligonucleotide Ligation Assay (OLA) (Landegren et al., Science 241:1077, 1988), Doublecode OLA, mismatch hybridization, mass spectrometry, Single Base Extension Assay, (U.S. Pat. No. 6,638,722), RFLP detection based on allele-specific restriction-endonuclease cleavage (Kan and Dozy, Lancet ii:910-912, 1978), hybridization with allele-specific oligonucleotide probes (Wallace et al., Nucl Acids Res 6:3543-3557, 1978), including immobilized oligonucleotides (Saiki et al., Proc Natl Acad Sci USA 86:6230-6234, 1989) or oligonucleotide arrays (Maskos and Southern, Nucl Acids Res 21:2269-2270, 1993), allele-specific PCR (Newton et al., Nucl Acids Res 17:2503-16, 1989), mismatch-repair detection (MRD) (Faham and Cox, Genome Res 5:474-482, 1995), binding of MutS protein (Wagner et al., Nucl Acids Res 23:3944-3948, 1995), single-strand-conformation-polymorphism detection (Orita et al., Genomics 5:874-879, 1983), RNAase cleavage at mismatched base-pairs (Myers et al., Science 230:1242, 1985), chemical (Cotton et al., Proc Natl Acad Sci USA 85:4397-4401, 1988) or enzymatic (Youil et al., Proc Natl Acad Sci USA 92:87-91, 1995) cleavage of heteroduplex DNA, methods based on allele specific primer extension (Syvanen et al., Genomics 8:684-692, 1990), genetic bit analysis (GBA) (Nikiforov et al., Nucl Acids Res 22:4167-4175, 1994), and radioactive and/or fluorescent DNA sequencing using standard procedures well known in the art.

The instant methods of screening a subset of SNPs to identify schizophrenia and/or bipolar disorder associated smps in schizophrenia and/or bipolar disorder biomarker genes also encompass non-PCR methods of DNA. These methods include ligase chain reaction ("LCR"), disclosed in European Patent Application No. 320,308, Qbeta Replicase, described in PCT Patent Application No. PCT/US87/00880, isothermal amplification methods, Walker et al. (Nucleic Acids Res 20(7):1691-6, 1992), Strand Displacement Amplification (SDA) described in U.S. Pat. Nos. 5,712,124, 5,648,211 and 5,455,166, Cyclic Probe Reaction, Transcription-Based Amplification, including nucleic acid sequence based amplification (NASBA) and 3SR, Kwoh et al., Proc Natl Acad Sci USA, 86:1173-77, 1989; PCT Patent Application WO 88/10315 et al., 1989, other amplification methods, as described in British Patent Application No. GB 2,202,328, and in PCT Patent Application No. PCT/US89/01025, Davey et al., European Patent Application No. 329,822, Miller et al., PCT Patent Application WO 89/06700, "race and "one-sided PCR TM." described in Frohman, In: PCR Protocols: A Guide To Methods And Applications, Academic Press, N.Y., 1990, methods based on ligation of two (or more) oligonucleotides in the presence of nucleic acid having the sequence of the resulting "di-oligonucleotide, described in Wu et al., Genomics 4:560-569, 1989.

While it is generally contemplated that the polymerase employed will be thermostable, non-thermostable polymerases may also be employed in the context of the present disclosure. Exemplary polymerases and nucleic acid modifying enzymes that may be used in the context of the disclosure include the thermostable DNA Polymerases of OmniBase Sequencing Enzyme, Pfu DNA Polymerase, Taq DNA Polymerase, Taq DNA Polymerase, Sequencing Grade, TaqBead Hot Start Polymerase, AmpliTaq Gold, Vent DNA Polymerase, Tub DNA Polymerase, TaqPlus DNA Polymerase, Tfl DNA Polymerase, Tli DNA Polymerase, Tth DNA Polymerase; the DNA Polymerases of DNA Polymerase I, Klenow Fragment, Exonuclease Minus, DNA Polymerase I, DNA Polymerase I Large (Klenow) Fragment, Terminal Deoxynucleotidyl Transferase, T7 DNA Polymerase, T4 DNA Polymerase; the Reverse trancriptases of AMV Reverse Transcriptase and M-MLV Reverse Transcriptase; T4 DNA ligase and T4 polynucleotide kinase.

Recognition moieties incorporated into primers, incorporated into the amplified product during amplification, or attached to probes are useful in the identification of the amplified molecules. A number of different labels may be used for this purpose such as, for example: fluorophores, chromophores, radio-isotopes, enzymatic tags, antibodies, chemiluminescence, electroluminescence, affinity labels, etc. One of skill in the art will recognize that these and other fluorophores not mentioned herein can also be used with success in this disclosure. Examples of affinity labels include but are not limited to the following: an antibody, an antibody fragment, a receptor protein, a hormone, biotin, DNP, or any polypeptide/protein molecule that binds to an affinity label and may be used for separation of the amplified gene. Examples of enzyme tags include enzymes such as urease, alkaline phosphatase, or peroxidase. Additionally, colorimetric indicator substrates can be employed to provide a detection means visible to the human eye or spectrophotometrically, to identify specific hybridization with complementary nucleic acid-containing samples. All these examples are generally known in the art and the skilled artisan will recognize that the present disclosure is not limited to the examples described above. The following fluorophores are specifically contemplated to be useful in the present disclosure: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

In the context of the present disclosure, it is specifically contemplated that the DNA amplification products of the disclosed methods may be analyzed using DNA chips or microarrays in order to detect SNPs. The amplified DNA products may then be passed over a DNA chip or microarray encompassing oligonucleotide or polynucleotide probes. The ability or inability of the amplified DNA to hybridize to the microarray or DNA chip will facilitate the characterization of the SNPs present in the biomarker genes encoding the transcripts present in the sample.

The examples below are non-limiting and are merely representative of various aspects and features of the present invention.

5.19 EXAMPLES

Example 1

RNA Isolation from Lysed Blood 10 ml whole blood is obtained in a Vacutainer and spun at 2,000 rpm for 5 min at 4° C. and the plasma layer removed. Lysis Buffer is added to blood sample in a ratio of 3 parts Lysis Buffer to 1 part blood (Lysis Buffer (IL) 0.6 g EDTA; 1.0 g $KHCO_2$, 8.2 g $NH_4Cl$ adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol® (GIBCO/BRL) in a ratio of approximately 6 ml of TRIzol® for every 10 ml of the original blood sample and vortexed well. Samples are left for 5 minutes at room temperature. RNA is extracted using 1.2 ml of chloroform per 1 ml of TRIzol®. Sample is centrifuged at 12,000×g for 5 minutes at 4° C. and upper layer is collected. To upper layer, isopropanol is added in ratio of 0.5 ml per 1 ml of TRIzol®. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

Example 2

From Whole Blood 100 ul whole blood is obtained in a microcentrifuge tube and spun at 2,000 rpm (800 g) for 5 min at 4° C. and the supernatant removed. Pelleted cells are homogenized using TRIzol (GIBCO/BRL) in a ratio of approximately 6 μl of TRIzol for every 10 μl of the original blood sample and vortexed well. Samples are left for 5 minutes at room temperature. RNA is extracted using 12 μL of chloroform per 10 μl of TRIzol. Sample is centrifuged at 12,000×g for 5 minutes at 4° C. and upper layer is collected. To upper layer, isopropanol is added in ratio of 5 μl per 10 μl of TRIzol. Sample is left overnight at −20° C. or for one hour at −20° C. RNA is pelleted in accordance with known methods, RNA pellet air dried, and pellet resuspended in DEPC treated ddH2O. RNA samples can also be stored in 75% ethanol where the samples are stable at room temperature for transportation.

From Centrifuged Lysed Blood 10 ml whole blood is obtained in a Vacutainer and spun at 2,000 rpm (800 g) for 5 min at 4° C. and the plasma layer removed. Lysis Buffer is added to blood sample in a ratio of 3 parts Lysis Buffer to 1 part blood (Lysis Buffer (IL) 0.6 g EDTA; 1.0 g KHCO2, 8.2 g NH4Cl adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol (GIBCO/BRL) in a ratio of approximately 6 ml of TRIzol for every 10 ml of the original blood sample and vortexed well. Samples are left for 5 minutes at room temperature. RNA is extracted using 1.2 ml of chloroform per 1 ml of TRIzol. Sample is centrifuged at 12,000×g for 5 minutes at 4° C. and upper layer is collected. To upper layer, isopropanol is added in ratio of 0.5 ml per 1 ml of TRIzol. Sample is left overnight at −20° C. or for one hour at −20° C. RNA is pelleted in accordance with known methods, RNA pellet air dried, and pellet resuspended in DEPC treated ddH2O. RNA samples can also be stored in 75% ethanol where the samples are stable at room temperature for transportation.

From Serum Free Whole Blood 10 ml whole blood is obtained in a Vacutainer and spun at 2,000 rpm (800 g) for 5 min at 4° C. and the plasma layer removed. Pelleted cells are homogenized using TRIzol (GIBCO/BRL) in a ratio of approximately 6 ml of TRIzol for every 10 ml of the original blood sample and vortexed well. Samples are left for 5 minutes at room temperature. RNA is extracted using 1.2 ml of chloroform per 1 ml of TRIzol. Sample is centrifuged at 12,000×g for 5 minutes at 4° C. and upper layer is collected. To upper layer, isopropanol is added in ratio of 0.5 ml per 1 ml of TRIzol. Sample is left overnight at −20° C. or for one hour at −20° C. RNA is pelleted in accordance with known methods, RNA pellet air dried, and pellet resuspended in DEPC treated ddH2O. RNA samples can also be stored in 75% ethanol where the samples are stable at room temperature for transportation.

Example 3

Target Nucleic Acid Preparation and Hybridization

Preparation of Fluorescent DNA Probe from mRNA

Fluorescently labeled target nucleic acid samples of RNA are prepared for analysis with an array of the invention.

1 μg Oligo-dT primers are annealed to 10 ug of total RNA isolated from blood from patient diagnosed with schizophrenia and/or bipolar disorder or suspected of having schizophrenia and/or bipolar disorder in a total volume of 10 ul, by heating to 70° C. for 10 min, and cooled on ice. The mRNA is reverse transcribed by incubating the sample at 42° C. for 40 min in a 25 μl volume containing a final concentration of 50 mM Tris-HCl (pH 8.3), 75 mM KCl, 3 mM MgCl2, 25 mM DTT, 25 mM unlabeled dNTPs, 400 units of Superscript II (200 U/uL, Gibco BRL), and 15 mM of Cy3 or Cy5 (Amersham). The reaction is stopped by the addition of 2.5 μl of 55500 mM EDTA and 5 μl of 1M NaOH, and incubation at 65° C. for 10 min. The reaction mixture is neutralized by addition of 12.5 μl of 1M Tris HCl (pH7.6).

The labeled target nucleic acid sample is purified by centrifugation in a Centricon-30 micro-concentrator (Amicon). If two different target nucleic acid samples (e.g., two samples derived from different patients) are being analyzed and compared by hybridization to the same array, each target nucleic acid sample is labeled with a different fluorescent label (e.g., Cy3 and Cy5) and separately concentrated. The separately concentrated target nucleic acid samples (Cy3 and Cy5 labeled) are combined into a fresh centricon, washed with 500 μl TE, and concentrated again to a volume of less than 7 μl. 1 μL of 10 μg/μl polyA RNA (Sigma, #P9403) and 1 μl of 10 μg/ul tRNA (Gibco-BRL, #15401-011) is added and the volume is adjusted to 9.5 μl with distilled water. For final target nucleic acid preparation 2.1 μl 20×SSC (1.5M NaCl, 150 mM NaCltrate (pH8.0)) and 0.35 μl 10% SDS is added.

Hybridization

Labeled nucleic acid is denatured by heating for 2 min at 100° C., and incubated at 37° C. for 20-30 min before being placed on a nucleic acid array under a 22 mm×22 mm glass cover slip. Hybridization is carried out at 65° C. for 14 to 18 hours in a custom slide chamber with humidity maintained by a small reservoir of 3×SSC. The array is washed by submersion and agitation for 2-5 min in 2×SSC with 0.1% SDS, followed by 1×SSC, and 0.1×SSC. Finally, the array is dried by centrifugation for 2 min in a slide rack in a Beckman GS-6 tabletop centrifuge in Microplus carriers at 650 RPM for 2 min.

Example 4

Real Time RT PCR

Real time RT PCR was performed on the genes as disclosed in Table 1 using the SYBR® Green Kit from Qiagen (Product Number 204143). The experimental results of these genes are shown in Example 6 below.

Either a one step (reverse transcription and PCR combined) or a two step (reverse transcription first and then subsequent PCR) can be used. In the case of the two step protocol, reverse transcription was first performed using the High-Capacity cDNA Archive Kit from Applied Biosystems (Product number 4322171) and following the protocol utilized therein.

More specifically purified RNA as described previously herein was incubated with Reverse Transcriptase buffer, dNTPs, Random primers and Reverse transcriptase and incubated for 25° C. for 10 minutes and subsequently for 37° C. for two hours and the resulting mixture utilized as the starting product for quantitative PCR.

cDNA resulting from reverse transcription was incubated with the QuantiTect SYBR® Green PCR Master Mix as provided and no adjustments were made for magnesium concentration. Uracil-N-Glycosylase was not added. 5 μM of both forward primer and reverse primer specific to the genes of the invention were added and the reaction was incubated and monitored in accordance with the standard protocol utilizing the ABI PRISM 7700/ABI GeneAmp 5700/iCycler/DNA Engine Opticon.

TABLE 8

Primers used in the performance of Real Time RT PCR

| Gene | Forward Primer | Primer Position | Reverse Primer | Primer Position |
|---|---|---|---|---|
| ADSS | CTGCGTTGGCACTTACCAAGTT SEQ ID NO 1 | 1361 | GACTTCTTGGTTTGCTGGGA SEQ ID NO 2 | 1476 |
| APOBEC3B | CTCAGATACCTGATGGATCCAGACACA SEQ ID NO 3 | 619 | CGCTCCACCTCATAGCACAAGT SEQ ID NO 4 | 719 |
| ATM | TGTGGATGGCATGGGCATTA SEQ ID NO 5 | 8931 | GAAGGACCTCTACAATGGTTAACAGAG SEQ ID NO 6 | 9046 |
| CLC | GCCAGATAAGTACCAGGTAATGG SEQ ID NO 7 | 364 | ATCTCTCCACACTTGCACCA SEQ ID NO 8 | 463 |
| CTBP1 | ATCACAGGCCGGATCCCAGA SEQ ID NO 9 | 1150 | ATTGAGCTCAGGGTGCACGA SEQ ID NO 10 | 1174 |
| CXCL1 | ACCGAAGTCATAGCCACACT SEQ ID NO 11 | 293 | GTTGGATTTGTCACTGTTCAGC SEQ ID NO 12 | 400 |
| DATF1 | AGCAGAAGTCTAGCGAAGACCAAG SEQ ID NO 13 | 1575 | GCCTCTATCACAGGCTGGAA SEQ ID NO 14 | 1677 |
| S100A9 | TTTGGGACAGAGTGCAAGACGA SEQ ID NO 15 | 25 | CCAGCTTCACAGAGTATTGGTGGA SEQ ID NO 16 | 124 |

Example 5

Taqman®

Quantitative real time RT PCR can also be performed using the QuantiTect™ Probe RT-PCR system from Qiagen (Product Number 204343) in conjunction with a TaqMan® dual labelled probe and primers corresponding to the gene of interest. The TaqMan® probe and primers can be ordered from Applied Biosystems Assays-On-Demand™.

The dual labelled probe contains both a fluorophore and a quencher molecule. The proximity of the fluorescent reporter with the quencher prevents the reporter from fluorescing, but during the PCR extension step, the 5'-3' exonuclease activity of the Taq DNA polymerase releases the fluorophore which allows it to fluoresce. As such, the amount of fluorescence correlates with the amount of PCR product generated.

Example 6

Statistical Analysis of Real Time PCR Results

Real Time PCR was performed to analyze potential biomarkers from blood samples isolated from individuals categorized as normal (not having schizophrenia or bipolar disorder), having schizophrenia or having bipolar disorder. T-tests and or Mann Whitney tests were utilized on age and sex matched sample sets of approximately 16-25 in size. FIG. 1 shows analysis for the eight biomarkers on total RNA isolated from centrifuged lysed blood for each biomarkers ability to differentiate as between: (a) schizophrenia and non-schizophrenia (b) bipolar disorder and non-bipolar disorder and (c) schizophrenia and bipolar disorder. Biomarkers which demonstrated an ability to differentiate with a p value of less than 0.05 are shaded.

Example 7

Identification of Combinations of Biomarkers Using Logistic Regression

Figure 6:
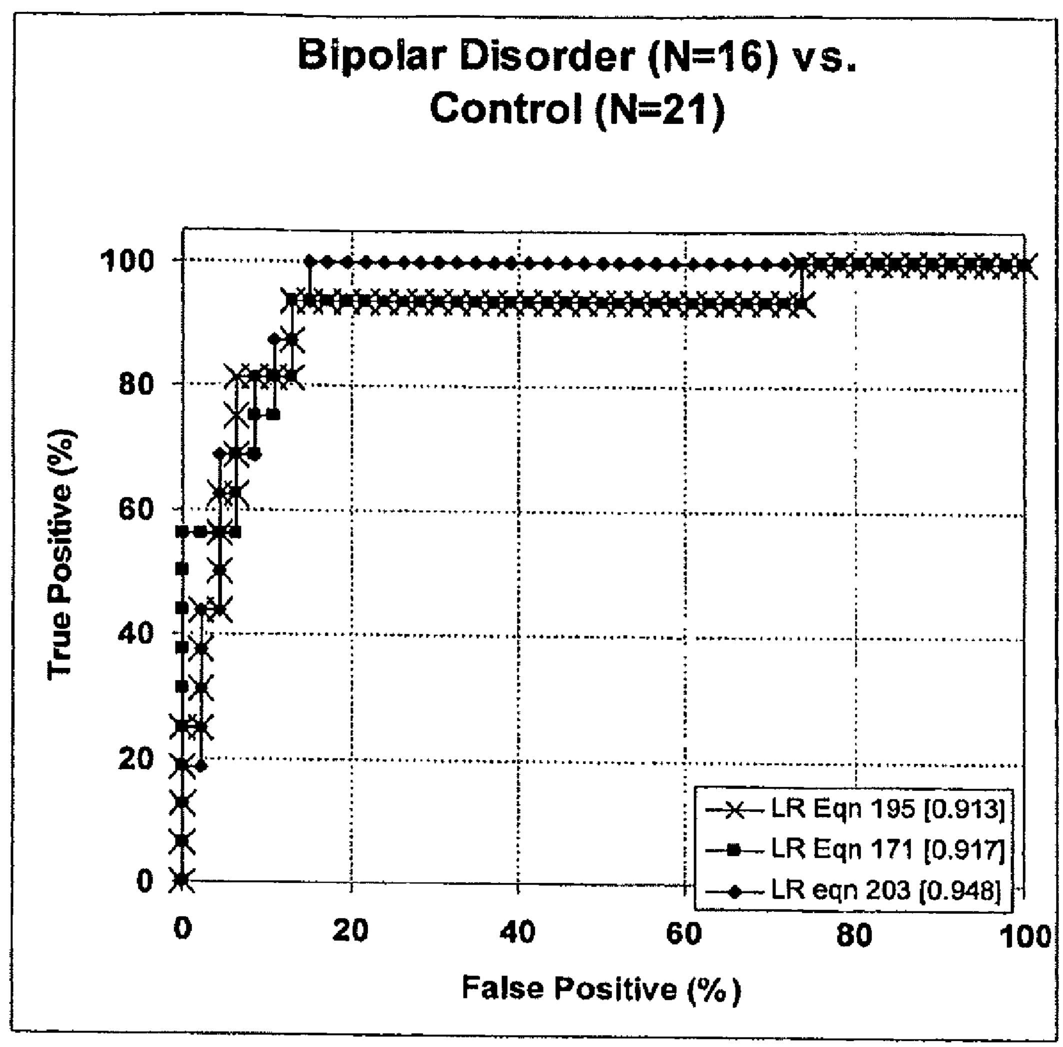
FIG. 6 is an is an example of a number of classifiers generated for use in differentiating as between bipolar disorder and normal (non bipolar disorder) with an ROC of >0.9.
Figure 7:
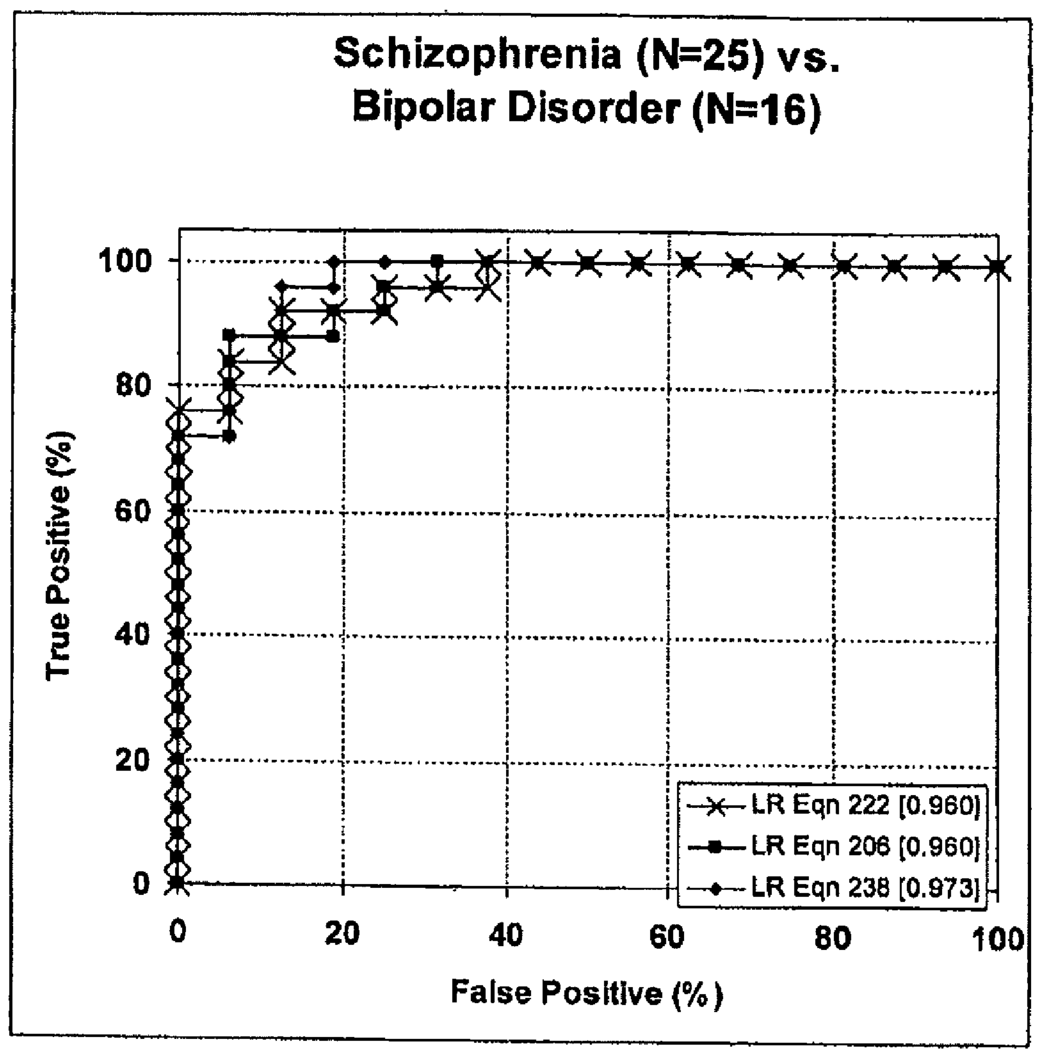
FIG. 7 is an is an example of a number of classifiers generated for use in differentiating as between bipolar disorder and schizophrenia with an ROC of >0.9.

First strand cDNA synthesis was performed on a Perkin-Elmer DNA Thermal Cycler using the ABI High Capacity cDNA Archive Kit (Cat #4322171). Quantitation of specific cDNA was achieved with the Qiagen Quantitect SYBR® Green PCR Kit (Cat #204143) with confirmation of desired product using agarose gel. In each sample, the expression level of a target gene was quantified by its Ct-value, the concentration-dependent PCR cycle number at which the amplicon becomes distinguishable over background. Each Ct-value was related to an internal standard by subtracting the Ct value of beta-actin as a housekeeping gene. To obtain increased discriminating ability, logistic regression was used to generate linear combinations of Δ Ct for (a) schizophrenia v. control (b) bipolar disorder v. control and (c) schizophrenia v. bipolar disorder. The diagnostic accuracy of the combinations (ie the probably of true vs. false positive and true v. false negative calls) was quantitatively evaluated by ROC (Receiver Operating Characteristic) curve analysis using MedCalc®, (MedCalc; Mariakerke, Belgium); XLSTAT® (AddinSoft; Paris, France) and our own software. ROC analysis of the classifiers generated using logistic regression were analyzed. Examples of classifiers for (a) schizophrenia v. control with an ROC of >0.9 are shown in FIG. 5. Examples of classifiers for (b) bipolar disorder v. control with an ROC of >0.9 are shown in FIG. 6. Examples of classifiers for (c) bipolar disorder v. schizophrenia with an ROC of >0.9 are shown in FIG. 7.

Example 8

Diagnosis of Individual Utilizing Classifiers of the Invention

Classifiers of the invention can be generated as described in Example 8 above or using other mathematical models as described herein. For example one of the classifiers identified for differentiating between schizophrenia and non-schizophrenia as shown in FIG. 5 is written as follows:

X=−27.66-1.2*APOBEC3B+4.69*ADSS−4.04*ATM−1.66*CLC+4.68*CTBP1−1.58*CXCL1+3.18*DATF1−2.7*S100A9(ROC 0.96)

In order to utilize the classifier for diagnosis of schizophrenia, the ΔCt of an test individual for the following genes ABOBEC3B, ADSS, ATM, CLC, CTBP1 CXCL1, DATF1 and S100A9 are measured, for example, as outlined in Example 8 and substituted into the equation above.

The test individual is considered to diagnose as a control (not having schizophrenia) when x<0, Similarly the test individual is considered to diagnose as having schizophrenia when x>0. As would be understood by a person skilled in the art, in the equation X=+27.66+1.2*APOBEC3B−4.69*ADSS+4.04*ATM+1.66*CLC−4.68*CTBP1+1.58*CXCL1−3.18*DATF1+2.7*S100A9a test individual is diagnosed as control when x>0 and diagnosed as having schizophrenia when x<0.

One of the classifiers identified for differentiating between bipolar disorder and non-bipolar disorder as shown in FIG. 6 is written as follows:

X=45.84−1.13*APOBEC3B−5.01*ADSS+0.75*CLC+1.07*CXCL1−5.13*S100A9(ROC 0.948)

One of the classifiers identified for differentiating between bipolar disorder and schizophrenia as shown in FIG. 7 is written as follows:

X=0.2+6.13*ADSS−5.58*ATM−2.69*CXCL1+3.87*DATF1+2.48*S100A9(ROC 0.972)

Example 9

Diagnosis of Individuals Utilizing Biomarker Combinations of the Invention

This example demonstrates the use of the biomarkers combinations of the invention to diagnose schizophrenia. Measurement of the RNA and/or protein products of the five biomarkers identified, for example in the classifier of Example 10 ABOBEC3, ATM, CLC, CTBP1 and DATF1 can be used to diagnose an individual as having schizophrenia or not having schizophrenia. Level of expression of the RNA and/or Protein products of the combination of biomarkers identified can be measured for a population of individuals having schizophrenia and a population of individuals not having schizophrenia and a new classifier generated to allow the diagnosis of an unknown individual as having or not having schizophrenia.

Example 10

Analysis of Gene Expression Profiles of Blood Samples from Individuals Having Schizophrenia as Compared with Gene Expression Profiles from Normal Individuals Using the Biomarkers of Table 1

This example demonstrates the use of the claimed invention to diagnose schizophrenia by detecting differential gene expression in blood samples taken from patients with schizophrenia as compared to blood samples taken from healthy patients.

Blood samples are taken from patients who are clinically diagnosed with schizophrenia as defined herein. Gene expression profiles are then analyzed and compared to profiles from patients unaffected by schizophrenia. In each case, the diagnosis of schizophrenia is corroborated by a skilled Board certified physician.

Total mRNA from a drop of blood is taken from each patient is first isolated using TRIzol® reagent (GIBCO) and fluorescently labeled probes for each blood sample are then generated, denatured and hybridized to a microarray containing full length cDNA sequences for each of the genes as described in Table 1. Detection of specific hybridization to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the 8 genes in blood samples from patients with schizophrenia as compared to non-schizophrenic patients is determined by statistical analysis using the t-test (Glantz SA. Primer of Biostatistics. 5th ed. N.Y., USA: McGraw-Hill Medical Publishing Division, 2002).

Example 11

Analysis of Gene Expression Profiles of Blood Samples from Individuals Having Schizophrenia as Compared with Gene Expression Profiles from Healthy Individuals Using the 5' Regions of the Genes Described in Table 1

This example demonstrates the use of the claimed invention to diagnose schizophrenia by detecting differential gene expression in blood samples taken from patients with schizophrenia as compared to blood samples taken from healthy patients.

Blood samples are taken from patients who are clinically diagnosed with schizophrenia as defined herein. Gene expression profiles are then analyzed and compared to profiles from patients unaffected by schizophrenia. In each case, the diagnosis of schizophrenia is corroborated by a skilled Board certified physician.

Total mRNA from a drop of blood taken from each patient is first isolated using TRIzol® reagent (GIBCO) and fluorescently labeled probes for each blood sample are then generated, denatured and hybridized to a microarray containing DNA sequences of 25 nucleotides in length corresponding to the 5' region of each of the genes as described in Table 1. Detection of specific hybridization to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the genes in blood samples from patients with schizophrenia as compared to healthy patients is determined by statistical analysis using the t test (Glantz SA. Primer of Biostatistics. 5th ed. New York, USA: McGraw-Hill Medical Publishing Division, 2002). Differential expression of each of the genes described in Table 1 is diagnostic for schizophrenia.

Example 12

Analysis of Gene Expression Profiles of Blood Samples from Individuals Having Schizophrenia as Compared with Gene Expression Profiles from Non Schizophrenic Individuals Using the 3' Regions of the Genes Described in Table 1

This example demonstrates the use of the claimed invention to diagnose schizophrenia by detecting differential gene expression in blood samples taken from patients with schizophrenia as compared to blood samples taken from healthy patients.

Blood samples are taken from patients who were clinically diagnosed with schizophrenia as defined herein. Gene expression profiles are then analyzed and compared to profiles from patients unaffected by schizophrenia. In each case, the diagnosis of schizophrenia is corroborated by a skilled Board certified physician.

Total mRNA from a drop of blood taken from each patient is first isolated using TRIzol® reagent (GIBCO) and fluorescently labeled probes for each blood sample are then generated, denatured and hybridized to a microarray containing DNA sequences of 50 nucleotides in length corresponding to the 3' region of each of the mRNA as described in Table 1. Detection of specific hybridization to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the enes in blood samples from patients with schizophrenia as compared to healthy patients is determined by statistical analysis using the t-test (Glantz SA. Primer of Biostatistics. 5th ed. New York, USA: McGraw-Hill Medical Publishing Division, 2002). Differential expression of each of the mRNA described in Table 1 is diagnostic for schizophrenia.

Example 13

Analysis of Gene Expression Profiles of Blood Samples from Individuals Having Schizophrenia as Compared with Gene Expression Profiles from Healthy Individuals Using the Internal Coding Regions Of the Genes Described in Table 1

This example demonstrates the use of the claimed invention to diagnose schizophrenia by detecting differential gene expression in blood samples taken from patients with schizophrenia as compared to blood samples taken from healthy patients.

Blood samples are taken from patients who are clinically diagnosed with schizophrenia as defined herein. Gene expression profiles are then analyzed and compared to profiles from patients unaffected by schizophrenia. In each case, the diagnosis of schizophrenia is corroborated by a skilled Board certified physician.

Total mRNA from a drop of blood taken from each patient wis as first isolated using TRIzol® reagent (GIBCO) and fluorescently labeled probes for each blood sample are then generated, denatured and hybridized to a microarray containing DNA sequences of 70 nucleotides in length corresponding to the internal coding region of each of the genes as described in Table 1. Detection of specific hybridization to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the genes in blood samples from patients with schizophrenia as compared to healthy patients is then determined by statistical analysis using the t-test (Glantz SA. Primer of Biostatistics. 5th ed. New York, USA: McGraw-Hill Medical Publishing Division, 2002). Differential expression of each of the mRNA described in Table 1 is diagnostic for schizophrenia.

Example 14

Analysis of Blood Samples from Individuals Having Schizophrenia as Compared with Blood Samples from Healthy Individuals Using Monoclonal Antibodies Directed to the Polypeptides Encoded by the Genes Described in Table 1

This example demonstrates the use of the claimed invention to diagnose schizophrenia by detecting differential gene expression in blood samples taken from patients with schizophrenia as compared to blood samples taken from healthy patients.

Blood samples are taken from patients who are clinically diagnosed with schizophrenia as defined herein. Gene expression profiles are then analyzed and compared to profiles from patients unaffected by schizophrenia. In each case, the diagnosis of schizophrenia is corroborated by a skilled Board certified physician.

Total cellular protein from blood taken from each patient is first isolated and labelled using the BD Clontech Protein Extraction and labelling kit (Catalogue #K1848-1 or #631786). Briefly, the Extraction Protocol consists of three main steps: mechanically disrupting the cells, solubilizing the cells, and centrifuging the extract. The process may start with a cell pellet or frozen tissue and may use any method of mechanical disruption—French press, sonication, mincing, or grinding. Once disrupted, the sample is solubilized by adding the Extraction/Labeling Buffer (1:20 w/v). Because the Buffer is formulated for labeling with N-hydroxysuccinimide (NHS)-ester dyes (e.g. Cy3 and CyS dyes), it does not contain any protease inhibitors or reducing agents that would compete for reaction with the dye. After extraction, the sample is centrifuged to pellet insoluble material such as chromosomal DNA. The soluble extract is then labelled with Cy3 and Cy5 Fluorescent Dyes (monofunctional NHS-esters). The labelled proteins are then incubated with an array of monoclonal antibodies which are directed to full length polypeptides encoded by the genes described in Table 1. Detection of specific binding to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the genes in blood samples from patients with schizophrenia as compared to healthy patients is determined by statistical analysis using the Wilcox Mann Whitney rank sum test (Glantz SA. Primer of Biostatistics. 5th ed. New York, USA: McGraw-Hill Medical Publishing Division, 2002). Differential expression of each of the genes described in Table 1 is diagnostic for schizophrenia.

Example 15

Analysis of Blood Samples from Individuals Having Schizophrenia as Compared with blood samples from healthy individuals using Monoclonal Antibodies Directed to the Amino Terminal Region of Polypeptides Encoded by the 5' Regions of the Genes Described in Table 1

This example demonstrates the use of the claimed invention to diagnose schizophrenia by detecting differential gene expression in blood samples taken from patients with schizophrenia as compared to blood samples taken from healthy patients.

Blood samples are taken from patients who are clinically diagnosed with schizophrenia as defined herein. Gene expression profiles are then analyzed and compared to profiles from patients unaffected by schizophrenia. In each case, the diagnosis of schizophrenia is corroborated by a skilled Board certified physician.

Total cellular protein from blood taken from each patient is first isolated and labelled using the BD Clontech Protein Extraction and labelling kit (Catalogue #K1848-1 or #631786). Briefly, the Extraction Protocol consists of three main steps: mechanically disrupting the cells, solubilizing the cells, and centrifuging the extract The process may start with a cell pellet or frozen tissue and may use any method of mechanical disruption—French press, sonication, mincing, or grinding. Once disrupted, the sample is solubilized by adding the Extraction/Labeling Buffer (1:20 w/v). Because the Buffer is formulated for labeling with N-hydroxysuccinimide (NHS)-ester dyes (e.g. Cy3 and CyS dyes), it does not contain any protease inhibitors or reducing agents that would compete for reaction with the dye. After extraction, the sample is centrifuged to pellet insoluble material such as chromosomal DNA. The soluble extract is then labelled with Cy3 and Cy5 Fluorescent Dyes (monofunctional NHS-esters). The labelled proteins are then incubated with an array of monoclonal antibodies which are directed to amino terminal regions of polypeptides encoded by the 5' regions of the genes described in in Table 1. Detection of specific binding to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the 3 genes in blood samples from patients with schizophrenia as compared to healthy patients is determined by statistical analysis using the Wilcox Mann Whitney rank sum test (Glantz SA. Primer of Biostatistics. 5th ed. New York, USA: McGraw-Hill Medical Publishing Division, 2002). Differential expression of each of the genes described in Table 1 is diagnostic for schizophrenia.

Example 16

Analysis of Blood Samples from Individuals Having Schizophrenia as Compared with Blood Samples from Healthy Individuals Using Monoclonal Antibodies Directed to the Carboxy Terminal Region of Polypeptides Encoded by the 3' Regions of the Genes Described in Table 1.

This example demonstrates the use of the claimed invention to diagnose schizophrenia by detecting differential gene expression in blood samples taken from patients with schizophrenia as compared to blood samples taken from healthy patients.

Blood samples are taken from patients who were clinically diagnosed with schizophrenia as defined herein. Gene expression profiles are then analyzed and compared to profiles from patients unaffected by schizophrenia. In each case, the diagnosis of schizophrenia is corroborated by a skilled Board certified physician.

Total cellular protein from blood taken from each patient is first isolated and labelled using the BD Clontech Protein Extraction and labelling kit (Catalogue #K1 848-1 or #631786). Briefly, the Extraction Protocol consists of three main steps: mechanically disrupting the cells, solubilizing the cells, and centrifuging the extract The process may start with a cell pellet or frozen tissue and may use any method of mechanical disruption—French press, sonication, mincing, or grinding. Once disrupted, the sample is solubilized by adding the Extraction/Labeling Buffer (1:20 w/v). Because the Buffer is formulated for labeling with N-hydroxysuccinimide (NHS)-ester dyes (e.g. Cy3 and CyS dyes), it does not contain any protease inhibitors or reducing agents that would compete for reaction with the dye. After extraction, the sample is centrifuged to pellet insoluble material such as chromosomal DNA. The soluble extract is then labelled with Cy3 and Cy5 Fluorescent Dyes (monofunctional NHS-esters). The labelled proteins are then incubated with an array of monoclonal antibodies which are directed to the carboxy terminal regions of polypeptides encoded by the 3' regions of the genes described in in Table 1. Detection of specific binding to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the genes in blood samples from patients with schizophrenia as compared to healthy patients is determined by statistical analysis using the Wilcox Mann Whitney rank sum test (Glantz SA. Primer of Biostatistics. 5th ed. New York, USA: McGraw-Hill Medical Publishing Division, 2002). Differential expression of each of the genes described in in Table 1 is diagnostic for schizophrenia.

Example 17

Analysis of Blood Samples from Individuals Having Schizophrenia as Compared with Blood Samples from Healthy Individuals Using Antibodies Directed to the Internal Polypeptide Region of Polypeptides Encoded by the Internal Coding Region of the Genes Described in Table 1.

This example demonstrates the use of the claimed invention to diagnose schizophrenia by detecting differential gene expression in blood samples taken from patients with schizophrenia as compared to blood samples taken from healthy patients.

Blood samples are taken from patients who were clinically diagnosed with schizophrenia as defined herein. Gene expression profiles are then analyzed and compared to profiles from patients unaffected by schizophrenia. In each case, the diagnosis of schizophrenia is corroborated by a skilled Board certified physician.

Total cellular protein from blood taken from each patient is first isolated and labelled using the BD Clontech Protein Extraction and labelling kit (Catalogue #K1848-1 or #631786). Briefly, the Extraction Protocol consists of three main steps: mechanically disrupting the cells, solubilizing the cells, and centrifuging the extract. The process may start with a cell pellet or frozen tissue and may use any method of mechanical disruption—French press, sonication, mincing, or grinding. Once disrupted, the sample is solubilized by adding the Extraction/Labeling Buffer (1:20 w/v). Because the Buffer is formulated for labeling with N-hydroxysuccinimide (NHS)-ester dyes (e.g. Cy3 and CyS dyes), it does not contain any protease inhibitors or reducing agents that would compete for reaction with the dye. After extraction, the sample is centrifuged to pellet insoluble material such as chromosomal DNA. The soluble extract is then labelled with Cy3 and Cy5 Fluorescent Dyes (monofunctional NHS-esters). The labelled proteins are then incubated with an array of monoclonal antibodies which are directed to internal polypeptide regions of polypeptides encoded by the internal coding regions of the genes described in Table 1. Detection of specific binding to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the genes in blood samples from patients with schizophrenia as compared to healthy patients is determined by statistical analysis using the Wilcox Mann Whitney rank sum test (Glantz SA. Primer of Biostatistics. 5th ed. New York, USA: McGraw-Hill Medical Publishing Division, 2002). Differential expression of each of the genes described in Table 1 is diagnostic for schizophrenia.

Variations, modifications, and other implementations of what is described herein will occur to those of ordinary skill in the art without departing from the spirit and scope of the invention. The references provided below are incorporated herein by reference in their entireties. All patents, patent applications, and published references cited herein are hereby incorporated by reference in their entirety.

While this invention has been particularly shown and described with references to preferred embodiments thereof, it will be understood by those skilled in the art that various changes in form and details may be made therein without departing from the scope of the invention encompassed by the appended claims. Those skilled in the art will recognise that other embodiments and configurations known in the art would be within the spirit and scope of the present invention.

What is claimed is:

1. A kit for determining a likelihood that a test subject has schizophrenia as opposed to being healthy, the kit containing, for each gene of a set of genes consisting of ABOBEC3B, ADSS, ATM, CLC, CTBP1, CXCL1, DATF1 and S100A9, primers for amplifying DNA complementary to RNA encoded specifically by the gene, the primers having the nucleic acid sequences identified as SEQ ID NOs: 1-16.

2. The kit of claim 1, wherein the kit further contains a thermostable DNA polymerase.

3. A set of primers consisting of, for each gene of a set of genes consisting of ABOBEC3B, ADSS, ATM, CLC, CTBP1, CXCL1, DATF1 and S100A9, primers for amplifying DNA complementary to RNA encoded specifically by the gene, wherein each of the primers hybridizes under standard stringent conditions to RNA encoded by the gene or to the complement thereof.

4. The set of claim 3, wherein each of the primers is complementary to RNA encoded by the gene or to the complement thereof.

5. The set of claim 3, wherein the set consists of primers having the nucleic acid sequences identified as SEQ ID NOs: 1-16.

6. The set of claim 3, wherein the set is packaged or provided with a thermostable DNA polymerase.

* * * * *

SEQUENCE LISTING

```
<160> NUMBER OF SEQ ID NOS: 16

<210> SEQ ID NO 1
<211> LENGTH: 22
<212> TYPE: DNA
<213> ORGANISM: artificial
<220> FEATURE:
<223> OTHER INFORMATION: Forward Primer for ADSS

<400> SEQUENCE: 1

ctgcgttggc acttaccaag tt                                    22


<210> SEQ ID NO 2
<211> LENGTH: 20
<212> TYPE: DNA
<213> ORGANISM: artificial
<220> FEATURE:
<223> OTHER INFORMATION: Reverse Primer for ADSS

<400> SEQUENCE: 2

gacttcttgg tttgctggga                                       20


<210> SEQ ID NO 3
<211> LENGTH: 27
<212> TYPE: DNA
<213> ORGANISM: artificial
<220> FEATURE:
<223> OTHER INFORMATION: Forward Primer for APOBEC3B

<400> SEQUENCE: 3

ctcagatacc tgatggatcc agacaca                               27


<210> SEQ ID NO 4
<211> LENGTH: 22
<212> TYPE: DNA
<213> ORGANISM: artificial
<220> FEATURE:
<223> OTHER INFORMATION: Reverse Primer for APOBE3C

<400> SEQUENCE: 4
```

cgctccacct catagcacaa gt 22

<210> SEQ ID NO 5
<211> LENGTH: 20
<212> TYPE: DNA
<213> ORGANISM: artificial
<220> FEATURE:
<223> OTHER INFORMATION: Forward Primer for ATM

<400> SEQUENCE: 5
tgtggatggc atgggcatta 20

<210> SEQ ID NO 6
<211> LENGTH: 27
<212> TYPE: DNA
<213> ORGANISM: artificial
<220> FEATURE:
<223> OTHER INFORMATION: Reverse Primer for ATM

<400> SEQUENCE: 6
gaaggacctc tacaatggtt aacagag 27

<210> SEQ ID NO 7
<211> LENGTH: 23
<212> TYPE: DNA
<213> ORGANISM: artificial
<220> FEATURE:
<223> OTHER INFORMATION: Forward Primer for CLC

<400> SEQUENCE: 7
gccagataag taccaggtaa tgg 23

<210> SEQ ID NO 8
<211> LENGTH: 20
<212> TYPE: DNA
<213> ORGANISM: artificial
<220> FEATURE:
<223> OTHER INFORMATION: Reverse Primer for CLC

<400> SEQUENCE: 8
atctctccac acttgcacca 20

<210> SEQ ID NO 9
<211> LENGTH: 20
<212> TYPE: DNA
<213> ORGANISM: artificial
<220> FEATURE:
<223> OTHER INFORMATION: Forward Primer for CTBP1

<400> SEQUENCE: 9
atcacaggcc ggatcccaga 20

<210> SEQ ID NO 10
<211> LENGTH: 20
<212> TYPE: DNA
<213> ORGANISM: artificial
<220> FEATURE:
<223> OTHER INFORMATION: Reverse Primer for CTBP1

<400> SEQUENCE: 10
attgagctca gggtgcacga 20

<210> SEQ ID NO 11
<211> LENGTH: 20
<212> TYPE: DNA
<213> ORGANISM: artificial

```
<220> FEATURE:
<223> OTHER INFORMATION: Forward Primer for CXCL1

<400> SEQUENCE: 11

accgaagtca tagccacact                                              20


<210> SEQ ID NO 12
<211> LENGTH: 22
<212> TYPE: DNA
<213> ORGANISM: artificial
<220> FEATURE:
<223> OTHER INFORMATION: Reverse Primer for CXCL1

<400> SEQUENCE: 12

gttggatttg tcactgttca gc                                           22


<210> SEQ ID NO 13
<211> LENGTH: 24
<212> TYPE: DNA
<213> ORGANISM: artificial
<220> FEATURE:
<223> OTHER INFORMATION: Forward Primer for PATF1

<400> SEQUENCE: 13

agcagaagtc tagcgaagac caag                                         24


<210> SEQ ID NO 14
<211> LENGTH: 20
<212> TYPE: DNA
<213> ORGANISM: artificial
<220> FEATURE:
<223> OTHER INFORMATION: Reverse Primer for PATF1

<400> SEQUENCE: 14

gcctctatca caggctggaa                                              20


<210> SEQ ID NO 15
<211> LENGTH: 22
<212> TYPE: DNA
<213> ORGANISM: artificial
<220> FEATURE:
<223> OTHER INFORMATION: Forward Primer for S100A9

<400> SEQUENCE: 15

tttgggacag agtgcaagac ga                                           22


<210> SEQ ID NO 16
<211> LENGTH: 24
<212> TYPE: DNA
<213> ORGANISM: artificial
<220> FEATURE:
<223> OTHER INFORMATION: Reverse Primer for S100A9

<400> SEQUENCE: 16

ccagcttcac agagtattgg tgga                                         24
```